(12) United States Patent
Moon et al.

(10) Patent No.: US 11,192,959 B2
(45) Date of Patent: Dec. 7, 2021

(54) ANTIBODY BINDING TO CARBONIC ANHYDRASE AND USE THEREOF

(71) Applicant: Aprogen KIC Inc., Seongnam-si (KR)

(72) Inventors: Yoo Ri Moon, Seoul (KR); Sangsoon Yoon, Seoul (KR); Jeong Won Hong, Seoul (KR); Eun Jung Kim, Seoul (KR); Da Bin Choi, Hwaseong-si (KR)

(73) Assignee: APROGEN MEDICINES INC., Seongnam-si (KR)

( * ) Notice: Subject to any disclaimer, the term of this patent is extended or adjusted under 35 U.S.C. 154(b) by 282 days.

(21) Appl. No.: 16/347,254

(22) PCT Filed: Nov. 14, 2017

(86) PCT No.: PCT/KR2017/012892
§ 371 (c)(1),
(2) Date: May 3, 2019

(87) PCT Pub. No.: WO2018/088878
PCT Pub. Date: May 17, 2018

(65) Prior Publication Data
US 2019/0276557 A1    Sep. 12, 2019

(30) Foreign Application Priority Data

Nov. 14, 2016 (KR) .................. 10-2016-0151382

(51) Int. Cl.
| | |
|---|---|
| C07K 16/40 | (2006.01) |
| A61K 47/68 | (2017.01) |
| A61P 35/00 | (2006.01) |
| C12N 5/16 | (2006.01) |
| C12N 15/85 | (2006.01) |
| G01N 33/532 | (2006.01) |
| G01N 33/574 | (2006.01) |
| A61K 39/395 | (2006.01) |

(52) U.S. Cl.
CPC ............ *C07K 16/40* (2013.01); *A61K 39/395* (2013.01); *A61K 47/68* (2017.08); *A61P 35/00* (2018.01); *C12N 5/16* (2013.01); *C12N 15/85* (2013.01); *G01N 33/532* (2013.01); *G01N 33/574* (2013.01); *G01N 33/57415* (2013.01); *G01N 33/57419* (2013.01); *G01N 33/57423* (2013.01); *G01N 33/57434* (2013.01); *G01N 33/57438* (2013.01)

(58) Field of Classification Search
CPC ................................................... C07K 16/40
USPC .................................................... 424/133.1
See application file for complete search history.

(56) References Cited

U.S. PATENT DOCUMENTS

| | | |
|---|---|---|
| 9,359,446 B2 | 6/2016 | Zeidler et al. |
| 10,246,517 B2 | 4/2019 | Moon et al. |
| 2013/0231465 A1 | 9/2013 | Zeidler et al. |
| 2017/0342161 A1 | 11/2017 | Moon et al. |

FOREIGN PATENT DOCUMENTS

| | | |
|---|---|---|
| JP | 2013534407 | 9/2013 |
| KR | 10-1917098 | 1/2019 |
| LT | 6331 | 11/2016 |
| RU | 2536290 | 12/2014 |
| WO | 96-02552 | 2/1996 |
| WO | 2012/027493 | 3/2012 |
| WO | 2017/209318 | 12/2017 |

OTHER PUBLICATIONS

Rudikoff et al. (Proceedings of the National Academy of Sciences, 1982, 79:1979-1983).*
MacCallum et al. (Journal of Molecular Biology, 1996, 262:732-745).*
Casset et al. (Biochemical and Biophysical Research Communications, 2003, 307:198-205).*
Roitt I. et al., "Immunologija", Moskva, "Mir", 2000, pp. 110-111.
M. Singer et al., "Geny i genomy", Moskva, "Mir", 1998, vol. 1, pp. 63-64.
Mariuzza R.A., "The structural basis of antigen-antibody recognition", Ann. Rev. Biophys. Biophys. Chem., 1987, vol. 16, pp. 139-159.
Ozlem Tureci et al., "Human carbonic anhydrase XII: cDNA cloning, expression, and chromosomal localization of a carbonic anhydrase gene thatis overexpressed in some renal cell cancers", Proc. Natl. Acad. Sci., 1998, vol. 95, pp. 7608-7613.
Kobayashi, M et al "CAXII Is a Sero-Diagnostic Marker for Lung Cancer", PLoS ONE 7(3): e33952. doi:10.1371/journal.pone.0033952.
Dekaminaviciute, D et al; "Immunodetection of human carbonic anhydrase XII as a new potential biomarker of tumor cells" (Abstract only).
Haapasalo, J et al; "Identification of an alternatively spliced isoform of carbonic anhydrase XII in diffusely infiltrating astrocytic gliomas", Neuro-Oncology, Apr. 2008.
Kivela, A et al; "Expression of a Novel Transmembrane Carbonic Anhydrase Isozyme XII in Normal Human Gut and Colorectal Tumors", American Journal of Pathology, vol. 156, No. 2, Feb. 2000.
Karhumaa, P et al; "Expression of the transmembrane carbonic anhydrases, CA IX and CA XII, in the human male excurrent ducts", Molecular Human Reproduction, vol. 7, Issue 7, Jul. 2001, pp. 611-616, https://doi.org/10.1093/molehr/7.7.611.

(Continued)

*Primary Examiner* — Sean E Aeder
(74) *Attorney, Agent, or Firm* — Lex IP Meister, PLLC

(57) ABSTRACT

Provided is an antibody that recognizes and binds to carbonic anhydrase or antigen-binding fragment, a nucleic acid molecule coding for the antibody or antigen-binding fragment, a vector carrying the nucleic acid molecule, a host cell including the nucleic acid molecule or the vector, and use of the antibody or antigen-binding fragment thereof in the alleviation, prevention, treatment or diagnosis of solid cancers.

19 Claims, 36 Drawing Sheets

Specification includes a Sequence Listing.

(56) References Cited

OTHER PUBLICATIONS

Kristiina Nordfors et al., "The tumour-associated carbonic anhydrases CA II, CA IX and CA XII in a group of medulloblastomas and supratentorial primitive neuroectodermal tumours: an association of CA IX with poor prognosis", BMC cancer, vol. 10, No. 148, 2010.

Barbara Ulmasov et al., "Purification and kinetic analysis of recombinant CA XII, a membrane carbonic anhydrase overexpressed in certain cancers", Proc Natl Acad Sci USA, vol. 97, No. 26, pp. 14212-14217, 2000.

Juan C. Almagro et al., "Humanization of antibodies", Frontiers in Bioscience, vol. 13, pp. 1619-1633, 2008.

Im Muno Gene Tics, "IMGT/V-QUEST Welcome page", Feb. 19, 2019, http://www.imgt.org/IMGT_vquest/share/textes/.

Prof. Andrew C.R., "Antibodies", UCL, Last modified on Feb. 5, 2019, http://www.bioinf.org.uk/abs/.

Lee K. Sun et al., "Chimeric antibody with human constant regions and mouse variable regions directed against carcinoma-associated antigen 17-1A", Proc Natl Acad Sci USA, vol. 84, No. 1, pp. 214-218, 1987.

Sherie L. Morrison et al., "Chimeric human antibody molecules: Mouse antigen-binding domains with human constant region domains", Proc. Natl. Acad. Sci. USA, vol. 81, pp. 6851-6855, 1984.

Sherie L. Morrison et al., "Genetically Engineered Antibody Molecules", Adv. Immunol., vol. 44, pp. 65-92, 1988.

Martine Verhoeyen et al., "Reshaping Human Antibodies: Grafting an Antilysozyme Activity", Science, vol. 239, pp. 1534-1536, 1988.

Eduardo A. Padlan, "A Possible Procedure for Reducing the Immunogenicity of Antibody Variable Domains While Preserving Their Liga~D-Binding Properties", Molecular Immunology, vol. 28, No. 415, pp. 489-498, 1991.

Eduardo A. Padlan, "Anatomy of the Antibody Molecule", Molecular Immunology, vol. 31, No. 3, pp. 169-217, 1994.

Dovile Dekaminaviciute et al., "Monoclonal antibodies raised against 167-180 aa sequence of human carbonic anhydrase XII inhibit its enzymatic activity", Journal of Enzyme Inhibition and Medicinal Chemistry, vol. 29, No. 6, pp. 804-810, 2014.

Douglas A. Whittington et al., "Crystal structure of the dimeric extracellular domain of human carbonic anhydrase XII, a bitopic membrane protein overexpressed in certain cancer tumor cells", PNAS, vol. 98, No. I7, pp. 9545-9550, Aug. 14, 2001.

Dovile Dekaminaviciute et al., "Development and Characterization of New Monoclonal Antibodies against Human Recombinant CA XII", Biomed Research International, vol. 2014, pp. 1-11, May 20, 2014. https://doi.org/10.1155/2014/309307.

EPO, Supplementary European Search Report of EP 17870532.3 dated Jun. 22, 2020.

\* cited by examiner

[Fig. 1]
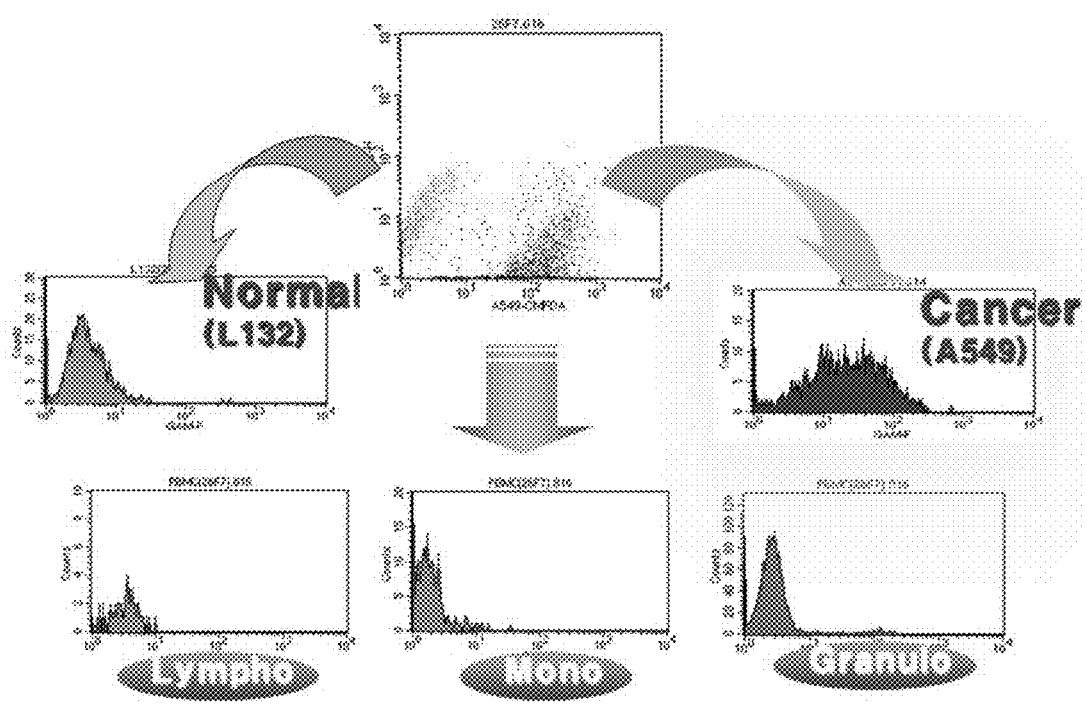

[Fig. 2]
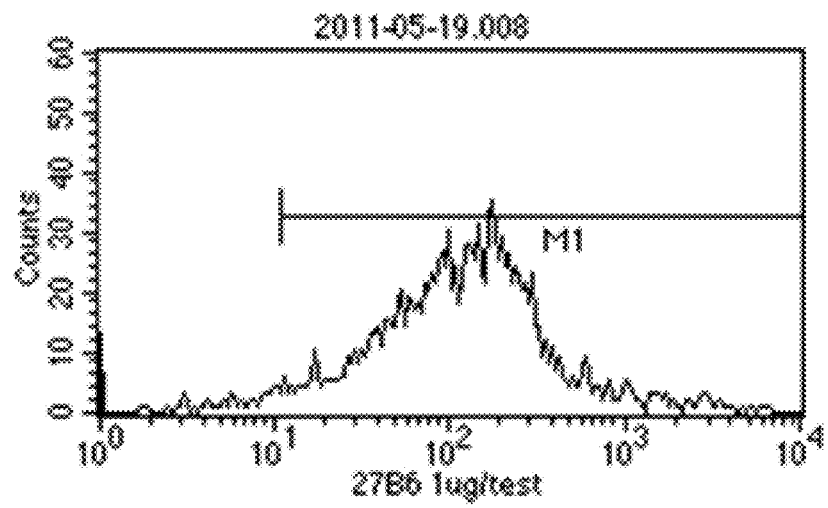
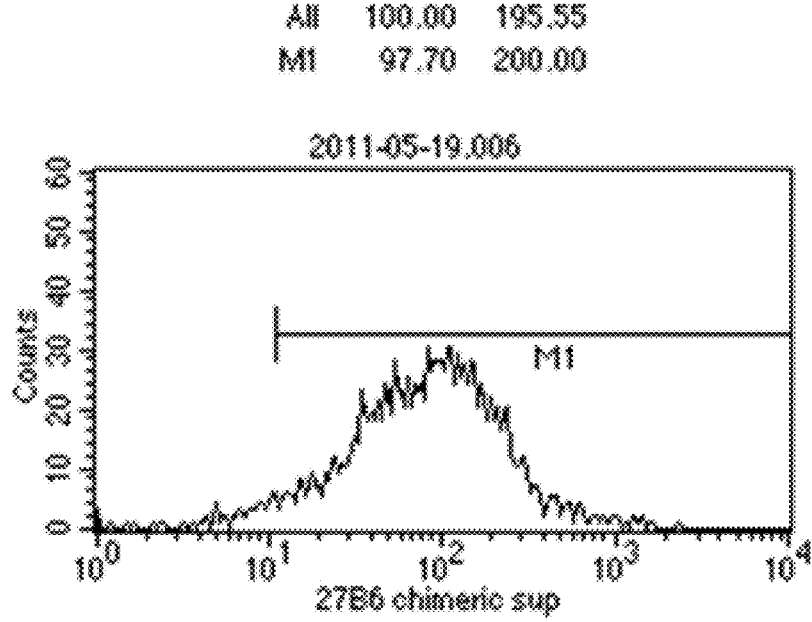

[Fig. 3]
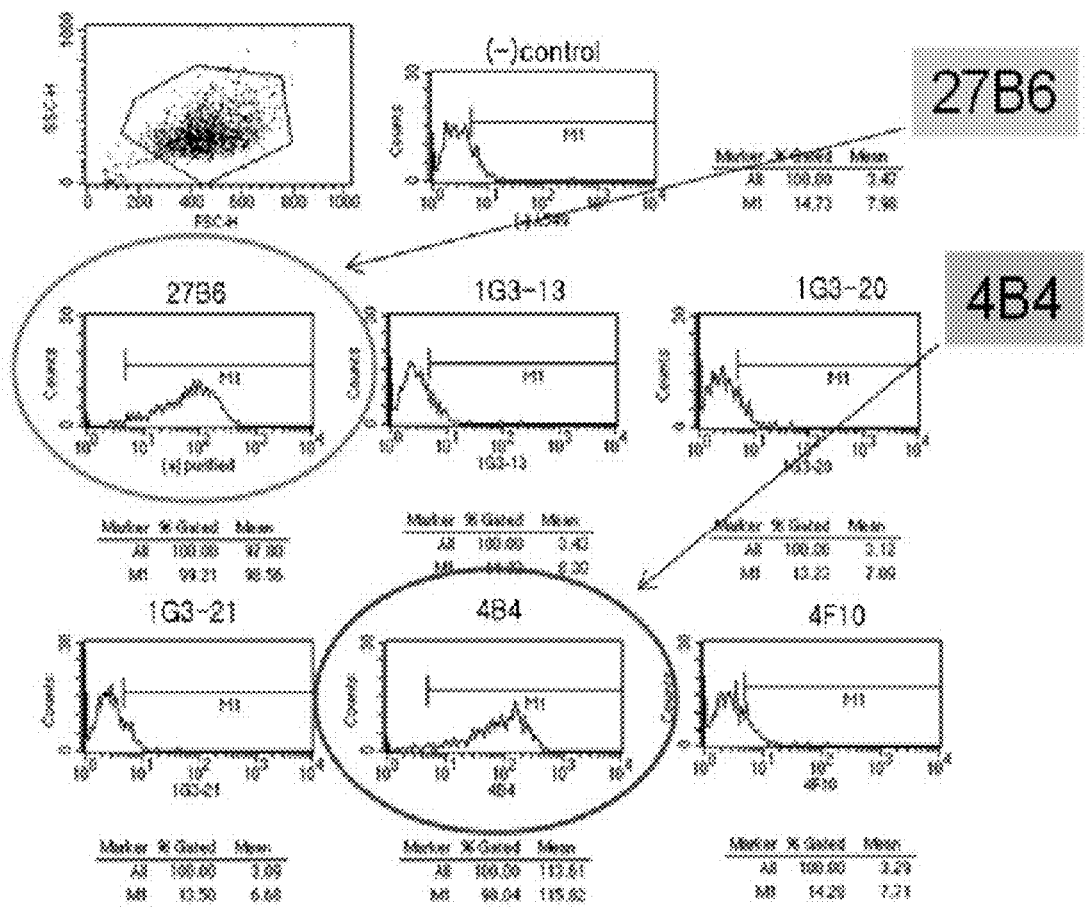

[Fig. 4]
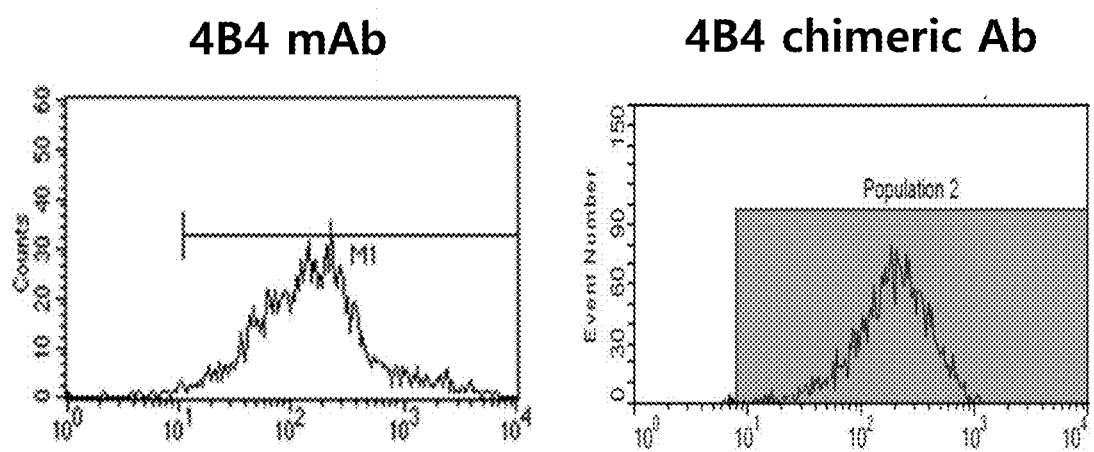

[Fig. 5a]
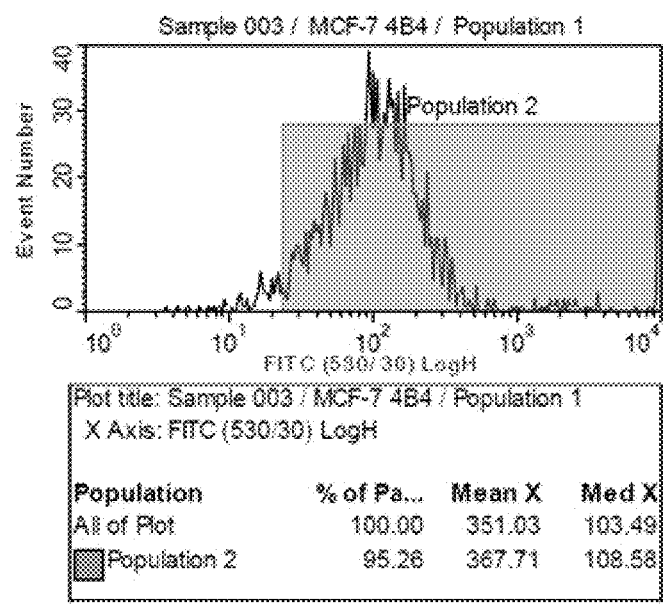
ER: Estrogen receptor
PR: Progesterone Receptor
HER2: human epidermal growth
      factor receptor 2

[Fig. 5b]
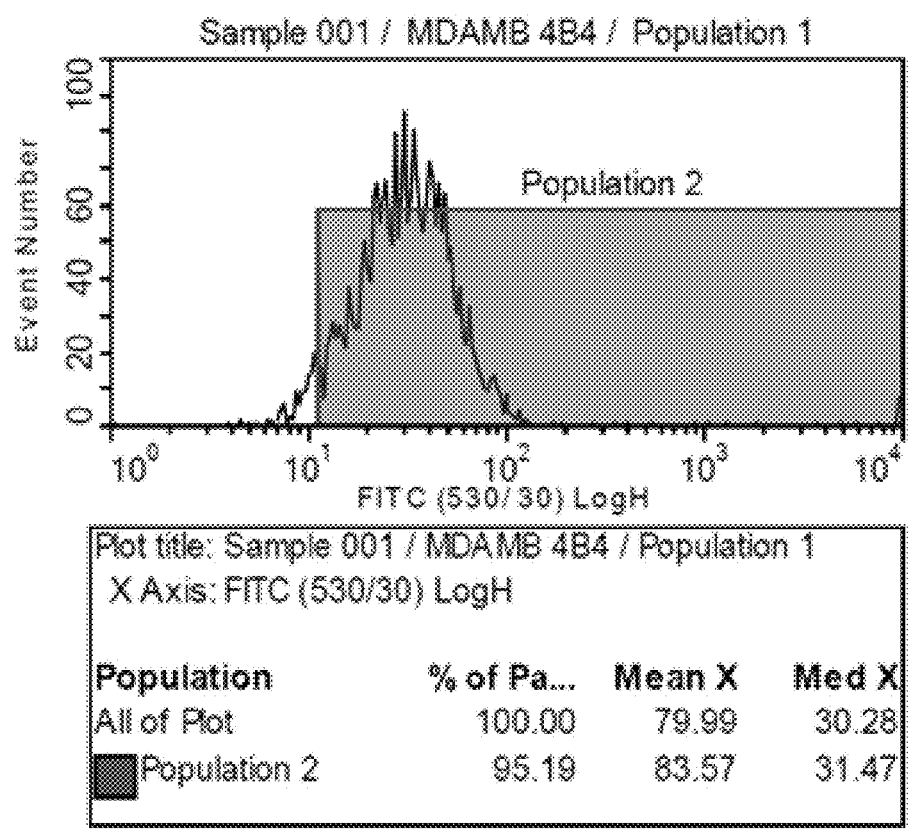
ER: Estrogen receptor
PR: Progesterone Receptor
HER2: human epidermal growth
     factor receptor 2

[Fig. 5c]
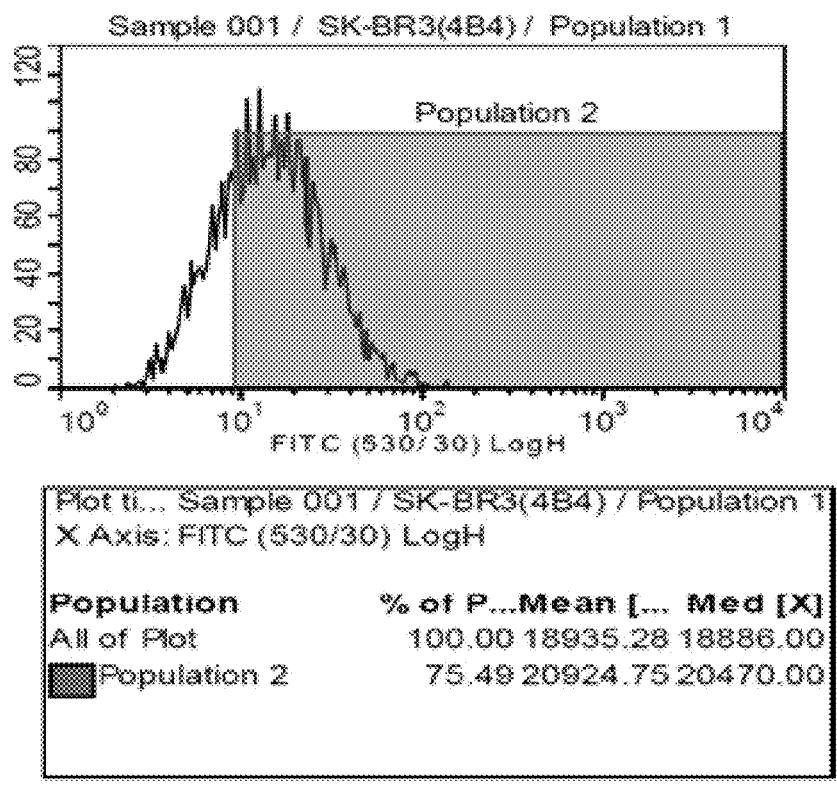
ER: Estrogen receptor
PR: Progesterone Receptor
HER2: human epidermal growth
   factor receptor 2

[Fig. 6]
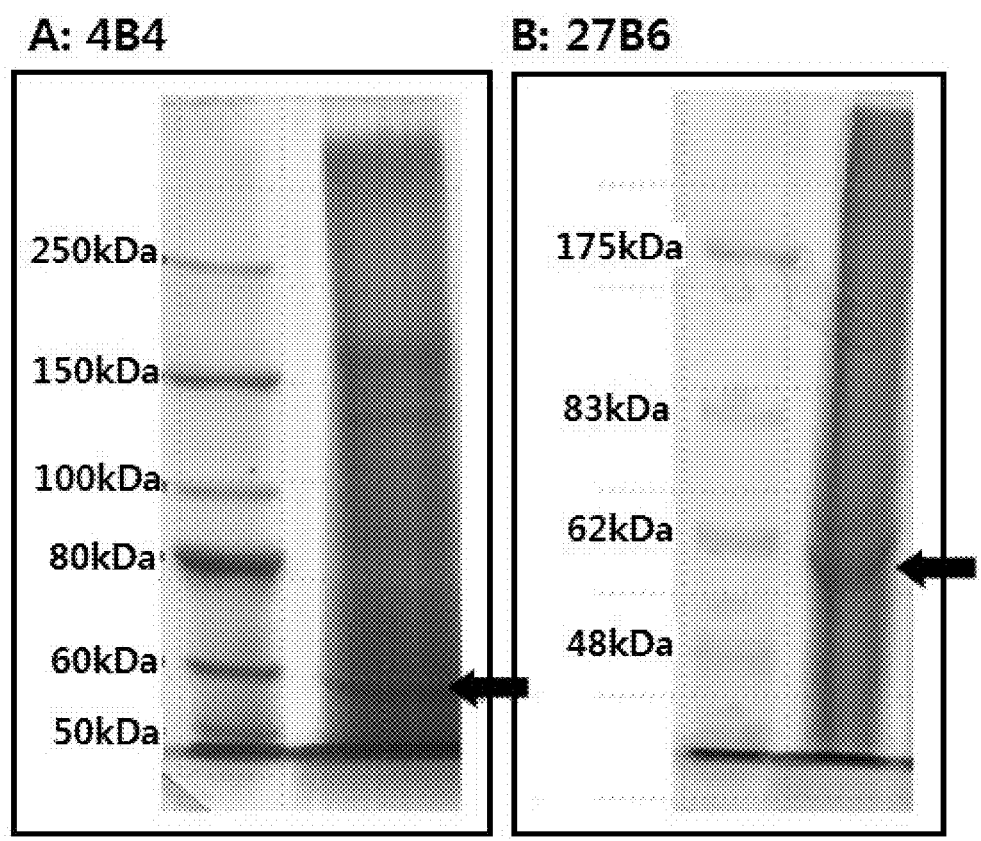

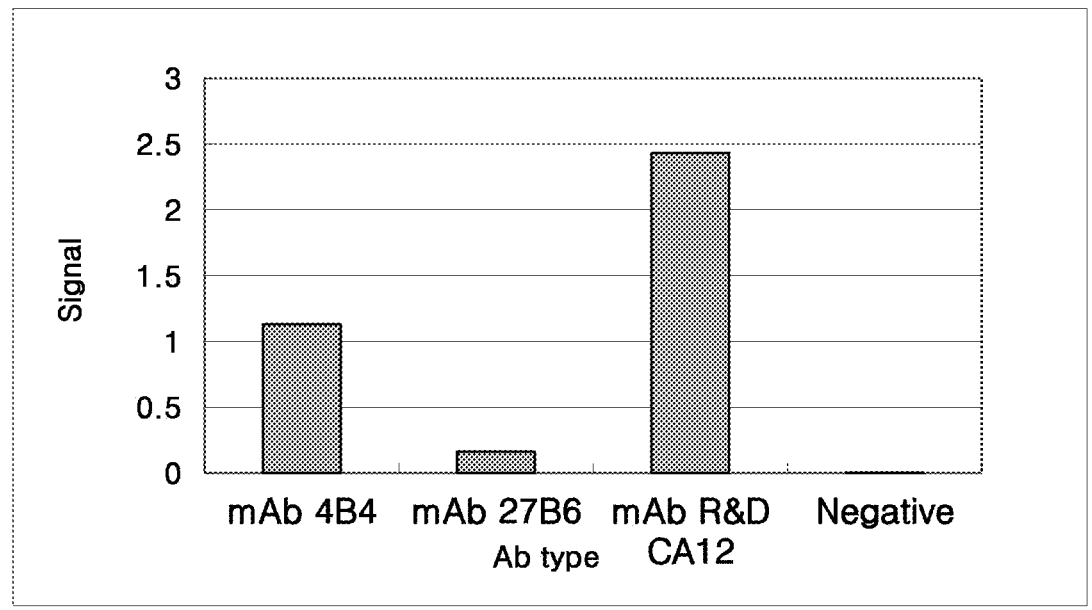
[Fig. 7]

[Fig. 8]
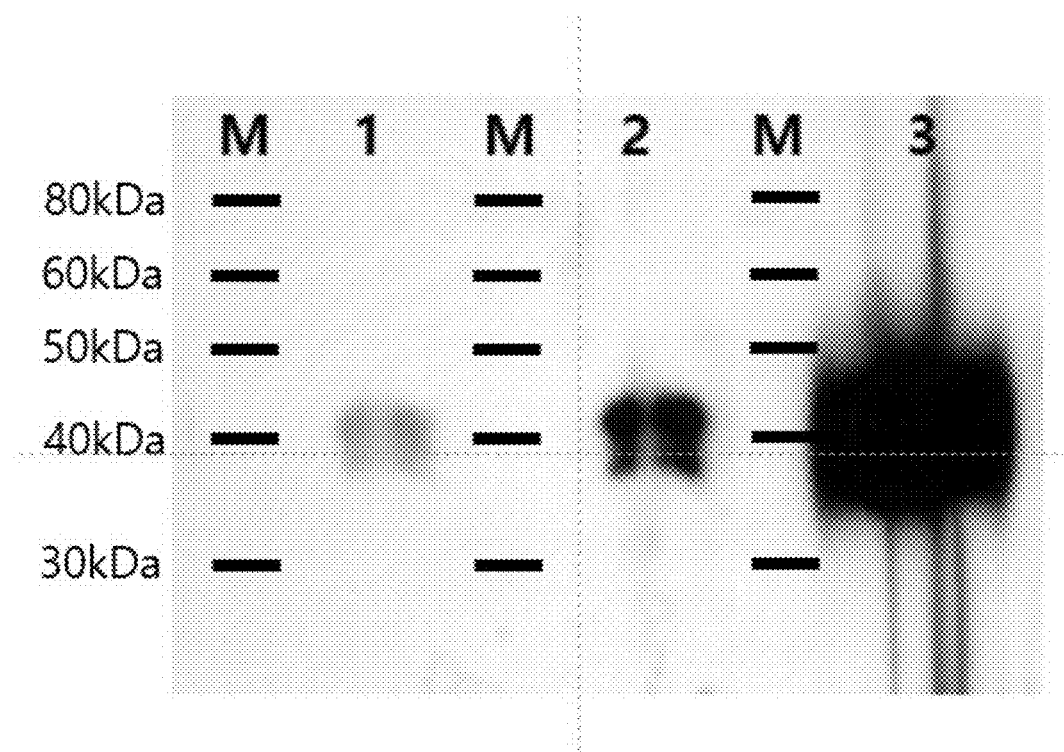

[Fig. 9]
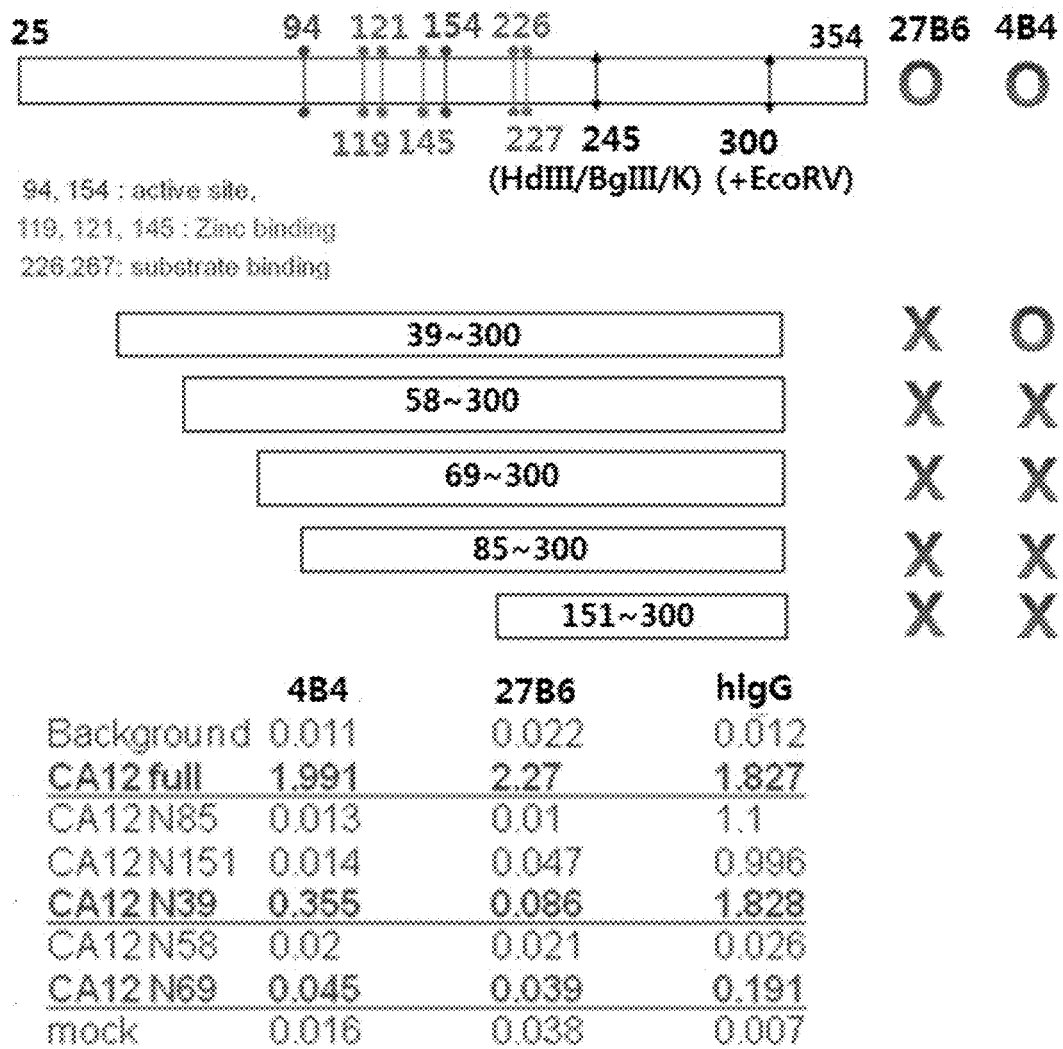

[Fig. 10]
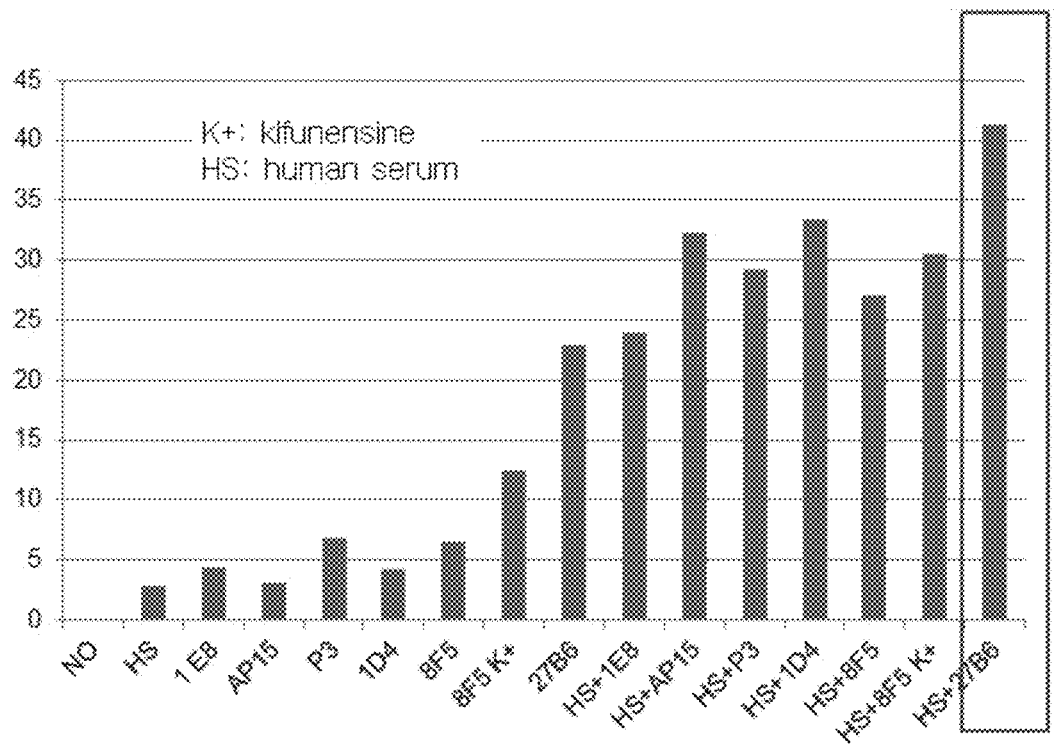
[Fig. 11]
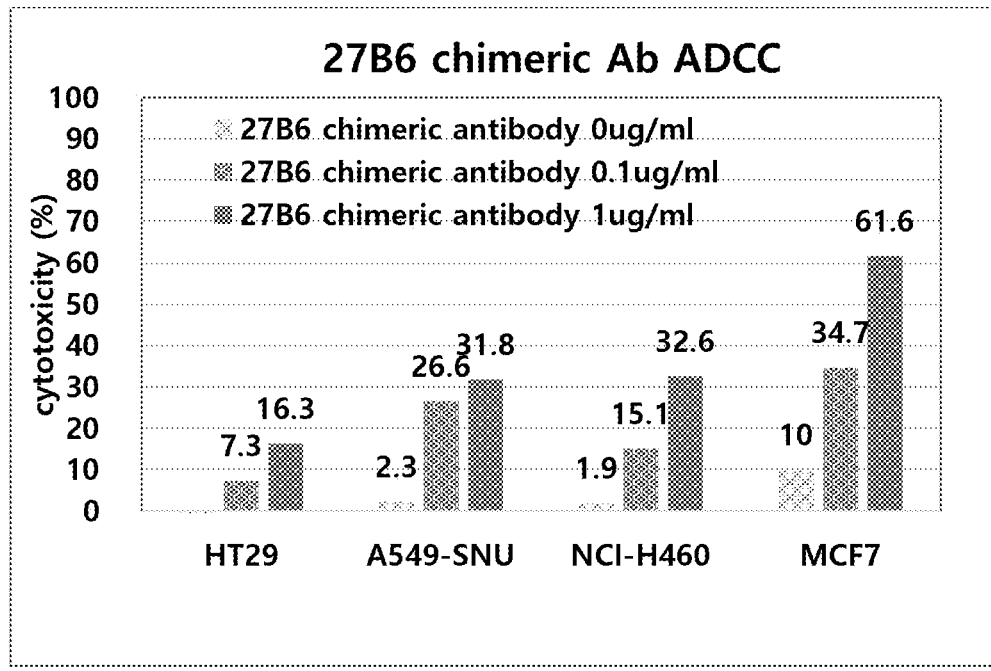

[Fig. 12]
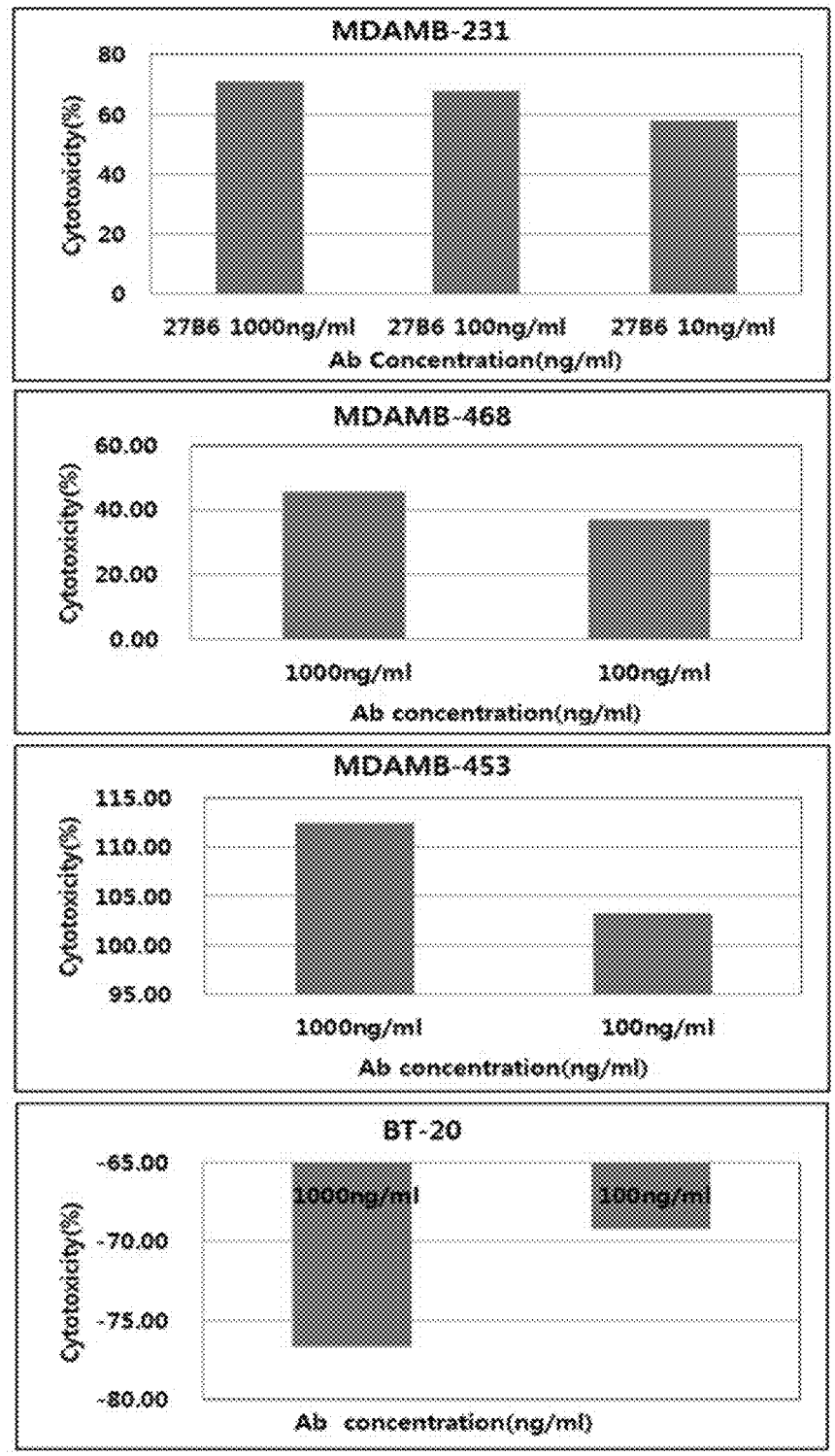

[Fig. 13]
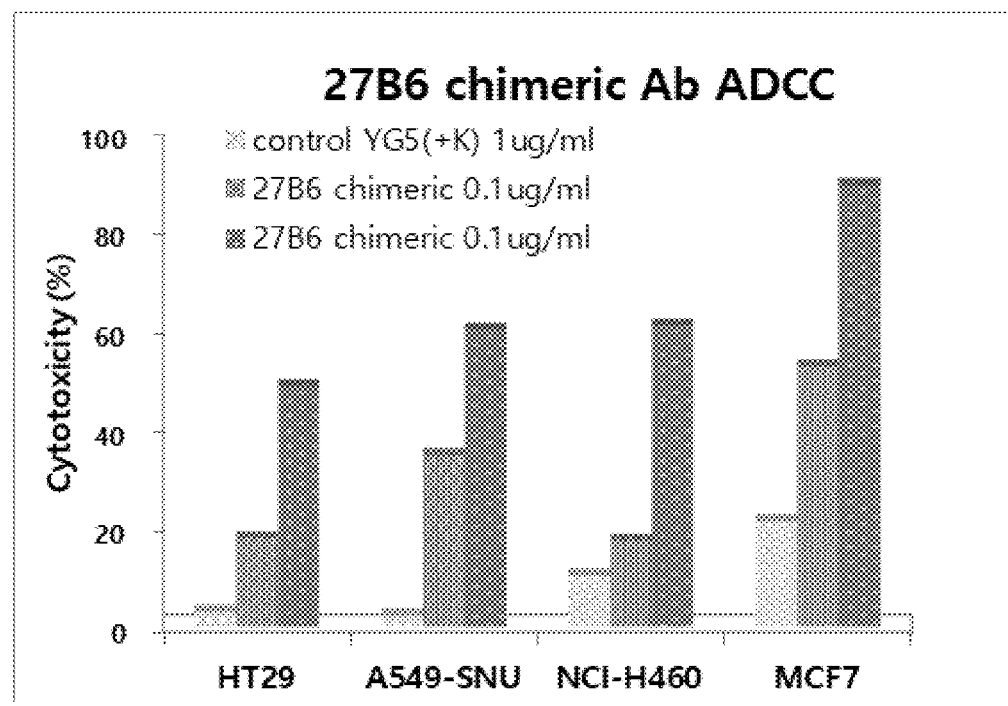
HT29: human colorectal adenocarcinoma
A549: human lung adenocarcinoma
NCI-H460: human non-small cell lung carcinoma
MCF7: human breast adenocarcinoma(ER+/ PR+/ ERBB2-)

[Fig. 14]
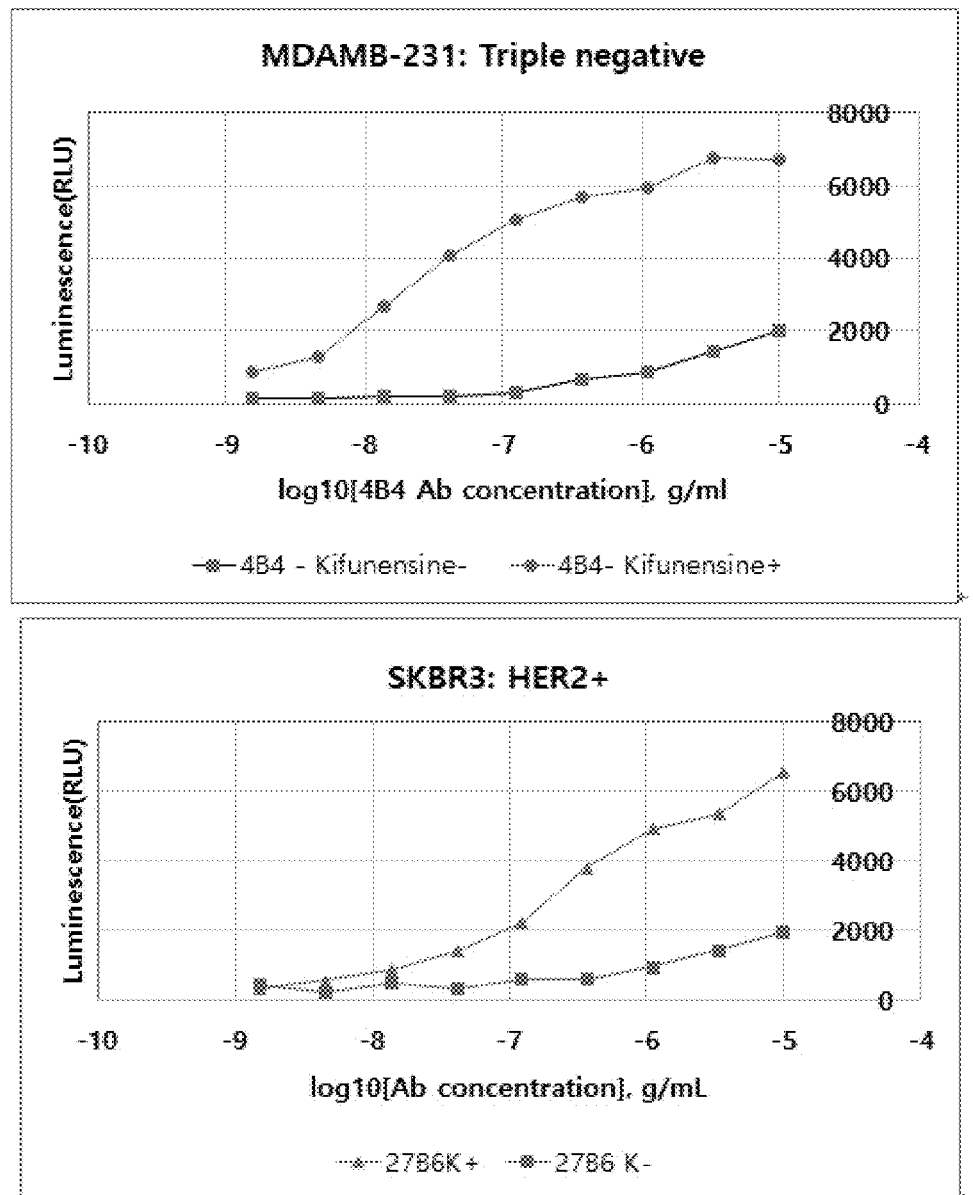

[Fig. 15]
CA12 expression on MDA-MB-231 cells
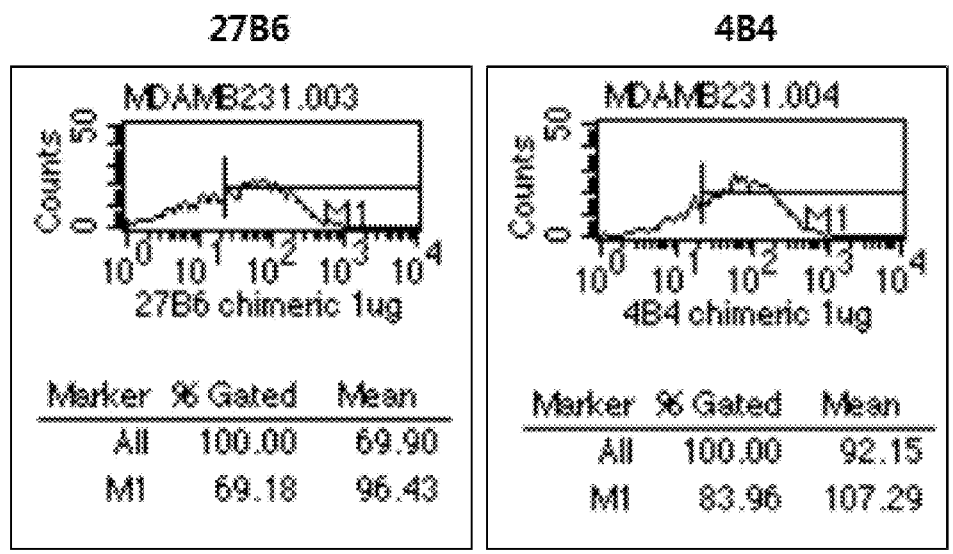

[Fig. 16]
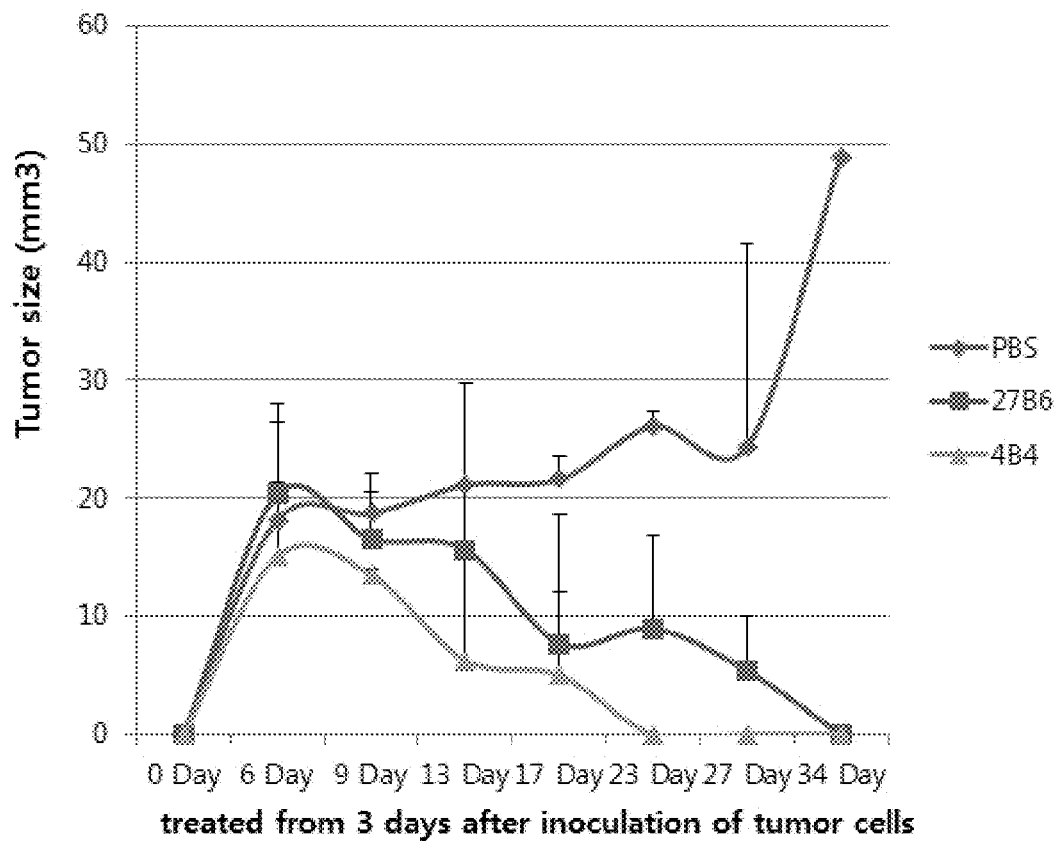
treated from 3 days after inoculation of tumor cells
| Cell line | MDAMB-231 ( TNBC cell line) |
|---|---|
| Cell inoculation No. | $1*10^7$ |
| Injection site | S.C.-flank |
| Chimeric antibody | 27B6, 4B4 |
| Dose / injection time | 12mg/kg, 3 time injection for 2 weeks/ I.P. |

[Fig. 17]
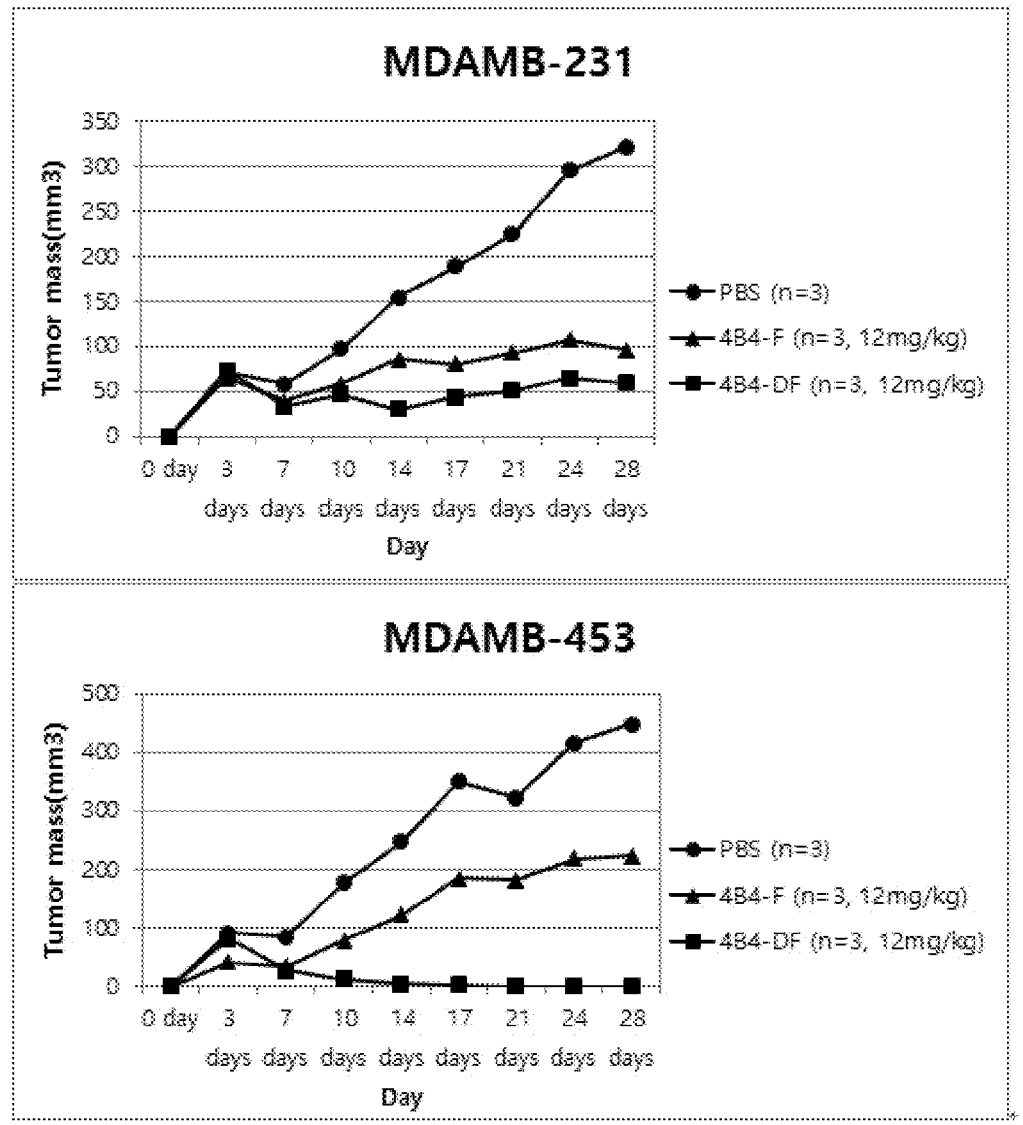

[Fig. 18]
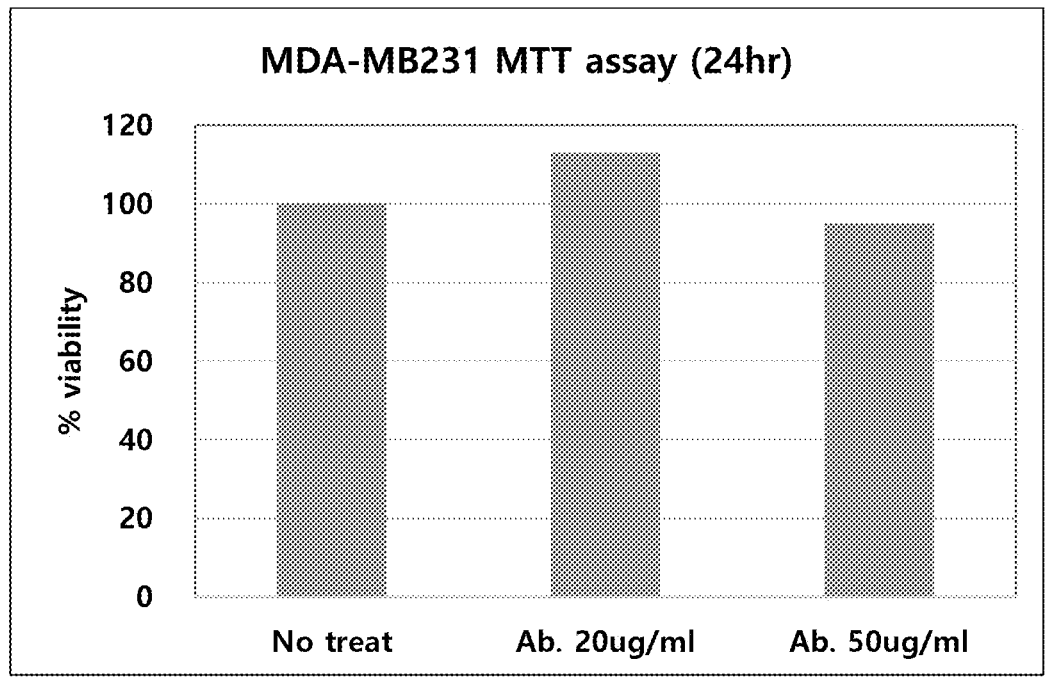
[Fig. 19]
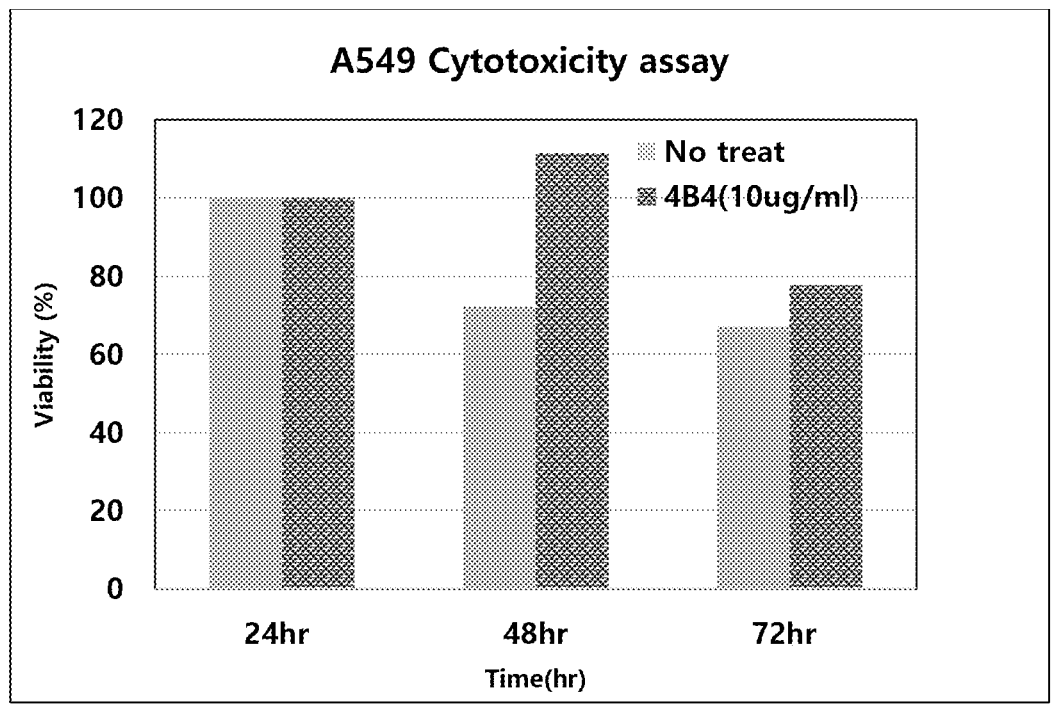

[Fig. 20]
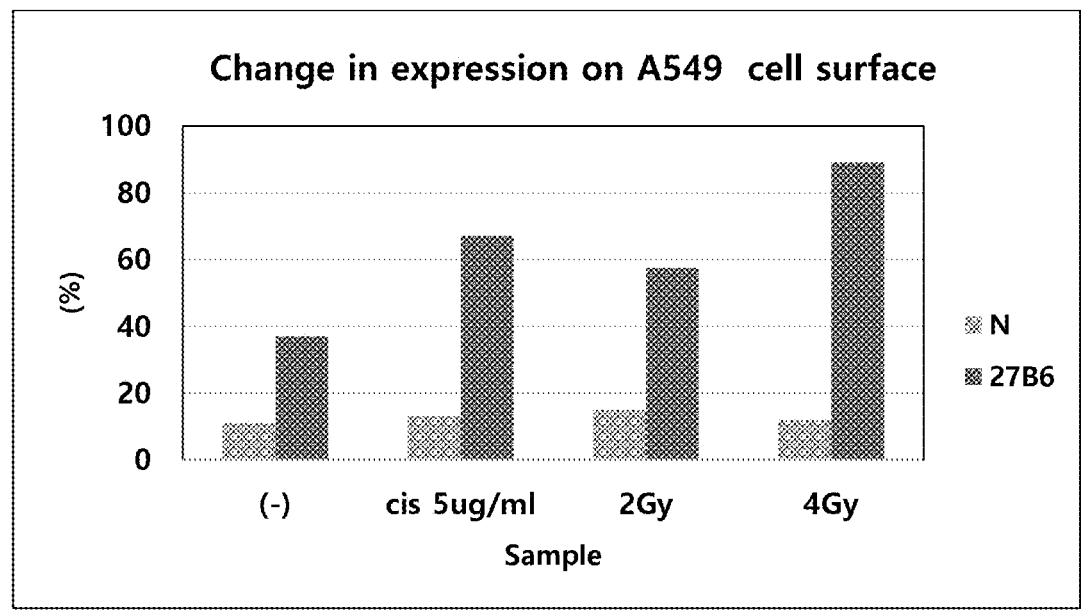
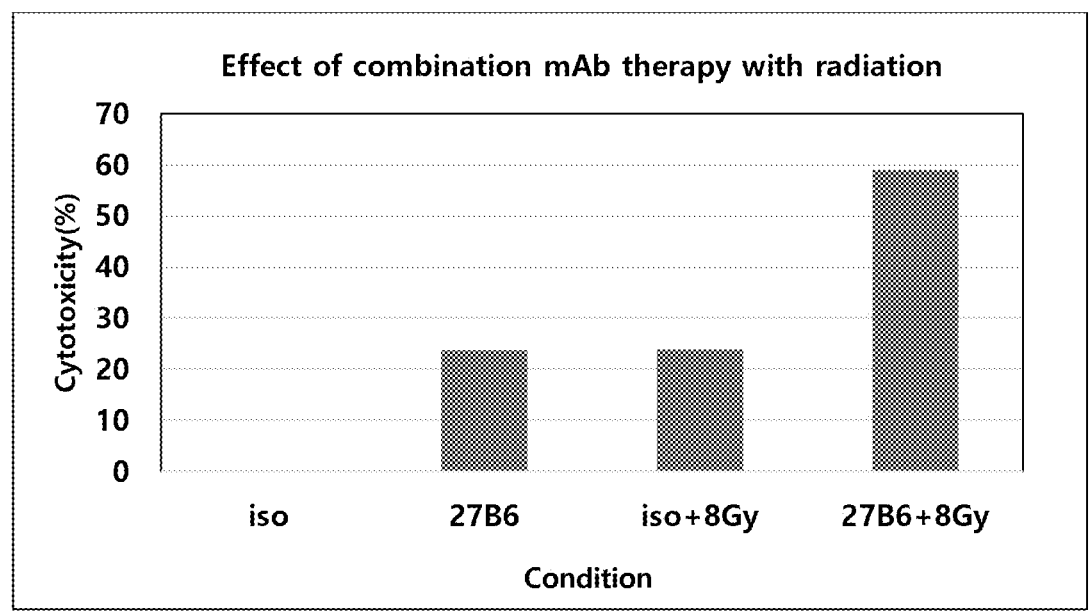

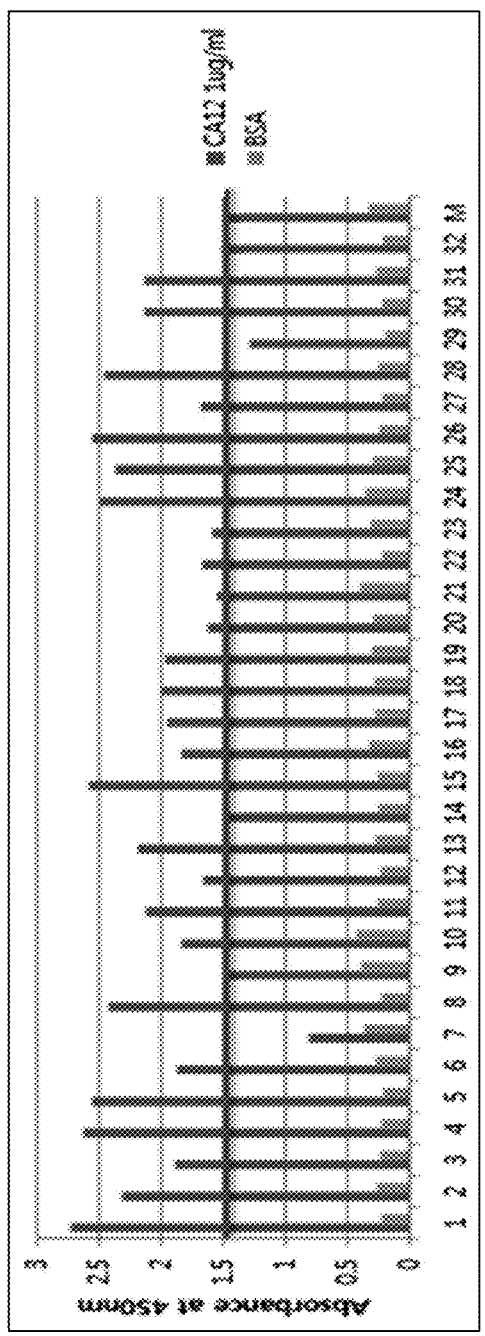
[Fig. 21]

[Fig. 22]

[Fig. 23]
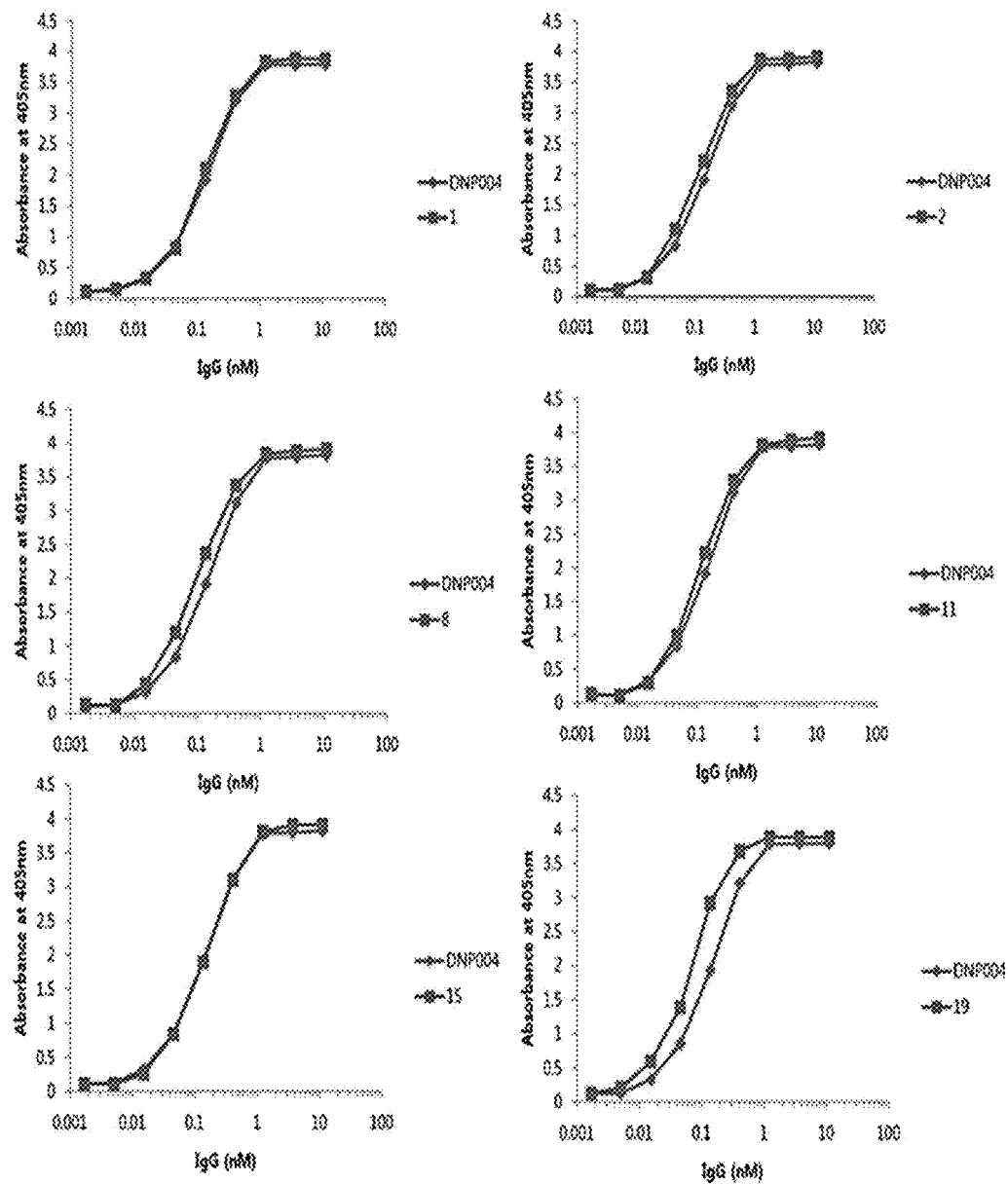

[Fig. 24]
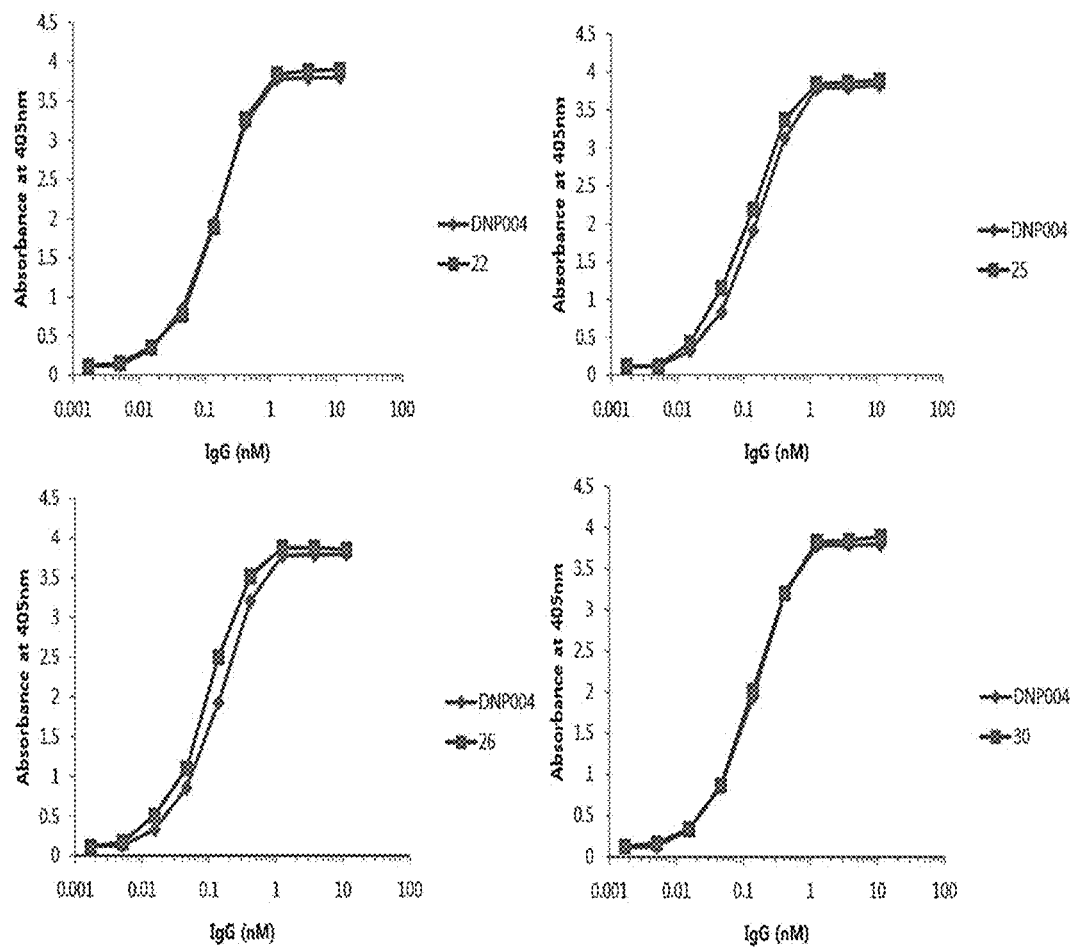

[Fig. 25]
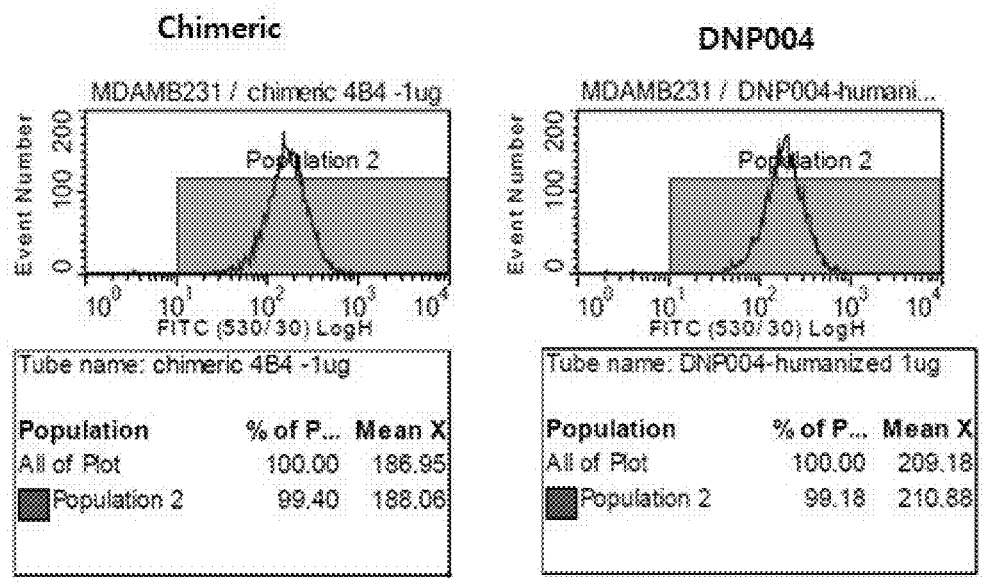
[Fig. 26]
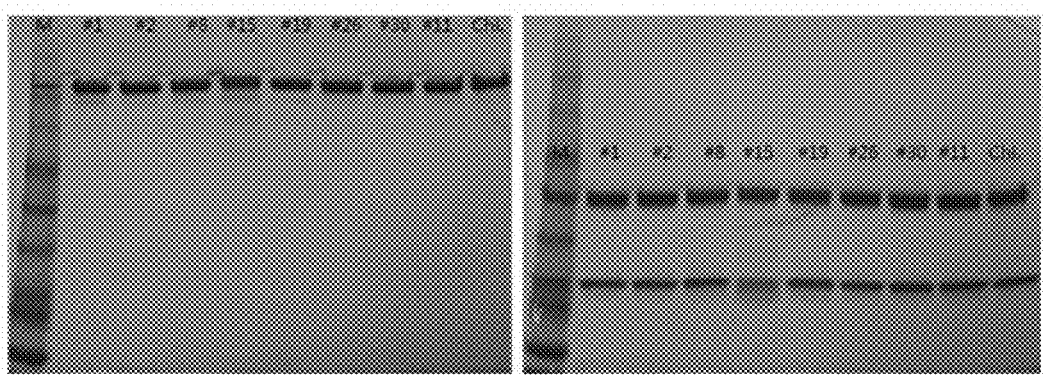

[Fig. 27]
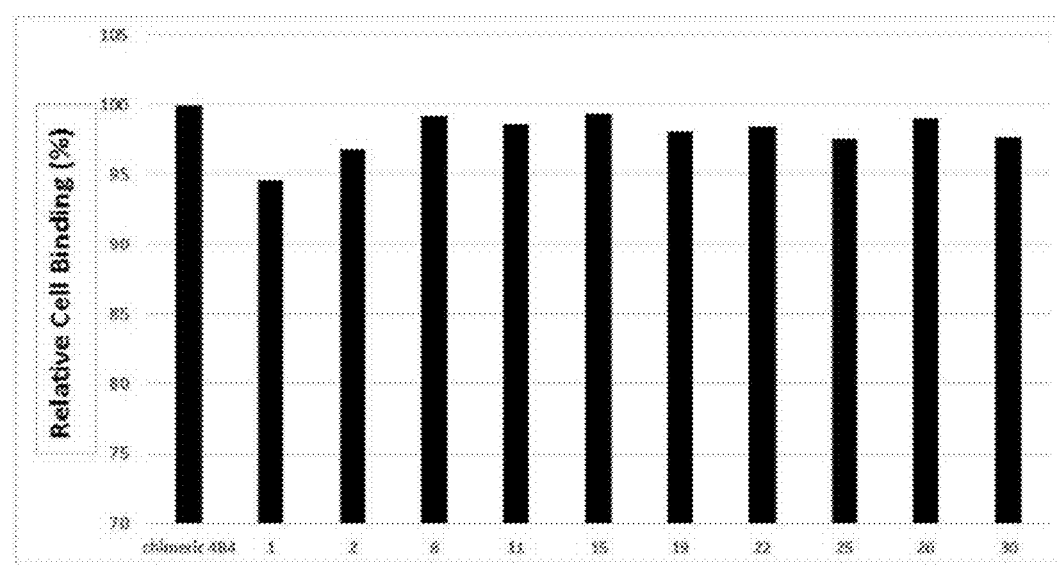

[Fig. 28]
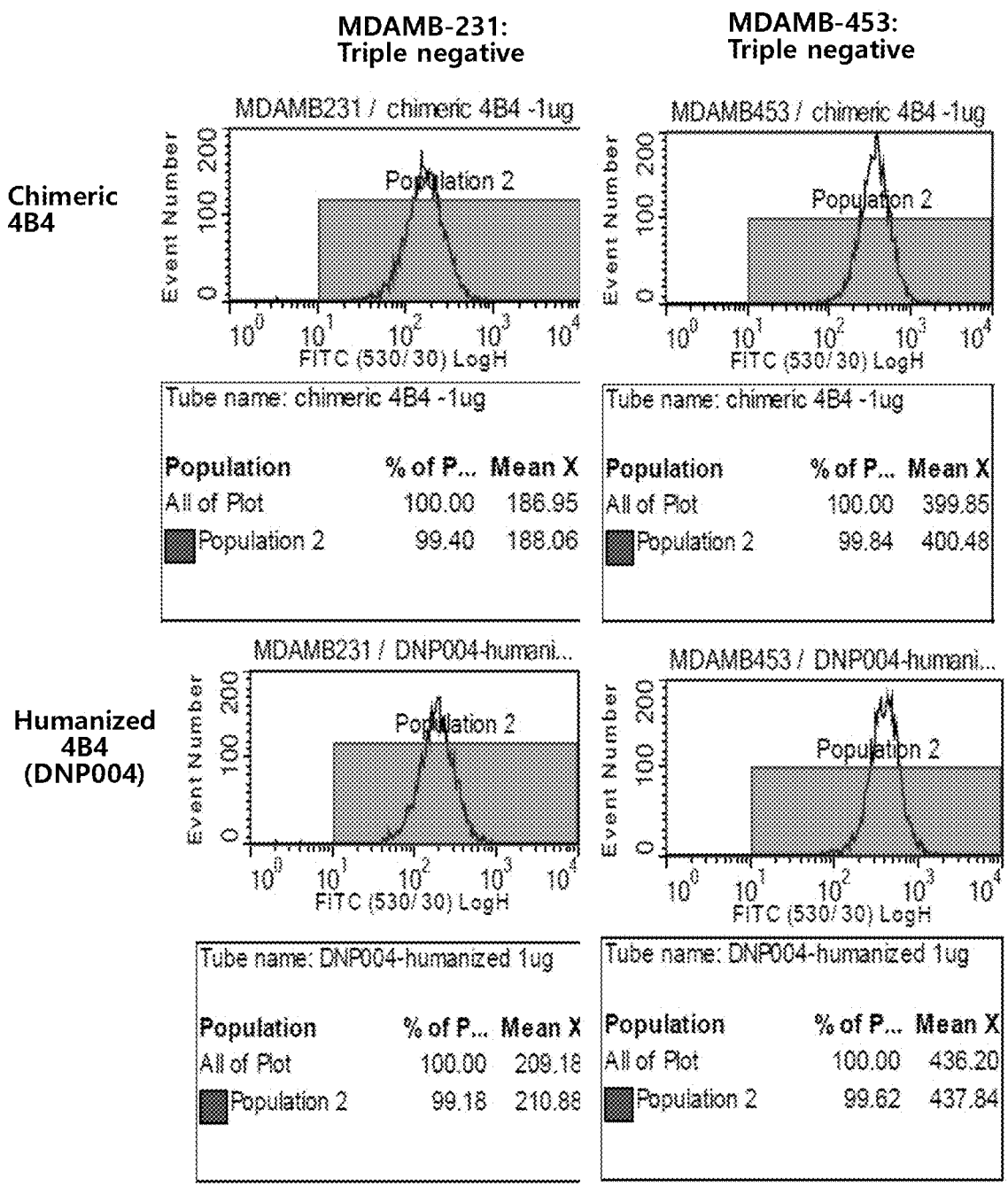

[Fig. 29]
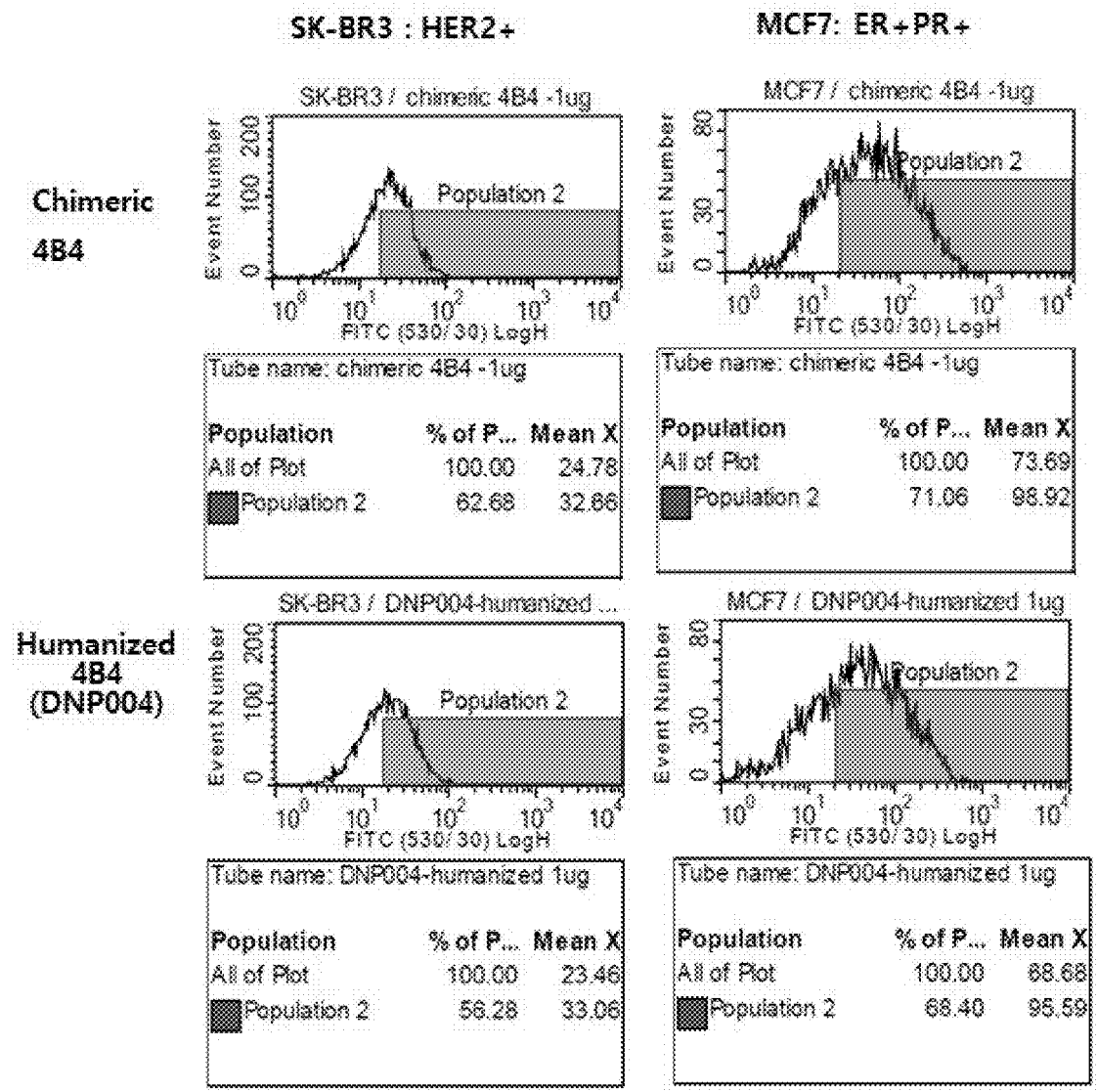
ER: Estrogen receptor
PR: Progesteron Receptor
HER2: Human Epidermal Growth Factor Receptor2

[Fig. 30]
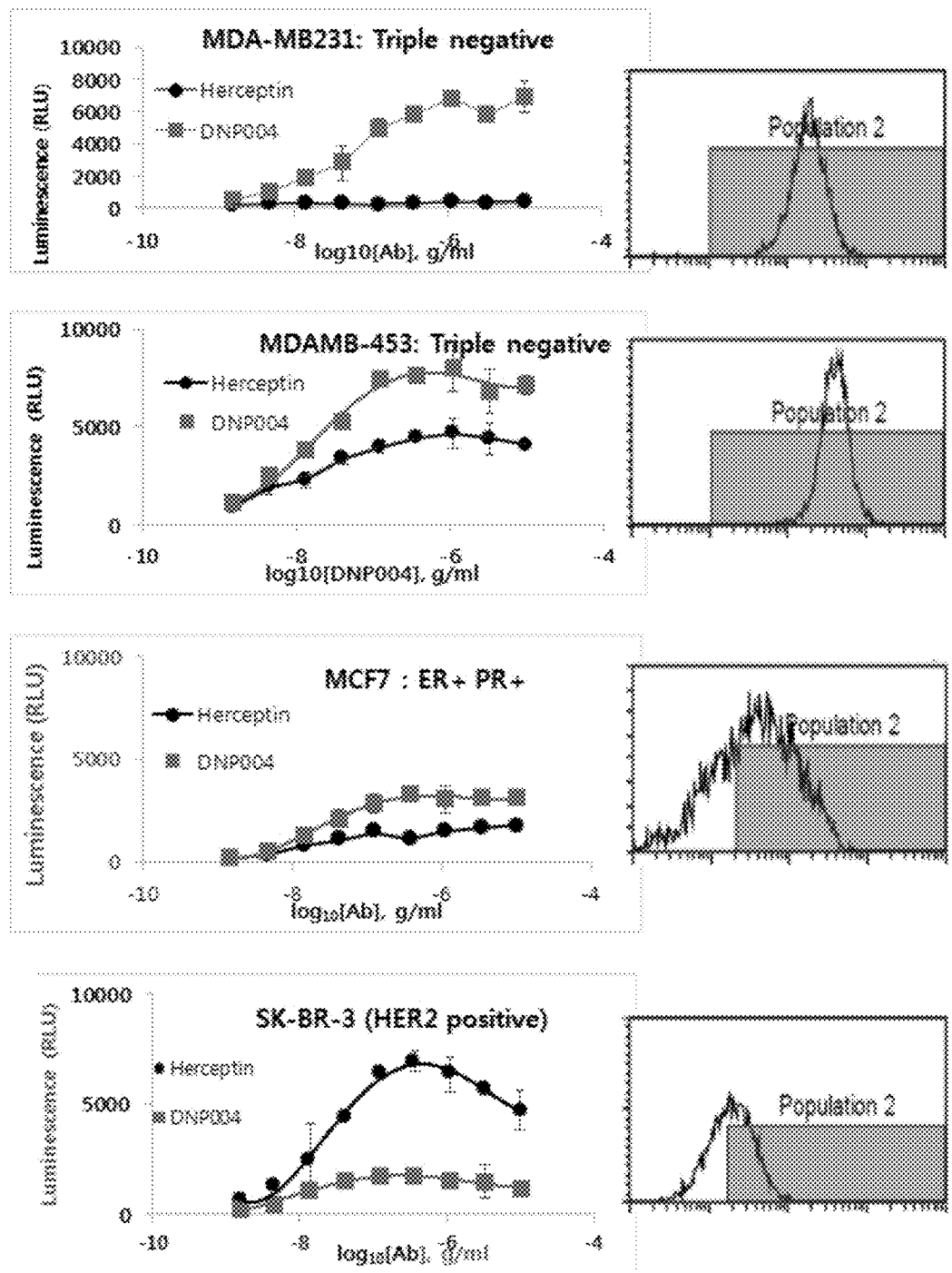

[Fig. 31]
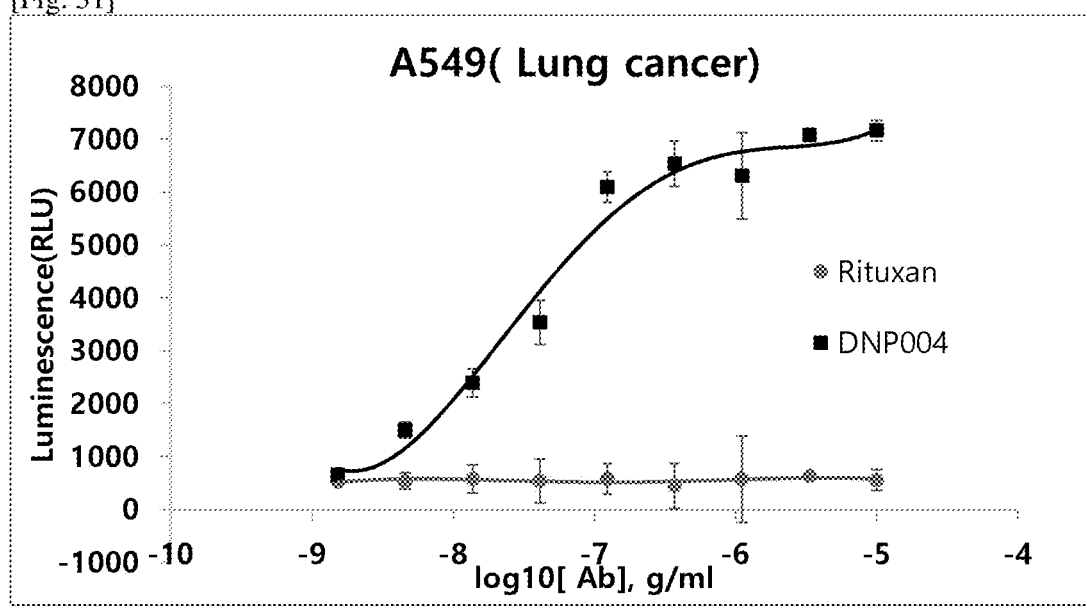

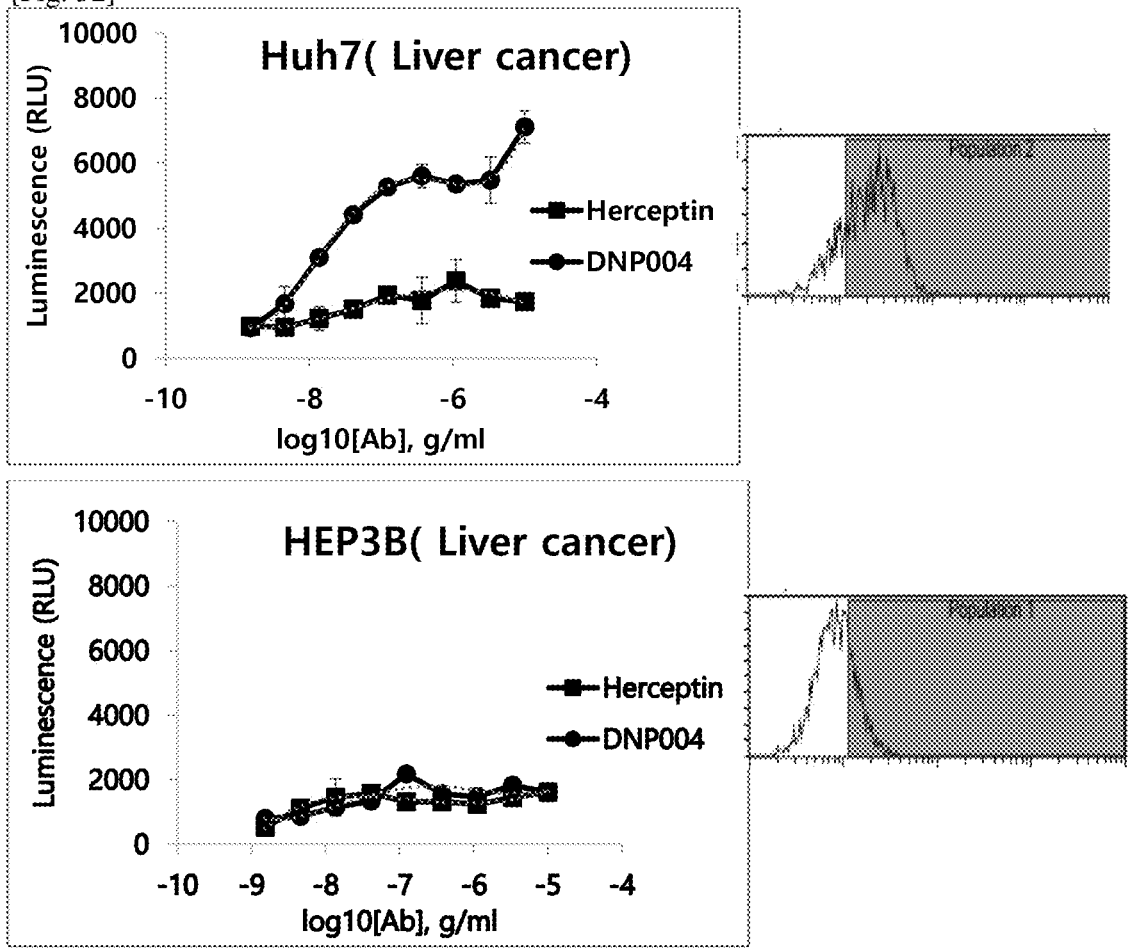
[Fig. 32]

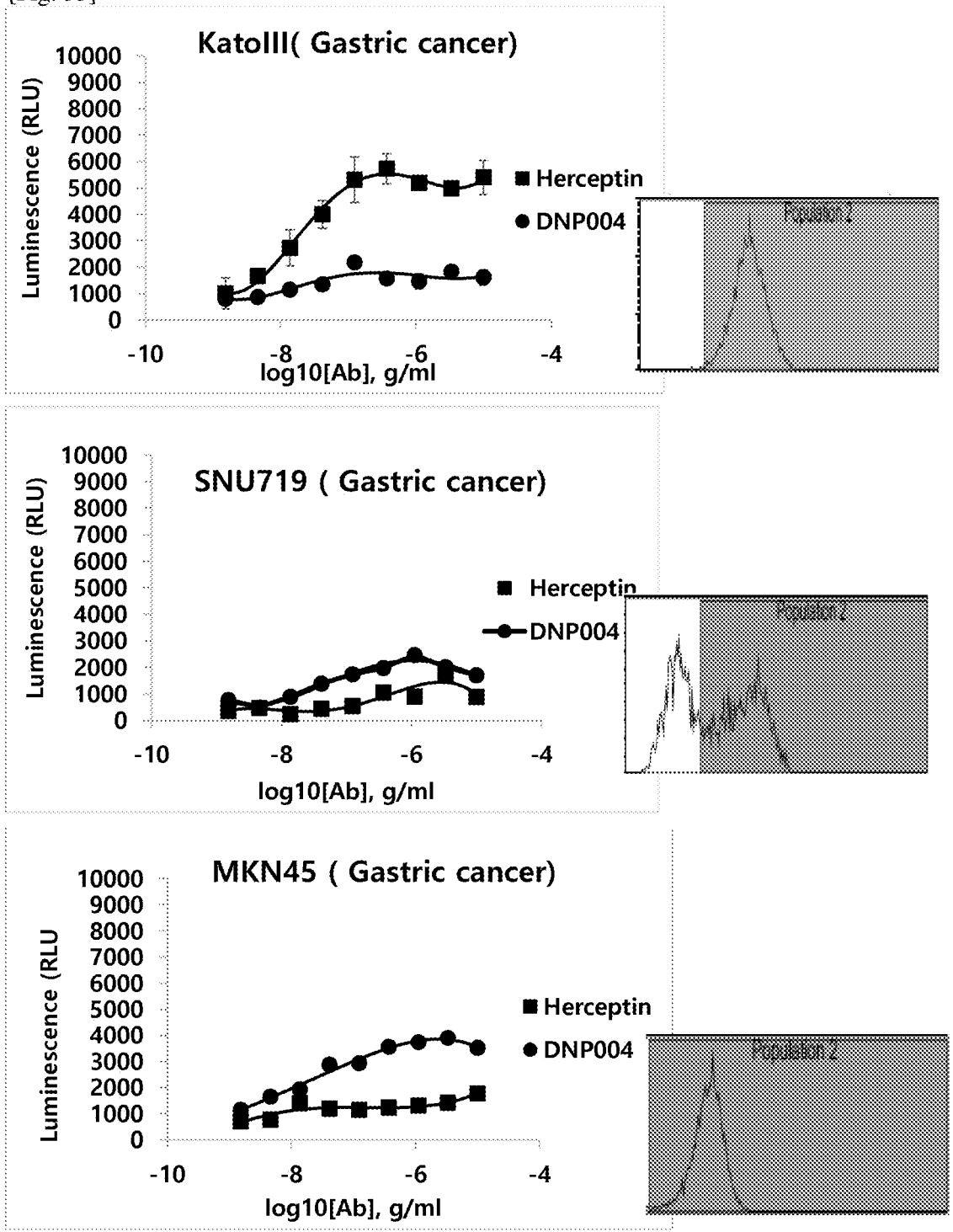
[Fig. 33]

[Fig. 34]
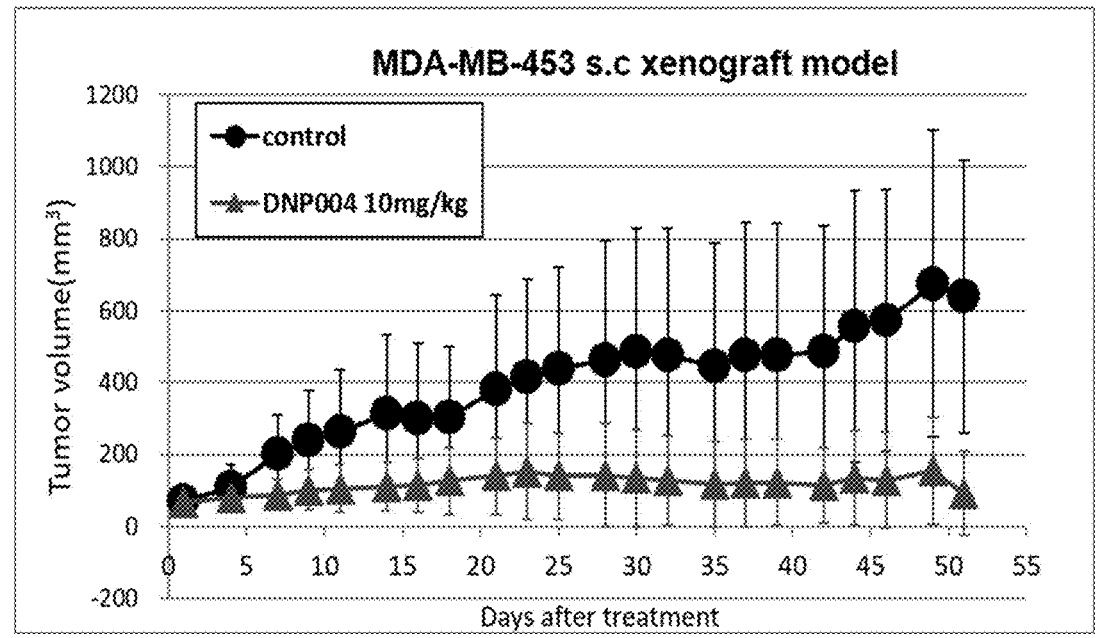
[Fig. 35]
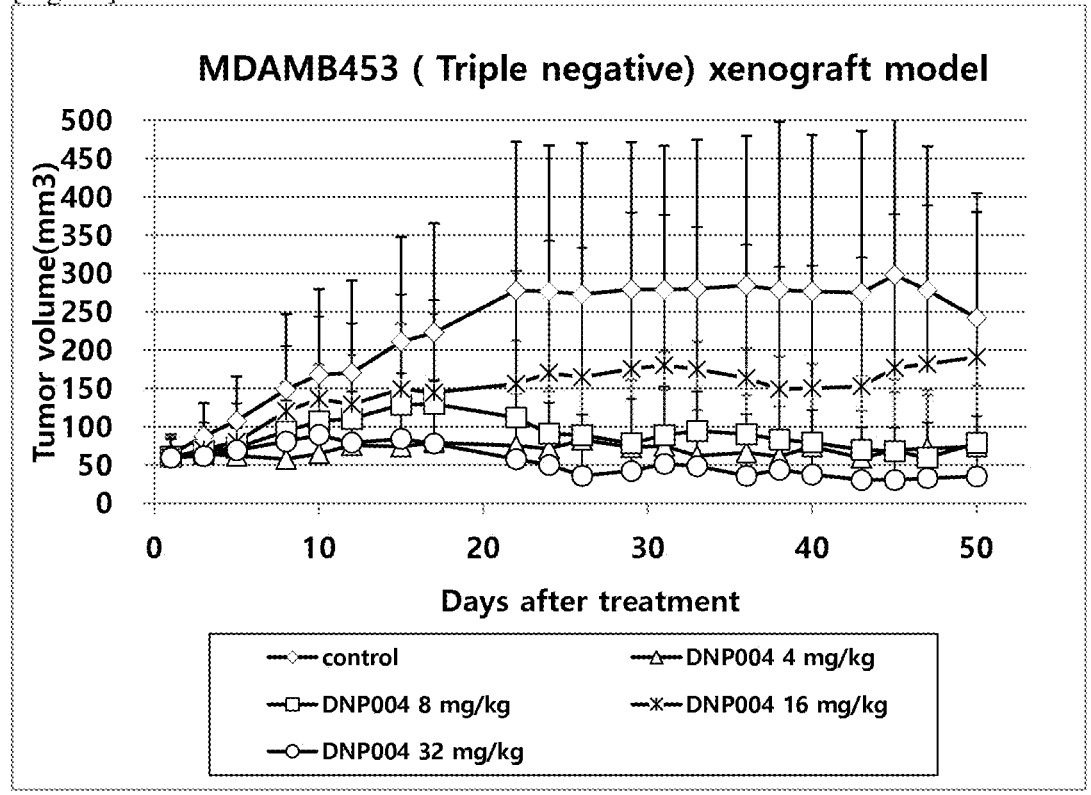

[Fig. 36]
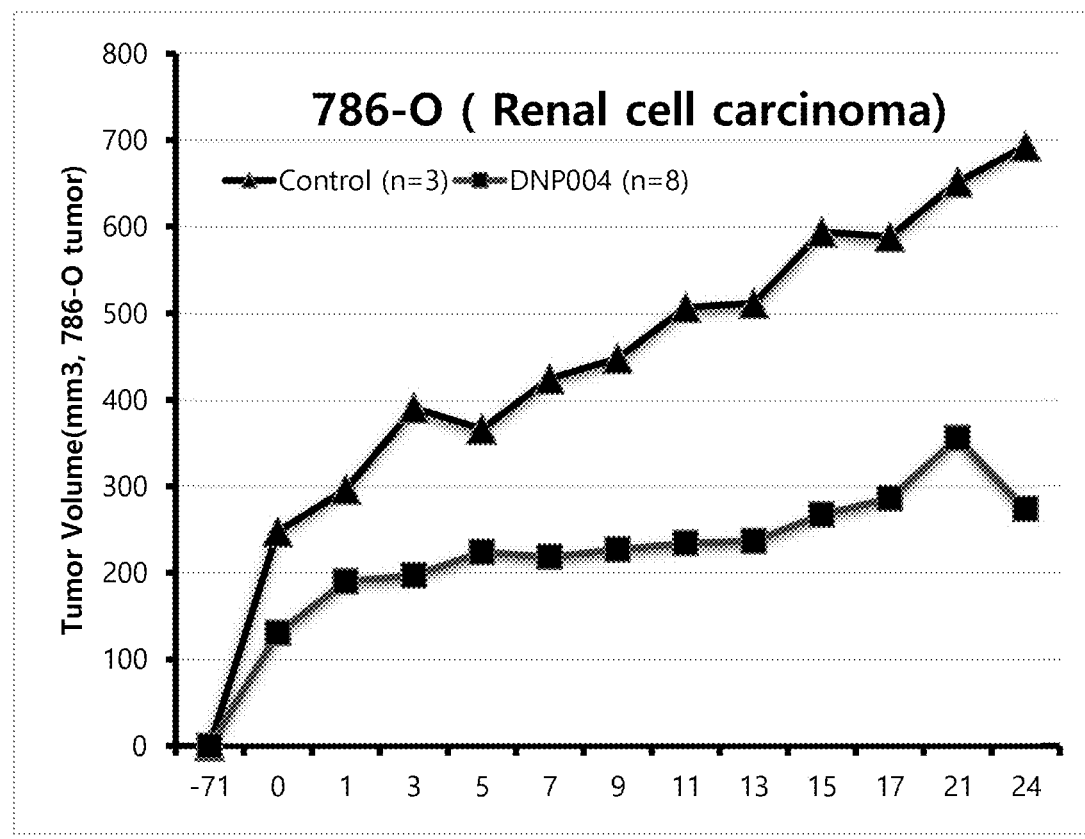

[Fig. 37]
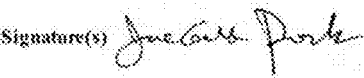

[Fig. 38]
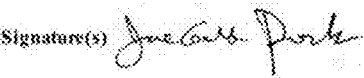

SEQUENCE LISTING

<160> NUMBER OF SEQ ID NOS: 63

<210> SEQ ID NO 1
<211> LENGTH: 7
<212> TYPE: PRT
<213> ORGANISM: Artificial Sequence
<220> FEATURE:
<223> OTHER INFORMATION: epitope of humanized 27B6

<400> SEQUENCE: 1

Trp Thr Tyr Phe Gly Pro Asp
1               5

<210> SEQ ID NO 2
<211> LENGTH: 14
<212> TYPE: PRT
<213> ORGANISM: Artificial Sequence
<220> FEATURE:

```
<223> OTHER INFORMATION: epitope of humanized 27B6

<400> SEQUENCE: 2

Ala Pro Val Asn Gly Ser Lys Trp Thr Tyr Phe Gly Pro Asp
1               5                   10

<210> SEQ ID NO 3
<211> LENGTH: 14
<212> TYPE: PRT
<213> ORGANISM: Artificial Sequence
<220> FEATURE:
<223> OTHER INFORMATION: epitope of humanized 4B4

<400> SEQUENCE: 3

Gly Glu Asn Ser Trp Ser Lys Lys Tyr Pro Ser Cys Gly Gly
1               5                   10

<210> SEQ ID NO 4
<211> LENGTH: 19
<212> TYPE: PRT
<213> ORGANISM: Artificial Sequence
<220> FEATURE:
<223> OTHER INFORMATION: epitope of humanized 4B4

<400> SEQUENCE: 4

Gly Glu Asn Ser Trp Ser Lys Lys Tyr Pro Ser Cys Gly Gly Leu
1               5                   10                  15

Gln Ser Pro

<210> SEQ ID NO 5
<211> LENGTH: 354
<212> TYPE: PRT
<213> ORGANISM: Artificial Sequence
<220> FEATURE:
<223> OTHER INFORMATION: Amino acid sequence of CA XII derived from
      human

<400> SEQUENCE: 5

Met Pro Arg Arg Ser Leu His Ala Ala Ala Val Leu Leu Leu Val Ile
1               5                   10                  15

Leu Lys Glu Gln Pro Ser Ser Pro Ala Pro Val Asn Gly Ser Lys Trp
                20                  25                  30

Thr Tyr Phe Gly Pro Asp Gly Glu Asn Ser Trp Ser Lys Lys Tyr Pro
            35                  40                  45

Ser Cys Gly Gly Leu Leu Gln Ser Pro Ile Asp Leu His Ser Asp Ile
        50                  55                  60

Leu Gln Tyr Asp Ala Ser Leu Thr Pro Leu Glu Phe Gln Gly Tyr Asn
65                  70                  75                  80

Leu Ser Ala Asn Lys Gln Phe Leu Leu Thr Asn Asn Gly His Ser Val
                85                  90                  95

Lys Leu Asn Leu Pro Ser Asp Met His Ile Gln Gly Leu Gln Ser Arg
            100                 105                 110

Tyr Ser Ala Thr Gln Leu His Leu His Trp Gly Asn Pro Asn Asp Pro
        115                 120                 125

His Gly Ser Glu His Thr Val Ser Gly Gln His Phe Ala Ala Glu Leu
    130                 135                 140

His Ile Val His Tyr Asn Ser Asp Leu Tyr Pro Asp Ala Ser Thr Ala
145                 150                 155                 160

Ser Asn Lys Ser Glu Gly Leu Ala Val Leu Ala Val Leu Ile Glu Met
                165                 170                 175
```

```
Gly Ser Phe Asn Pro Ser Tyr Asp Lys Ile Phe Ser His Leu Gln His
            180                 185                 190

Val Lys Tyr Lys Gly Gln Glu Ala Phe Val Pro Gly Phe Asn Ile Glu
        195                 200                 205

Glu Leu Leu Pro Glu Arg Thr Ala Glu Tyr Tyr Arg Tyr Arg Gly Ser
    210                 215                 220

Leu Thr Thr Pro Pro Cys Asn Pro Thr Val Leu Trp Thr Val Phe Arg
225                 230                 235                 240

Asn Pro Val Gln Ile Ser Gln Glu Gln Leu Leu Ala Leu Glu Thr Ala
                245                 250                 255

Leu Tyr Cys Thr His Met Asp Asp Pro Ser Pro Arg Glu Met Ile Asn
            260                 265                 270

Asn Phe Arg Gln Val Gln Lys Phe Asp Glu Arg Leu Val Tyr Thr Ser
        275                 280                 285

Phe Ser Gln Val Gln Val Cys Thr Ala Ala Gly Leu Ser Leu Gly Ile
    290                 295                 300

Ile Leu Ser Leu Ala Leu Ala Gly Ile Leu Gly Ile Cys Ile Val Val
305                 310                 315                 320

Val Val Ser Ile Trp Leu Phe Arg Arg Lys Ser Ile Lys Lys Gly Asp
                325                 330                 335

Asn Lys Gly Val Ile Tyr Lys Pro Ala Thr Lys Met Glu Thr Glu Ala
            340                 345                 350

His Ala

<210> SEQ ID NO 6
<211> LENGTH: 8
<212> TYPE: PRT
<213> ORGANISM: Artificial Sequence
<220> FEATURE:
<223> OTHER INFORMATION: VH-CDR1 of 27B6 antibody

<400> SEQUENCE: 6

Gly Tyr Ser Phe Thr Asn Tyr Trp
1               5

<210> SEQ ID NO 7
<211> LENGTH: 8
<212> TYPE: PRT
<213> ORGANISM: Artificial Sequence
<220> FEATURE:
<223> OTHER INFORMATION: VH-CDR2 of 27B6 antibody

<400> SEQUENCE: 7

Ile Asp Pro Ser Asp Ser Glu Thr
1               5

<210> SEQ ID NO 8
<211> LENGTH: 13
<212> TYPE: PRT
<213> ORGANISM: Artificial Sequence
<220> FEATURE:
<223> OTHER INFORMATION: VH-CDR3 of 27B6 antibody

<400> SEQUENCE: 8

Thr Arg Gly Ile Arg Gly Gly Tyr Tyr Ala Met Asp Tyr
1               5                   10

<210> SEQ ID NO 9
<211> LENGTH: 6
<212> TYPE: PRT
<213> ORGANISM: Artificial Sequence
```

```
<220> FEATURE:
<223> OTHER INFORMATION: VL-CDR1 of 27B6 antibody

<400> SEQUENCE: 9

Gln Asp Ile Ser Asn Tyr
1               5

<210> SEQ ID NO 10
<211> LENGTH: 3
<212> TYPE: PRT
<213> ORGANISM: Artificial Sequence
<220> FEATURE:
<223> OTHER INFORMATION: VH-CDR2 of 27B6 antibody

<400> SEQUENCE: 10

Tyr Thr Ser
1

<210> SEQ ID NO 11
<211> LENGTH: 9
<212> TYPE: PRT
<213> ORGANISM: Artificial Sequence
<220> FEATURE:
<223> OTHER INFORMATION: VH-CDR3 of 27B6 antibody

<400> SEQUENCE: 11

Gln Gln Gly Asp Thr Leu Pro Arg Thr
1               5

<210> SEQ ID NO 12
<211> LENGTH: 120
<212> TYPE: PRT
<213> ORGANISM: Artificial Sequence
<220> FEATURE:
<223> OTHER INFORMATION: Heavy chain variable region of 27B6 antibody

<400> SEQUENCE: 12

Gln Val Gln Leu Gln Gln Ser Gly Pro Gln Leu Val Trp Pro Gly Ala
1               5                   10                  15

Ser Val Lys Ile Ser Cys Asn Thr Ser Gly Tyr Ser Phe Thr Asn Tyr
                20                  25                  30

Trp Ile His Trp Val Lys Gln Arg Pro Gly Gln Gly Leu Glu Trp Ile
            35                  40                  45

Gly Met Ile Asp Pro Ser Asp Ser Glu Thr Arg Leu Asn Gln Lys Phe
        50                  55                  60

Lys Asp Lys Thr Thr Leu Thr Val Asp Arg Ser Ser Thr Ala Tyr
65                  70                  75                  80

Met Gln Val Ser Ser Thr Ser Glu Asp Ser Ala Val Tyr Tyr Cys
                85                  90                  95

Thr Arg Gly Ile Arg Gly Gly Tyr Tyr Ala Met Asp Tyr Trp Gly Gln
            100                 105                 110

Gly Thr Ser Val Thr Val Ser Ser
        115                 120

<210> SEQ ID NO 13
<211> LENGTH: 107
<212> TYPE: PRT
<213> ORGANISM: Artificial Sequence
<220> FEATURE:
<223> OTHER INFORMATION: Light chain variable region of 27B6 antibody

<400> SEQUENCE: 13

Asp Ile Gln Met Thr Gln Thr Thr Ser Ser Leu Ser Ala Ser Leu Gly
```

```
                1               5                  10                  15
Asp Arg Val Thr Ile Ser Cys Arg Ala Ser Gln Asp Ile Ser Asn Tyr
                20                  25                  30

Leu Asn Trp Tyr Gln Gln Lys Pro Glu Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Arg
                85                  90                  95

Thr Phe Gly Glu Gly Thr Lys Leu Glu Ile Arg
                100                 105
```

<210> SEQ ID NO 14
<211> LENGTH: 8
<212> TYPE: PRT
<213> ORGANISM: Artificial Sequence
<220> FEATURE:
<223> OTHER INFORMATION: VH-CDR1 of 4B4 antibody

<400> SEQUENCE: 14

```
Gly Tyr Ser Tyr Thr Asp Tyr Asn
1               5
```

<210> SEQ ID NO 15
<211> LENGTH: 8
<212> TYPE: PRT
<213> ORGANISM: Artificial Sequence
<220> FEATURE:
<223> OTHER INFORMATION: VH-CDR2 of 4B4 antibody

<400> SEQUENCE: 15

```
Ile Asp Pro Ala Asn Gly Asp Thr
1               5
```

<210> SEQ ID NO 16
<211> LENGTH: 14
<212> TYPE: PRT
<213> ORGANISM: Artificial Sequence
<220> FEATURE:
<223> OTHER INFORMATION: VH-CDR3 of 4B4 antibody

<400> SEQUENCE: 16

```
Ala Arg Pro Ile Tyr Tyr Gly Val Tyr Trp Tyr Phe Asp Val
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: VL-CDR1 of 4B4 antibody

<400> SEQUENCE: 17

```
Lys Ser Leu Leu His Ser Asn Gly Asn Thr Tyr
1               5                   10
```

<210> SEQ ID NO 18
<211> LENGTH: 3
<212> TYPE: PRT
<213> ORGANISM: Artificial Sequence
<220> FEATURE:
<223> OTHER INFORMATION: VL-CDR2 of 4B4 antibody

<400> SEQUENCE: 18

Arg Met Ser
1

<210> SEQ ID NO 19
<211> LENGTH: 9
<212> TYPE: PRT
<213> ORGANISM: Artificial Sequence
<220> FEATURE:
<223> OTHER INFORMATION: VL-CDR3 of 4B4 antibody

<400> SEQUENCE: 19

Met Gln His Leu Glu Tyr Pro Phe Thr
1               5

<210> SEQ ID NO 20
<211> LENGTH: 120
<212> TYPE: PRT
<213> ORGANISM: Artificial Sequence
<220> FEATURE:
<223> OTHER INFORMATION: Heavy chain variable region of 4B4 antibody

<400> SEQUENCE: 20

Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Ser Tyr Thr Asp Tyr
            20                  25                  30

Asn Ile Tyr Trp Val Arg Gln Ser Gln Gly Lys Ser Leu Asp Trp Ile
        35                  40                  45

Gly Tyr Ile Asp Pro Ala Asn Gly Asp Thr Thr Tyr Asn Gln Lys Phe
    50                  55                  60

Lys Gly Lys Ala Thr Leu Thr Val Asp Lys Ser Ser Thr Ala Phe
65                  70                  75                  80

Met His Leu Asn Ser Leu Thr Ser Asp Gly Ser Ala Val Tyr Phe Cys
                85                  90                  95

Ala Arg Pro Ile Tyr Tyr Gly Val Tyr Trp Tyr Phe Asp Val Trp Gly
            100                 105                 110

Ala Gly Thr Thr Val Thr Val Ser
        115                 120

<210> SEQ ID NO 21
<211> LENGTH: 112
<212> TYPE: PRT
<213> ORGANISM: Artificial Sequence
<220> FEATURE:
<223> OTHER INFORMATION: Light chain variable region of 4B4 antibody

<400> SEQUENCE: 21

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His 85                  90                  95
Leu Glu Tyr Pro Phe Thr Phe Gly Ser Gly Thr Lys Leu Glu Ile Lys
            100                 105                 110

<210> SEQ ID NO 22
<211> LENGTH: 12
<212> TYPE: PRT
<213> ORGANISM: Artificial Sequence
<220> FEATURE:
<223> OTHER INFORMATION: Peptide derived from 27B6 ntibody

<400> SEQUENCE: 22

Gln Phe Leu Leu Thr Asn Asn Gly His Ser Val Lys
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Peptide derived from 27B6 ntibody

<400> SEQUENCE: 23

Trp Thr Tyr Phe Gly Pro Asp Gly Glu Asn Ser Trp Ser Lys
1               5                   10

<210> SEQ ID NO 24
<211> LENGTH: 18
<212> TYPE: PRT
<213> ORGANISM: Artificial Sequence
<220> FEATURE:
<223> OTHER INFORMATION: Peptide derived from 27B6 ntibody

<400> SEQUENCE: 24

Gly Gln Glu Ala Phe Val Pro Gly Phe Asn Ile Glu Glu Leu Leu Pro
1               5                   10                  15

Glu Arg

<210> SEQ ID NO 25
<211> LENGTH: 20
<212> TYPE: PRT
<213> ORGANISM: Artificial Sequence
<220> FEATURE:
<223> OTHER INFORMATION: Peptide derived from 27B6 ntibody

<400> SEQUENCE: 25

Tyr Lys Gly Gln Glu Ala Phe Val Pro Gly Phe Asn Ile Glu Glu Leu
1               5                   10                  15

Leu Pro Glu Arg
            20

<210> SEQ ID NO 26
<211> LENGTH: 7
<212> TYPE: PRT
<213> ORGANISM: Artificial Sequence
<220> FEATURE:
<223> OTHER INFORMATION: Peptide derived from 4B4 antibody

<400> SEQUENCE: 26

Glu Met Ile Asn Asn Phe Arg
1               5

<210> SEQ ID NO 27
<211> LENGTH: 9
<212> TYPE: PRT

<213> ORGANISM: Artificial Sequence
<220> FEATURE:
<223> OTHER INFORMATION: Peptide derived from 4B4 antibody

<400> SEQUENCE: 27

Gly Val Ile Tyr Lys Pro Ala Thr Lys
1               5

<210> SEQ ID NO 28
<211> LENGTH: 14
<212> TYPE: PRT
<213> ORGANISM: Artificial Sequence
<220> FEATURE:
<223> OTHER INFORMATION: VH-CDR3 of DNP004 antibody

<400> SEQUENCE: 28

Ser Arg Pro Ile Tyr Tyr Gly Ala Tyr Trp Tyr Phe Asp Val
1               5                   10

<210> SEQ ID NO 29
<211> LENGTH: 7
<212> TYPE: PRT
<213> ORGANISM: Artificial Sequence
<220> FEATURE:
<223> OTHER INFORMATION: VL-CDR1 of DNP004 antibody
<220> FEATURE:
<221> NAME/KEY: MISC_FEATURE
<222> LOCATION: (4)
<223> OTHER INFORMATION: X is P or S

<400> SEQUENCE: 29

Ala Ser Ser Xaa Val Thr Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: VL-CDR2 of DNP004 antibody
<220> FEATURE:
<221> NAME/KEY: MISC_FEATURE
<222> LOCATION: (1)
<223> OTHER INFORMATION: X is A, G or R
<220> FEATURE:
<221> NAME/KEY: MISC_FEATURE
<222> LOCATION: (4)
<223> OTHER INFORMATION: X is S, R, H, Q, D, E or M
<220> FEATURE:
<221> NAME/KEY: MISC_FEATURE
<222> LOCATION: (6)
<223> OTHER INFORMATION: X is A, V, I or M
<220> FEATURE:
<221> NAME/KEY: MISC_FEATURE
<222> LOCATION: (7)
<223> OTHER INFORMATION: X is P or S

<400> SEQUENCE: 30

Xaa Thr Ser Xaa Leu Xaa Xaa
1               5

<210> SEQ ID NO 31
<211> LENGTH: 9
<212> TYPE: PRT
<213> ORGANISM: Artificial Sequence
<220> FEATURE:
<223> OTHER INFORMATION: VL-CDR3 of DNP004 antibody

<400> SEQUENCE: 31

Gln Gln Trp Ser Ser Asn Pro Leu Thr

```
<210> SEQ ID NO 32
<211> LENGTH: 7
<212> TYPE: PRT
<213> ORGANISM: Artificial Sequence
<220> FEATURE:
<223> OTHER INFORMATION: VL-CDR1 of DNP004 antibody

<400> SEQUENCE: 32

Ala Ser Ser Pro Val Thr Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: VL-CDR1 of DNP004 antibody

<400> SEQUENCE: 33

Ala Ser Ser Ser Val Thr Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 34

Ala Thr Ser Ser Leu Ala Pro
1               5

<210> SEQ ID NO 35
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 35

Ala Thr Ser Ser Leu Val Ser
1               5

<210> SEQ ID NO 36
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 36

Gly Thr Ser Arg Leu Val Ser
1               5

<210> SEQ ID NO 37
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 37

Ala Thr Ser His Leu Val Ser
1               5
```

```
<210> SEQ ID NO 38
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 38

Gly Thr Ser Gln Leu Val Ser
1               5

<210> SEQ ID NO 39
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 39

Arg Thr Ser Asp Leu Ile Ser
1               5

<210> SEQ ID NO 40
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 40

Ala Thr Ser Glu Leu Met Ser
1               5

<210> SEQ ID NO 41
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 41

Gly Thr Ser Met Leu Ala Ser
1               5

<210> SEQ ID NO 42
<211> LENGTH: 7
<212> TYPE: PRT
<213> ORGANISM: Artificial Sequence
<220> FEATURE:
<223> OTHER INFORMATION: VL-CDR2 of DNP004 antibody

<400> SEQUENCE: 42

Ala Thr Ser Ser Leu Ala Ser
1               5

<210> SEQ ID NO 43
<211> LENGTH: 25
<212> TYPE: PRT
<213> ORGANISM: Artificial Sequence
<220> FEATURE:
<223> OTHER INFORMATION: Frame work #1 of VH-humanized

<400> SEQUENCE: 43

Glu Val Gln Leu Val Glu Ser Gly Gly Gly Leu Val Gln Pro Gly Gly
1               5                   10                  15
```

Ser Leu Arg Leu Ser Cys Ala Ala Ser
            20                  25

<210> SEQ ID NO 44
<211> LENGTH: 17
<212> TYPE: PRT
<213> ORGANISM: Artificial Sequence
<220> FEATURE:
<223> OTHER INFORMATION: Frame work #2 of VH-humanized

<400> SEQUENCE: 44

Ile Tyr Trp Val Arg Gln Ala Pro Gly Lys Gly Leu Glu Trp Val Gly
1               5                   10                  15

Tyr

<210> SEQ ID NO 45
<211> LENGTH: 38
<212> TYPE: PRT
<213> ORGANISM: Artificial Sequence
<220> FEATURE:
<223> OTHER INFORMATION: Frame work #3 of VH-humanized

<400> SEQUENCE: 45

Thr Tyr Asn Gln Lys Phe Lys Gly Arg Ala Thr Ile Ser Val Asp Lys
1               5                   10                  15

Ser Lys Asn Thr Ala Tyr Leu Gln Met Asn Ser Leu Arg Ala Glu Asp
            20                  25                  30

Thr Ala Val Tyr Tyr Cys
        35

<210> SEQ ID NO 46
<211> LENGTH: 11
<212> TYPE: PRT
<213> ORGANISM: Artificial Sequence
<220> FEATURE:
<223> OTHER INFORMATION: Frame work #4 of VH-humanized

<400> SEQUENCE: 46

Trp Gly Gln Gly Thr Leu Val Thr Val Ser Ser
1               5                   10

<210> SEQ ID NO 47
<211> LENGTH: 24
<212> TYPE: PRT
<213> ORGANISM: Artificial Sequence
<220> FEATURE:
<223> OTHER INFORMATION: Frame work #1 of VL-humanized

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg
            20

<210> SEQ ID NO 48
<211> LENGTH: 17
<212> TYPE: PRT
<213> ORGANISM: Artificial Sequence
<220> FEATURE:
<223> OTHER INFORMATION: Frame work #2 of VL-humanized
<220> FEATURE:
<221> NAME/KEY: MISC_FEATURE
<222> LOCATION: (5)
<223> OTHER INFORMATION: X is Q or H
<220> FEATURE:
<221> NAME/KEY: MISC_FEATURE
<222> LOCATION: (13)
<223> OTHER INFORMATION: X is R or K

<400> SEQUENCE: 48

Met His Trp Tyr Xaa Gln Lys Pro Gly Lys Ala Pro Xaa Pro Trp Ile
1               5                   10                  15

Tyr

<210> SEQ ID NO 49
<211> LENGTH: 17
<212> TYPE: PRT
<213> ORGANISM: Artificial Sequence
<220> FEATURE:
<223> OTHER INFORMATION: Frame work #2 of VL-humanized

<400> SEQUENCE: 49

Met His Trp Tyr Gln Gln Lys Pro Gly Lys Ala Pro Arg Pro Trp Ile
1               5                   10                  15

Tyr

<210> SEQ ID NO 50
<211> LENGTH: 17
<212> TYPE: PRT
<213> ORGANISM: Artificial Sequence
<220> FEATURE:
<223> OTHER INFORMATION: Frame work #2 of VL-humanized

<400> SEQUENCE: 50

Met His Trp Tyr His Gln Lys Pro Gly Lys Ala Pro Lys Pro Trp Ile
1               5                   10                  15

Tyr

<210> SEQ ID NO 51
<211> LENGTH: 32
<212> TYPE: PRT
<213> ORGANISM: Artificial Sequence
<220> FEATURE:
<223> OTHER INFORMATION: Frame work #3 of VL-humanized

<400> SEQUENCE: 51

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 52
<211> LENGTH: 10
<212> TYPE: PRT
<213> ORGANISM: Artificial Sequence
<220> FEATURE:
<223> OTHER INFORMATION: Frame work #4 of VL-humanized

<400> SEQUENCE: 52

Phe Gly Gln Gly Thr Lys Val Glu Ile Lys
1               5                   10

<210> SEQ ID NO 53
<211> LENGTH: 121
<212> TYPE: PRT
<213> ORGANISM: Artificial Sequence
<220> FEATURE:
<223> OTHER INFORMATION: Heavy chain variable region of DNP004 antibody

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Tyr Thr Asp Tyr
            20                  25                  30

Asn Ile Tyr Trp Val Arg Gln Ala Pro Gly Lys Gly Leu Glu Trp Val
        35                  40                  45

Gly Tyr Ile Asp Pro Ala Asn Gly Asp Thr Thr Tyr Asn Gln Lys Phe
    50                  55                  60

Lys Gly Arg Ala Thr Ile Ser Val Asp Lys Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Pro Ile Tyr Tyr Gly Ala Tyr Trp Tyr Phe Asp Val Trp Gly
            100                 105                 110

Gln Gly Thr Leu Val Thr Val Ser Ser
            115                 120
```

```
<210> SEQ ID NO 54
<211> LENGTH: 106
<212> TYPE: PRT
<213> ORGANISM: Artificial Sequence
<220> FEATURE:
<223> OTHER INFORMATION: #1 Light chain variable region of DNP004
      antibody

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Pro Val Thr Tyr Met
            20                  25                  30

His Trp Tyr Gln Gln Lys Pro Gly Lys Ala Pro Lys Pro Trp Ile Tyr
        35                  40                  45

Ala Thr Ser Ser Leu Ala Pro Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105
```

```
<210> SEQ ID NO 55
<211> LENGTH: 106
<212> TYPE: PRT
<213> ORGANISM: Artificial Sequence
<220> FEATURE:
<223> OTHER INFORMATION: #2 Light chain variable region of DNP004
      antibody

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Thr Tyr Met
            20                  25                  30

His Trp Tyr Gln Gln Lys Pro Gly Lys Ala Pro Lys Pro Trp Ile Tyr
        35                  40                  45

Ala Thr Ser Ser Leu Val Ser Gly Val Pro Ser Arg Phe Ser Gly Ser
    50                  55                  60
```

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 56
<211> LENGTH: 106
<212> TYPE: PRT
<213> ORGANISM: Artificial Sequence
<220> FEATURE:
<223> OTHER INFORMATION: #8 Light chain variable region of DNP004
      antibody

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Thr Tyr Met
                20                  25                  30

His Trp Tyr Gln Gln Lys Pro Gly Lys Ala Pro Lys Pro Trp Ile Tyr
            35                  40                  45

Gly Thr Ser Arg Leu Val Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 57
<211> LENGTH: 106
<212> TYPE: PRT
<213> ORGANISM: Artificial Sequence
<220> FEATURE:
<223> OTHER INFORMATION: #11 Light chain variable region of DNP004
      antibody

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Thr Tyr Met
                20                  25                  30

His Trp Tyr Gln Gln Lys Pro Gly Lys Ala Pro Lys Pro Trp Ile Tyr
            35                  40                  45

Ala Thr Ser His Leu Val Ser Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 58
<211> LENGTH: 106
<212> TYPE: PRT
<213> ORGANISM: Artificial Sequence
<220> FEATURE:

<223> OTHER INFORMATION: #15 Light chain variable region of DNP004
antibody

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Thr Tyr Met
            20                  25                  30

His Trp Tyr Gln Gln Lys Pro Gly Lys Ala Pro Lys Pro Trp Ile Tyr
        35                  40                  45

Gly Thr Ser Gln Leu Val Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 59
<211> LENGTH: 106
<212> TYPE: PRT
<213> ORGANISM: Artificial Sequence
<220> FEATURE:
<223> OTHER INFORMATION: #19 Light chain variable region of DNP004
antibody

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Thr Tyr Met
            20                  25                  30

His Trp Tyr Gln Gln Lys Pro Gly Lys Ala Pro Lys Pro Trp Ile Tyr
        35                  40                  45

Arg Thr Ser Asp Leu Ile Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105

<210> SEQ ID NO 60
<211> LENGTH: 106
<212> TYPE: PRT
<213> ORGANISM: Artificial Sequence
<220> FEATURE:
<223> OTHER INFORMATION: #22 Light chain variable region of DNP004
antibody

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Thr Tyr Met
            20                  25                  30

His Trp Tyr Gln Gln Lys Pro Gly Lys Ala Pro Lys Pro Trp Ile Tyr
        35                  40                  45

Ala Thr Ser Glu Leu Met Ser Gly Val Pro Ser Arg Phe Ser Gly Ser

```
                    50                  55                  60
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                    85                  90                  95

Phe Gly Gln Gly Thr Lys Val Glu Ile Lys
                100                 105

<210> SEQ ID NO 61
<211> LENGTH: 106
<212> TYPE: PRT
<213> ORGANISM: Artificial Sequence
<220> FEATURE:
<223> OTHER INFORMATION: #25 Light chain variable region of  DNP004
      antibody

<400> SEQUENCE: 61

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Ser Val Thr Tyr Met
                20                  25                  30

His Trp Tyr Gln Gln Lys Pro Gly Lys Ala Pro Lys Pro Trp Ile Tyr
                35                  40                  45

Gly Thr Ser Met Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 62
<211> LENGTH: 106
<212> TYPE: PRT
<213> ORGANISM: Artificial Sequence
<220> FEATURE:
<223> OTHER INFORMATION: #26 Light chain variable region of  DNP004
      antibody

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Pro Val Thr Tyr Met
                20                  25                  30

His Trp Tyr Gln Gln Lys Pro Gly Lys Ala Pro Arg Pro Trp Ile Tyr
                35                  40                  45

Ala Thr Ser Ser Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
                100                 105

<210> SEQ ID NO 63
<211> LENGTH: 106
<212> TYPE: PRT
```

-continued

```
<213> ORGANISM: Artificial Sequence
<220> FEATURE:
<223> OTHER INFORMATION: #30 Light chain variable region of DNP004
      antibody

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Thr Tyr Met
            20                  25                  30

His Trp Tyr His Gln Lys Pro Gly Lys Ala Pro Lys Pro Trp Ile Tyr
        35                  40                  45

Ala Thr Ser Ser Leu Val Ser Gly Val Pro Ser Arg Phe Ser Gly Ser
    50                  55                  60

Gly Ser Gly Thr Asp Phe Thr Leu Thr Ile Ser Ser Leu Gln Pro Glu
65              70                  75                  80

Asp Phe Ala Thr Tyr Tyr Cys Gln Gln Trp Ser Ser Asn Pro Leu Thr
                85                  90                  95

Phe Gly Gln Gly Thr Lys Val Glu Ile Lys
            100                 105
```

ANTIBODY BINDING TO CARBONIC ANHYDRASE AND USE THEREOF

TECHNICAL FIELD

The present invention relates to an antibody that recognizes and binds to carbonic anhydrase, a nucleic acid molecule coding for the antibody or an antigen-binding fragment, a vector carrying the nucleic acid molecule, a host cell including the nucleic acid molecule or the vector, and use of the antibody or an antigen-binding fragment thereof in the alleviation, prevention, treatment or diagnosis of diseases related with the carbonic anhydrase, for example, solid tumors.

RELATED ART

Carbonic anhydrase (CA) form a family of enzymes that catalyze the rapid interconversion of carbon dioxide and water to bicarbonate and proton or vice versa to maintain pH homeostasis in the body. The active site of most carbonic anhydrases contains a zinc ion; they are therefore classified as metalloenzymes.

The family of carbonic anhydrases has several members. There are at least five distinct CA families ($\alpha$, $\beta$, $\gamma$, $\delta$ and $\epsilon$). The $\alpha$-CAs are found in mammals. The $\alpha$-CAs are divided into four broad subgroups, which, in turn, consist of several isoforms: cytosolic CAs (CA-I, CA-II, CA III, CA-VII, and CA-XIII), mitochondrial CAs (CA-VA and CA-VB), secreted CAs (CA-VI), and membrane-associated CAs (CA-IV, CA-IX, CA-XII, CA-XIV, and CA-XV).

CA isozymes II, IX and XII have been associated with neoplastic processes, and they are potential histological and prognostic biomarkers of certain tumors [Nordfors et al. (2010), BMC cancer; 10:148]. CA-II is the most widely expressed member of the $\alpha$-CA gene family, being present in virtually every human tissue and organ. The transmembrane enzyme, CA-IX, was first recognized as a novel tumor-associated antigen expressed in several types of human carcinomas as well as in normal gastrointestinal tissue. CA-IX has been functionally linked to cell adhesion, differentiation, proliferation and oncogenic processes, and its enzymatic activity is comparable to CA II. Another transmembrane CA isozyme, CA-XII, was first found in normal kidney tissue and renal cell carcinoma. Further studies have shown that it is expressed in several other tumors (Ulmasov et al. (2000)), but also in some normal organs such as the colon and uterus. High expression of CA-II, CA-IX and CA-XII in tumors, particularly under hypoxic conditions, has further suggested that these enzymes may functionally participate in the invasion process, which is facilitated by acidification of the extracellular space.

DISCLOSURE

Technical Problem

In accordance with an embodiment, the present invention provides an antibody binding to carbonic anhydrase, and an antigen-binding fragment thereof.

Another embodiment of the present invention provides a nucleic acid molecule encoding the antibody or the antigen-binding fragment, a vector carrying the nucleic acid molecule, and a host cell including the nucleic acid molecule.

A further embodiment of the present invention provides a method or a kit for detecting or diagnosing a carbonic anhydrase-associated disease, comprising the antibody, the nucleic acid molecule, the vector, and/or the host cell.

Still a further embodiment of the present invention provides a composition for preventing, treating or alleviating a carbonic anhydrase-associated disease, comprising the antibody, the nucleic acid molecule, the vector, and/or the host cell, or use of the antibody, the nucleic acid molecule, the vector, and/or the host cell in preventing, treating, or alleviating a carbonic anhydrase-associated disease.

Still another embodiment of the present invention provides a method for preventing, treating or alleviating a carbonic anhydrase-associated disease, comprising administering a composition comprising the antibody, the nucleic acid molecule, the vector, and/or the host cell to a subject with a carbonic anhydrase-associated disease.

Yet a further embodiment of the present invention provides a composition or a method for reducing solid tumors or solid tumor cells in size or for inducing or promoting tumor regression.

Technical Solution

The present invention addresses an antibody recognizing and binding to carbonic anhydrase, a nucleic acid molecule coding for the antibody or an antigen-binding fragment, a vector carrying the nucleic acid molecule, a host cell including the nucleic acid molecule or the vector, and use of the antibody or an antigen-binding fragment thereof in the alleviation, prophylaxis, therapy or diagnosis of CA-MI-positive solid tumors.

Useful in the present invention is an antibody that specifically recognizes and binds to carbonic anhydrase. In detail, the antibody of the present invention binds to CA-XII. The antigen determinant, that is, the epitope which the antibody of the present invention binds to is a non-catalytic region located at an N terminus of CA-XII. Preferably, the CA-XII is an enzyme derived from a human. Particularly, the human-derived CA-XII has the amino acid sequence of SEQ ID NO: 5.

The term, "catalytic domain" is well known in the art, and relates, in conjunction with the present invention, to the portion of CA-XII at which the catalysis of carbonic acid to bicarbonate and protons occurs. In contrast, the term "non-catalytic domain" refers to a portion other than the catalytic domain at which the catalysis of carbonic acid to bicarbonate and protons occurs. In the present invention, the non-catalytic domain of CA-XII is an N-terminal, non-catalytic domain, and may mean a peptide consisting of 93 amino acid residues from the N-terminal position 1 to position 93 in the amino acid sequence of SEQ ID NO: 5 for the human-derived CA-XII, or a fragment thereof.

The region of the antigen to which the antibody of present invention binds may be the non-catalytic region or fragment thereof. That is, the region of the antigen can be a peptide consisting of amino acids 1 to 93 of the N-terminus of the amino acid sequence of SEQ ID NO: 5, or a fragment thereof, or $25^{th}$ to 93th amino acids, or $25^{th}$ to $57^{th}$ amino acids in the amino acid sequence of human origin CA-XII isotype I of (SEQ ID NO: 5) or a fragment thereof.

As a specific embodiment, the antigen binding region or epitope to be recognized by the antibody of present invention a peptide having 7 to 93 consecutive amino acids, 7 to 69 consecutive amino acids, 7 to 33 consecutive amino acids, 14 to 93 consecutive amino acids, 14 to 69 consecutive amino acids, 14 to 33 consecutive amino acids, 19 to 93 consecutive amino acids, 19 to 69 consecutive amino acids, or 19 to 33 consecutive amino acids which includes an amino acid sequence of SEQ ID NO: 1, 2, 3 or 4.

More specifically, the antigen binding region or epitope to be recognized by the antibody of present invention a peptide having 7 to 93 consecutive amino acids or 7 to 69 consecutive amino acids which essentially includes an amino acid sequence of SEQ ID NO: 1, preferably 14 to 93 consecutive amino acids or 14 to 69 consecutive amino acids essentially includes an amino acid sequence of SEQ ID NO: 2, more preferably 7 to 14 consecutive amino acids which essentially includes an amino acid sequence of SEQ ID NO: 1 in the amino acid sequence of SEQ ID NO: 2, or most preferably a peptide consisting of SEQ ID NO: 1 or SEQ ID NO: 2.

In the amino acid sequence of human origin CA-XII of SEQ ID NO: 5, the amino acid sequence of SEQ ID NO: 1 may be a peptide composed of 32 to 38 consecutive amino acids and the amino acid sequence of SEQ ID NO: 2 may be 25 to 38 consecutive amino acids.

Alternatively, the antigen binding region or epitope to be recognized by the antibody of present invention a peptide having 14 to 93 consecutive amino acids or 14 to 69 consecutive amino acids which essentially includes an amino acid sequence of SEQ ID NO: 3 in the amino acid sequence of SEQ ID NO: 5, preferably 19 to 93 consecutive amino acids or 19 to 69 consecutive amino acids essentially includes an amino acid sequence of SEQ ID NO: 4 in the amino acid sequence of SEQ ID NO: 5, more preferably 14 to 19 consecutive amino acids which essentially includes an amino acid sequence of SEQ ID NO: 3 in the amino acid sequence of SEQ ID NO: 4, or most preferably a peptide consisting of SEQ ID NO: 3 or SEQ ID NO: 4.

In the amino acid sequence of the human-derived CA-XII of SEQ ID NO: 5, the amino acid sequence of SEQ ID NO: 3 may be a peptide composed of 39 to 52 consecutive amino acids and the amino acid sequence of SEQ ID NO: 4 may be 39 to 57 consecutive amino acids.

The amino acid sequence of SEQ ID NO: 5, which is the amino acid sequence of the human-derived CA-XII, and the epitopes of SEQ ID NO: 1 to 4 are summarized in Table 1.

TABLE 1

| Description | Amino acid sequence | SEQ ID NO |
|---|---|---|
| Epitope of Humanized 27B6 | WTYFGPD | 1 |
| Epitope of Humanized 27B6 | APVNGSKWTYFGPD | 2 |
| Epitope of Humanized 4B4 | GENSWSKKYPSCGG | 3 |
| Epitope of Humanized 4B4 | GENSWSKKYPSCGGLLQSP | 4 |
| Amino acid sequence of Human origin CA XII | MPRRSLHAAAVLLLVILKEQPSSPAP VNGSKWTYFGPDGENSWSKKYPSCGG LLQSPIDLHSDILQYDASLTPLEFQG YNLSANKQFLLTNNGHSVKLNLPSDM HIQGLQSRYSATQLHLHWGNPNDPHG SEHTVSGQHFAAELHIVHYNSDLYPD ASTASNKSEGLAVLAVLIEMGSFNPS YDKIFSHLQHVKYKGQEAFVPGFNIE ELLPERTAEYYRYRGSLTTPPCNPTV LWTVFRNPVQISQEQLLALETALYCT HMDDPSPREMINNFRQVQKFDERLVY TSFSQVQVCTAAGLSLGIILSLALAG ILGICIVVVVSIWLFRRKSIKKGDNK GVIYKPATKMETEAHA | 5 |

The antibody of the present invention is an antibody that specifically recognizes and binds to the non-catalytic region of the carbonic anhydrase, and includes a mouse antibody, a chimeric antibody, or a humanized antibody. The non-catalytic region of the carbonic anhydrase is a peptide or fragment thereof consisting of N-terminal amino acids 1 to 93 in the amino acid sequence of human-derived CA-XII isotype I (SEQ ID NO: 5), a peptide or fragment thereof consisting of N-terminal amino acids 25 to 93 or a peptide or fragment thereof consisting of N-terminal amino acids 25 to 57.

An example of an antibody can bind to a peptide consisting of N-terminal amino acids 1 to 93 in the amino acid sequence of human-derived CA-XII isotype I (SEQ ID NO: 5), or a peptide essentially including SEQ ID NO: 1, or preferably SEQ ID NO: 2 in the amino acid sequence of SEQ ID NO: 5.

In one embodiment of the present invention, an antibody that binds to a peptide comprising the amino acid sequence of SEQ ID NO: 1, wherein the antibody is CDR1 to CDR3 of the heavy chain variable region and CDR1 to CDR3 of light chain variable region of the antibody produced by the hybridoma cell having the accession number KCLRF-BP-00280. The hybridoma cell line was deposited with the Korean Cell Line Research Foundation, Seoul National University Cancer Research Foundation, located at 28, Yongon-Dong, Chongno-gu, Seoul, Korea, on Feb. 14, 2012, and received the accession number of KCLRF-BP-00280 dated Feb. 20, 2012. The antibody produced by hybridoma deposited as the accession number KCLRF-BP-00280 is designated as 27B6, which comprises a heavy chain variable region comprising the amino acid sequence of SEQ ID NO: 12 and a light chain variable region comprising the amino acid sequence of SEQ ID NO: 13.

Specifically, according to an embodiment of the present invention, the antibody may comprise at least one selected from the group consisting of CDR of the $V_H$ region including amino acid sequences of SEQ ID NOS: 6 to 8 and CDR of the $V_L$ region including amino acid sequences of SEQ ID NOS: 9 to 11. In a particular embodiment, the antibody of the present invention may comprise amino acid sequences of SEQ ID NO: 6(CDR1), SEQ ID NO: 7 (CDR2), and SEQ ID NO:8(CDR3) as CDR for VH region and/or amino acid sequences of SEQ ID NO: 9(CDR1), SEQ ID NO: 10(CDR2), and SEQ ID NO: 11(CDR3) as CDR for VL region. The antibody of another embodiment of the present invention may comprise the $V_H$ region including amino acid sequence of SEQ ID NO: 12 and the $V_L$ region including the amino acid sequence of SEQ ID NO: 13.

An example of the antibody is a peptide consisting of N-terminal amino acids 1 to 93 in the amino acid sequence of human-derived isotype I (SEQ ID NO: 5), or a peptide essentially including an amino acid sequence of SEQ ID NO: 3 or preferably SEQ ID NO: 4 in the amino acid sequence of SEQ ID NO: 5.

According to one embodiment of the present invention, an antibody binding to a peptide comprising the amino acid sequence of SEQ ID NO: 3, and examples of the antibody may comprise CDRs 1-3 of the heavy chain variable region and CDRs 1-3 of the light chain variable region of the antibody produced by the hybridoma cell deposited as accession No. KCLRF-BP-00279. The hybridoma cell line has been deposited with the Korean Cell Line Research Foundation, Seoul National University Cancer Research Institute, 28 Yongon-Dong, Chongno-gu, Seoul, Korea, on Feb. 14, 2012, and received the accession number of KCLRF-BP-00279 dated Feb. 20, 2012. The antibody produced by the hybridoma deposited as an accession number KCLRF-BP-00279 is designated as 4B4, and includes a heavy chain variable region comprising the amino acid sequence of SEQ ID NO: 20 and a light chain variable region comprising the amino acid sequence of SEQ ID NO: 21.

Particularly, the antibody of an embodiment of the present invention may comprise at least one selected from the group consisting of CDRs including amino acid sequences of SEQ ID NOs: 14 to 16 and CDRs including amino acid sequences of SEQ ID NOS: 17 to 19, or preferably comprise amino acid sequences of SEQ ID NO: 14 (CDR1), SEQ ID NO: 15 (CDR2) and SEQ ID NO: 16 (CDR3) as the amino acid sequences determining CDR of $V_H$ region, and/or amino acid sequences of SEQ ID NO: 17 (CDR1), SEQ ID NO: 18 (CDR2) and SEQ ID NO: 19 (CDR3) as the amino acid sequences determining CDR of $V_L$ region. The antibody of another embodiment of the present invention may comprise $V_H$ region including the amino acid sequence of SEQ ID NO: 20 and $V_L$ region including the amino acid sequence of SEQ ID NO: 21.

The CDR sequences and variable region sequences according to an example of the mouse antibody or chimeric antibody are summarized in the following table.

TABLE 2

| Name | Amino acid sequence | SEQ ID NO |
|---|---|---|
| 27B6 $V_H$-CDR1 | GYSFTNYW | 6 |
| 27B6 $V_H$-CDR2 | IDPSDSET | 7 |
| 27B6 $V_H$-CDR3 | TRGIRGGYYA MDY | 8 |
| 27B6 $V_L$-CDR1 | QDISNY | 9 |
| 27B6 $V_L$-CDR2 | YTS | 10 |
| 27B6 $V_L$-CDR3 | QQGDTLPRT | 11 |
| 27B6 $V_H$ | QVQLQQSGPQ LVWPGASVKI SCNTSGYSFT NYWIHWVKQR PGQGLEWIGM IDPSDSETRL NQKFKDKTTL TVDRSSSTAY MQVSSSTSED SAVYYCTRGI RGGYYAMDYW GQGTSVTVSS | 12 |
| 27B6 $V_L$ | DIQMTQTTSS LSASLGDRVT ISCRASQDIS NYLNWYQQKP EGTVKLLIYY TSRLHSGVPS RFSGSGSGTD YSLTISNLEQ EDIATYFCQQ GDTLPRTFGE GTKLEIR | 13 |
| 4B4 $V_H$-CDR1 | GYSYTDYN | 14 |
| 4B4 $V_H$-CDR2 | IDPANGDT | 15 |
| 4B4 $V_H$-CDR3 | ARPIYYGVYW YFDV | 16 |
| 4B4 $V_L$-CDR1 | KSLLHSNGNT Y | 17 |
| 4B4 $V_L$-CDR2 | RMS | 18 |
| 4B4 $V_L$-CDR3 | MQHLEYPFT | 19 |
| 4B4 $V_H$ | EIQLQQSGPE LVKPGASVKI SCKASGYSYT DYNIYWVRQS QGKSLDWIGY IDPANGDTTY NQKFKGKATL TVDKSSSTAF MHLNSLTSDG SAVYFCARPI YYGVYWYFDV WGAGTTVTVS | 20 |

TABLE 2-continued

| Name | Amino acid sequence | SEQ ID NO |
|---|---|---|
| 4B4 $V_L$ | DIVMTQAAPS VPVTPGESVS ISCRSSKSLL HSNGNTYLYW FLQRPGQSPQ LLIYRMSNLA SGVPDRFSGS GSGTAFTLRI SRVEAEDVGV YYCMQHLEYP FTFGSGTKLE IK | 21 |

According to an embodiment of the present invention, an antibody binding to an epitope including an amino acid sequence of SEQ ID NO:1 and an antibody binding to an epitope including an amino acid sequence of SEQ ID NO:3 can bind together to the same antigen. Hence, the two antibodies may be useful in a sandwich ELISA assay for the CA-XII antigen. In sandwich ELISA, particularly, the antibody binding to an epitope including an amino acid sequence of SEQ ID NO:1 such as 27B6 antibody may be used as a capture antibody, while the antibody binding to an epitope including an amino acid sequence of SEQ ID NO:3 such as 4B4 antibody may be used as a detector antibody.

According to the present invention, the humanized antibody (hereinafter referred to as DNP004) which binds to the CA-XII antigen is prepared by using the light chain variable region genes and heavy chain variable region genes of mouse monoclonal antibody 4B4 (Accession No. KCLRF-BP-00279) specifically binding to CA-XII as a template. For example, the humanized antibody can include at least one CDR selected from the group consisting of the CDRs of the $V_H$ region comprising the amino acid sequences of SEQ ID NOs: 14, 15 and 28 and the CDRs of the $V_L$ region comprising the amino acid sequences of SEQ ID NOs: 29, 30 and 31.

SEQ ID NO: 29:
ASSX1VTY
(X1 = P or S)

SEQ ID NO: 30:
X2TSX3LX4X5
(X2 = A, G or R; X3 = S, R, H, Q, D, E or M; X4 = A, V, I or M; X5 = P or S)

The CDR1 of the VL region in the antibody is represented by a general formula of SEQ ID NO: 29 and may include the amino acid sequence of SEQ ID NO: 32 or 33 as a specific example. The CDR2 of the VL region is represented by a general formula of SEQ ID NO: 30 and may include an amino acid sequence selected from the group consisting of SEQ ID NOs: 33 to 42 as a specific example.

The CDR sequences and variable region sequences according to an example of the humanized antibody (DNP004) are summarized in the following table. In the SEQ ID NOs: 32 to 42 in Table 3, the bold characters represent the modified amino acid.

TABLE 3

| Name | CDR | Amino acid sequence | SEQ ID NO |
|---|---|---|---|
| DNP004 $V_H$ | CDR1 | GYSYTDYN | 14 |
| DNP004 $V_H$ | CDR2 | IDPANGDT | 15 |
| DNP004 $V_H$ | CDR3 | SRPIYYGAYWYFDV | 28 |
| DNP004 $V_L$ | CDR1 | ASSX1VTY | 29 |

TABLE 3-continued

| Name | CDR | Amino acid sequence | SEQ ID NO |
|---|---|---|---|
| General formula | | (X1 = P or S) | |
| DNP004 $V_L$ General formula | CDR2 | $X_2$TS$X_3$L$X_4X_5$ (X2 = A, G or R; X3 = S, R, H, Q, D, E, M; X4 = A, V, I or M; X5 = P or S) | 30 |
| DNP004 $V_L$ | CDR3 | QQWSSNPLT | 31 |
| DNP004 $V_L$ | CDR1 | ASSPVTY | 32 |
| DNP004 $V_L$ | CDR1 | ASSSVTY | 33 |
| DNP004 $V_L$ | CDR2 | ATSSLAP | 34 |
| DNP004 $V_L$ | CDR2 | ATSSLVS | 35 |
| DNP004 $V_L$ | CDR2 | GTSRLVS | 36 |
| DNP004 $V_L$ | CDR2 | ATSHLVS | 37 |
| DNP004 $V_L$ | CDR2 | GTSQLVS | 38 |
| DNP004 $V_L$ | CDR2 | RTSDLIS | 39 |
| DNP004 $V_L$ | CDR2 | ATSELMS | 40 |
| DNP004 $V_L$ | CDR2 | GTSMLAS | 41 |
| DNP004 $V_L$ | CDR2 | ATSSLAS | 42 |

The framework sequences included in an example of a humanized antibody (DNP004) according to the present invention are summarized in Table 4 below, wherein the antibody comprises at least one selected from the group consisting of the heavy chain variable region frameworks 1 to 4 and the light chain variable region frameworks 1 to 4. The amino acid sequences of Frameworks 1 to 4 of the heavy chain variable region may comprise SEQ ID NOs: 43 to 46, respectively, and the amino acid sequences of Frameworks 1 to 4 of the light chain variable region include SEQ ID NOs: 47, 48, 51 and 52, respectively. The framework 2 of the light chain variable region is represented by the general formula of SEQ ID NO: 48 and may include the amino acid sequence of SEQ ID NO: 49 or 50 as a specific example.

SEQ ID NO: 48:
MHWY$X_6$QKPGKAP$X_7$PWIY
(X6 = Q or H; H7 = R or K)

The framework sequences according to an example of the humanized antibody (DNP004) are summarized in the following table.

TABLE 4

| Name | Amino acid sequence | SEQ ID NO |
|---|---|---|
| Frame work #1 of $V_{H-humanized}$ | EVQLVESGGGLVQPGGSL RLSCAAS | 43 |
| Frame work #2 of $V_{H-humanized}$ | IYWVRQAPGKGLEWVGY | 44 |
| Frame work #3 of $V_{H-humanized}$ | TYNQKFKGRATISVDKSK NTAYLQMNSLRAEDTAVY YC | 45 |
| Frame work #4 of $V_{H-humanized}$ | WGQGTLVTVSS | 46 |
| Frame work #1 of $V_{L-humanized}$ | DIQMTQSPSSLSASVGDR VTITCR | 47 |
| Frame work #2 of $V_{L-humanized}$ General formula | MHWY$X_6$QKPGKAP$X_7$PWIY (X6 = Q or H; H7 = R or K) | 48 |
| Frame work #2 of $V_{L-humanized}$ | MHWYQQKPGKAPRPWIY | 49 |
| Frame work #2 of $V_{L-humanized}$ | MHWYHQKPGKAPKPWIY | 50 |
| Frame work #3 of $V_{L-humanized}$ | GVPSRFSGSGSGTDFTLT ISSLQPEDFATYYC | 51 |
| Frame work #4 of $V_{L-humanized}$ | FGQGTKVEIK | 52 |

As an example, the humanized antibody (DNP004) according to the present invention may comprise a heavy chain variable region comprising the amino acid sequence of SEQ ID NO: 53 and a light chain variable region comprising the amino acid sequence selected from the group consisting of SEQ ID NOs: 54 to 63.

As shown in FIG. 31, the humanized antibody (DNP004) according to the present invention was selected from the candidate antibody groups having higher antigen binding affinity than the chimeric 4B4 antibody (Example 16), which indicates the humanized antibody (DNP004) having higher binding affinity to various cell lines (Example 18). The humanized antibody is significantly reduced immunogenicity potential inherent in the mouse antibody or chimeric antibody and is superior to the chimeric 4B4 antibody.

The antibody or the antigen-binding fragment thereof in accordance with an embodiment of the present invention exhibits tumor regression activity and a direct inhibitory effect on tumor cell lines. As used herein, the term "tumor regression" is intended to encompass the induction or the promotion of the decrease of tumor size, and/or the inhibition, interruption, or reduction of tumor cell growth. The decrease of tumor size means that, when the antibody or a fragment thereof according to the present invention is administered, a tumor size decreases to, for example, 97% or less, 95% or less, 90% or less, 85% or less, 80% or less, or 75% or less of the tumor size before administration.

The antibody according to the present invention exhibits both antibody-dependent cell-mediated cytotoxicity (ADCC) and complement-dependent cytotoxicity (CDC).

According to the present invention, the antibody may be defucosylated as the bound sugar residues, either partially or completely. The defucosylated antibody according to the present invention retains the activity of inhibiting the growth of solid tumors and promoting tumor regression. For example, the 27B6 antibody and the 4B4 antibody exhibit a higher suppressive effect on breast cancer when it is defucosylated than when it is fucosylated (FIGS. 14 and 17).

The antibody or antigen-binding fragment thereof according to the present invention may not exist in the body or may be a non-naturally occurring substance, for example recombinant or synthetic substance. Recombinant or synthetic antibodies or antigen-binding fragments thereof can be produced using the techniques well known in the art.

In addition, the present invention provides a substance recognizing an antigen-determining region of CA-XII. The substance may be selected from the group consisting of an antibody, an antibody fragment, and a ligand. The antibody may be polyclonal or monoclonal, and may be derived from human or animals. For example, the antibody may be monoclonal. Monoclonal antibodies may be prepared using a known method in the art, for example, a phage display technique. A mouse antibody and a chimeric antibody fall within the scope of the antibody according to the present invention.

The term "CDR (Complementarity Determining Region)" refers to an amino acid sequence of the hypervariable region of a heavy chain and a light chain of an immunoglobulin. The heavy chain and the light chain may each include three CDRs (CDRH1, CDRH2, CDRH3, and CDRL1, CDRL2, CDRL3). The CDRs of an antibody can provide an essential contact residue for binding to an antigen or an epitope.

Throughout the specification, the terms "specifically binding" or "specifically recognizing" has the same meaning, as it is generally known to a person of ordinary skill in the art, indicating that an antigen and an antibody specifically interact with each other and cause an immunological response.

The term "antigen-binding fragment," means a fragment of the full structure of an immunoglobulin, which is a partial polypeptide including a domain to which an antigen can bind. For example, it may be scFv, (scFv)$_2$, scFv-Fc, Fab, Fab', or F(ab')$_2$, but is not limited thereto.

The anti-CA-XII antibody may be a monoclonal antibody. Monoclonal antibodies can be prepared by the methods well known in the art. For example, it can be produced using a phage display technique. Alternatively, the anti-CA-XII antibody can be produced using a monoclonal antibody derived from a mouse by a conventional method.

On the other hand, individual monoclonal antibodies can be screened based on their ability to bind CA-XII using a typical ELISA (Enzyme-Linked ImmunoSorbent Assay) format. In order to assay molecular interaction of the conjugates, the functional assays such as competitive ELISA (competitively ELISA) or cell-based assays is used for testing an inhibitory activity. Then, the each antibody affinity (Kd values) for CA-XII is assayed for the monoclonal antibody members selected based on strong inhibitory activity.

The finally selected antibodies can be used as humanized antibodies as well as the antibodies substituted with human immunoglobulin antibodies except for the antigen binding portion. The methods of preparing the humanized antibodies are well known in the art (Almagro, J. C. and Fransson, J., \"Humanization of antibodies,\" Frontiers in Bioscience, 13 (2008), 1619-1633).

Another embodiment provides a hybridoma producing said anti-CA-XII antibody. In an embodiment, the hybridoma may be one having an accession number KCLRF-BP-00279 or KCLRF-BP-00280.

Further embodiment provides an anti-CA-XII antibody produced by said hybridoma or antigen-binding fragment thereof.

Other embodiments include the heavy chain complementarity determining regions (CDR-H1, CDR-H2, CDR-H3, or a combination thereof) of the anti-CA-XII antibody produced by the hybridoma, light chain complementarity determining regions (CDR-L2, CDR-L3, or a combination thereof), or a combination thereof; alternatively, the anti-CA-XII antibody or an antigen-binding fragment thereof comprising a heavy chain variable region, a light chain variable region, or a combination thereof of an anti-CA-XII antibody produced by said hybridoma. At this time, the complementarity determining region may be determined by any conventional method, for example, IMGT definition or Cabat definition, but is not limited thereto.

The anti-CA-XII antibody or fragment thereof may be coupled to various labeling agents, toxins, or anti-tumor drugs. It will be apparent to those skilled in the art that the antibody of the invention can be coupled to a labeling agent, a toxin, or an anti-tumor drug by a method well known in the art. Such coupling may be chemically conducted on the site of attachment after expression of the antibody or antigen. Alternatively, the coupling product may be engineered into the antibody or antigen of the invention at the DNA level. Subsequently, the DNA is then expressed in a suitable host system as described herein below, and the expressed proteins are collected and, if necessary, renatured. Coupling may be achieved via a linker, known in the art. In particular, different linkers that release a toxin or an anti-tumor drug under acidic or alkaline conditions or upon exposure to specific proteases may be employed with this technology. In some embodiments, it may be desirable for the labeling agent, toxin, or anti-tumor drug to be attached to spacer arms in various lengths to reduce potential steric hindrance.

The labeling agent may be selected from the group consisting of a radioisotope, a hapten, a fluorescent, a chromogen, and a dye. Particularly, the labeling agent may be selected from among FLAG, GFP, YFP, RFP, dTomato, cherry, Cy3, Cy5, Cy5.5, Cy7, DNP, AMCA, biotin, digoxigenin, Tamra, Texas Red, rhodamine, Alexa fluors, FITC and TRITC. Alternatively, the labeling agent may be a radioisotope such as, for example, $^3$H, $^{14}$C, $^{15}$N, $^{35}$S, $^{90}$Y, $^{99}$Tc, $^{111}$In, $^{125}$I, or $^{131}$I. Further examples of a suitable labeling agent include enzymatic groups (e.g. horseradish peroxidase, horseradish galactosidase, luciferase, alkaline phosphatase), chemiluminescent groups, biotinyl groups, or predetermined polypeptide epitopes recognized by a secondary reporter.

So long as it is toxic to cells or organisms, any toxin may be used in the present invention. For examples, a radioisotope, a small molecule, a peptide, or a protein may be used as a toxin. The antibody or fragment thereof may be coupled with a toxin to form a fusion protein. As a toxin protein, ricin, saporin, gelonin, momordin, diphtheria toxin, or pseudomonas toxin may be used. As for the radioisotope, its examples include $^{131}$I, $^{188}$Rh, and $^{90}$Y, but are not limited thereto.

As used herein, the term "anti-tumor agent" specifies a drug capable of either stopping or slowing down the abnormal growth of tissues. Thus, anti-tumor agents are particularly useful in treating cancer. An anti-tumor agent may be an angiogenesis inhibitor, a DNA intercalator or a DNA cross-linker, a DNA synthesis inhibitor, a DNA-RNA transcription regulator, an enzyme inhibitor, a gene regulator, a microtubule inhibitor, or other antitumor agents.

The present invention further relates to a nucleic acid molecule encoding the antibody of the present invention. The nucleic acid molecule of the present invention, encoding the antibody of the present invention, may be, for example, DNA, cDNA, RNA, a synthetically produced DNA or RNA, or a recombinantly-produced chimeric nucleic acid molecule comprising any of those nucleic acid molecules, either alone or in combination. The nucleic acid molecule may also be genomic DNA corresponding to an entire gene or a substantial portion thereof, or to a fragment or derivative thereof. The nucleotide sequence of the nucleic acid molecule may be a modified nucleotide sequence in which substitution, deletion or addition occurs on one or more nucleotide residues, and causes substitution or mutation of at least one amino acid residue of the amino acid sequence of the antibody. In a particular embodiment of the present invention, the nucleic acid molecule is a cDNA molecule.

One embodiment of the present invention also relates to a vector comprising the nucleic acid molecule in an expressible form. The vector of the present invention may be, for example, a phage, a plasmid, a viral vector, or a retroviral vector. Retroviral vectors may be replication-competent or replication-defective. In the latter case, viral propagation will generally occur in complementing host/cells.

The aforementioned nucleic acid molecule may be inserted into a vector such that translational fusion with another polynucleotide occurs. Generally, a vector may contain one or more origins of replication (ori) and inheritance systems for cloning or expression, one or more markers for selection in the host, e. g., antibiotic resistance, and one or more expression cassettes. Examples of a suitable origin of replication (ori) include the Col E1, the SV40 viral and the M 13 origins of replication.

In the present invention, the nucleic acid molecule may be designed for introduction into a host, either directly or via a liposome, a phage vector, or a viral vector (e.g. adenoviral vector, retroviral vector, etc.). Additionally, baculoviral systems, or systems based on vaccinia virus or semliki forest virus can be used as eukaryotic expression systems for the nucleic acid molecules of the present invention.

Another embodiment of the present invention pertains to a non-human host including the vector of the present invention. The host may be prokaryotic or eukaryotic. The polynucleotide or vector of the present invention, present in a host cell, may either be integrated into the genome of the host cell or may be maintained extrachromosomally.

In addition, the present invention is concerned with a transgenic, non-human animal, available for the production of the antibody of the present invention, comprising one or more nucleic acid molecules of the present invention. Antibodies can be produced in and recovered from tissue or body fluids, such as milk, blood or urine, from goats, cows, horses, pigs, rats, mice, rabbits, hamsters or other mammals.

Moreover, the present invention provides a method for producing a substance selectively recognizing an antigen-determining region of CA-XII, and a cell line producing an antibody selectively recognizing an antigen-determining region of CA-XII. An antibody to an antigen-determining region of CA-XII or a fragment thereof, may be produced using a typical method with a CA-XII protein, an antigen-determining region of CA-XII, a portion of CA-XII containing an antigen-determining region of CA-XII, or a cell expressing an antigen-determining region of CA-XII serving as an antigen. For example, a method for producing an anti-CA-XII antibody can be achieved through a method for producing a cell line producing an anti-CA-XII antibody, comprising (a) injecting and immunizing an animal with a CA-XII protein, an antigen-determining region of CA-XII, a portion of CA-XII containing an antigen-determining region of CA-XII, or a cell expressing an antigen-determining region of CA-XII, (b) obtaining splenocytes producing an antibody specific for CA-XII, and (c) fusing the splenocytes with myeloma cells to give hybridoma cells and selecting a hybridoma cell producing an antibody to CA-XII. The antibody can be isolated by culturing the cell line in vitro or by introducing the cell line in vivo. For example, the cell line may be intraperitoneally injected into mice, followed by isolating and purifying the antibody from the ascites. Isolation and purification of monoclonal antibodies may be achieved by subjecting the culture supernatant and ascites to ion exchange chromatography (DEAE or DE52) or affinity chromatography using an anti-immunoglobulin column or protein A column.

The antigen-determining region to which the antibody of the present invention binds exhibits solid tumor-specific expression. Hence, the anti-CA-XII antibody can not only be effectively used to detect tumor cells, but can also exert cytotoxicity only on tumor cells when it carries a toxic substance.

A further embodiment of the present invention provides the use of CA-XII, particularly an antigen-determining region located at a non-catalytic domain of CA-XII, in detecting solid tumors. Also, a composition for detecting cancer stem cells of solid tumors, comprising a substance interacting with the antigen-determining region is provided. The interacting substance may be any substance that is able to interact with CA-XII, particularly an antigen-determining region of CD-XII located at a non-catalytic domain thereof. In particular, the interacting substance may be selected from the group consisting of a small molecular chemical, an antibody, an antigen-binding fragment of an antibody, an aptamer, or a combination thereof.

In another embodiment, the present invention relates to a diagnostic composition, comprising the antibody of the present invention, the nucleic acid molecule of the present invention, the vector of the present invention, or the host of the present invention. The term "diagnostic composition", as used herein, refers to a composition comprising at least one of the antibody, the nucleic acid molecule, the vector, and/or the host of the present invention.

The diagnostic composition of the present invention is useful in the detection of undesired expression or over-expression of CA, in particular, CA-XII, in various cells, tissues or another suitable sample, by contacting a sample with an antibody of the present invention and determining the presence of a CA, in particular CA-XII, in the sample. Accordingly, the diagnostic composition of the invention may be available for assessing the onset or status of disease, as defined herein below. In particular, malignant cells, such as cancer cells being capable of expressing CA, in particular CA-XII, can be targeted with the antibody of the present invention, or a fragment or derivative thereof. The cells which have bound the antibody of the present invention might be attacked by immune system functions such as the complement system or by cell-mediated cytotoxicity, and thus reduces the number of or completely eradicating the cells showing undesired expression or over-expression of CA, in particular CA-XII.

In another embodiment, the antibody of the present invention, or a fragment or derivative thereof is coupled to a labeling agent. Such antibodies are particularly suitable for diagnostic applications.

The diagnostic composition of the invention can be administered as an active agent alone or in combination with other agents.

A still further embodiment of the present invention relates to a method for detecting a tumor cell, which comprises (a) reacting the anti-CA-XII antibody with a sample including a tumor cell, and (b) determining that the sample is a tumor if the sample is positive to the antibody. The sample may include, but is not limited to, lymphoid fluid, bone marrow, blood, and blood corpuscles. The tumor cell may preferably be a breast cancer cell, a lung cancer cell, colon cancer, a stomach cancer cell, a prostate cancer cell, or a liver cancer cell.

When used for screening a tumor cell, the anti-CA-XII antibody may be conjugated with a label capable of indicating antigen-antibody reactivity. The label useful for this purpose may include a radioisotope, a fluorescent, a luminescent, a chromogen, and a dye.

Also, the anti-CA-XII antibody of the present invention may be provided for a kit for diagnosing solid tumors.

The diagnostic kit may comprise a means for detecting an antigen-antibody reaction in addition to the anti-CA-XII antibody. The detecting means may be an agent useful for performing a technique selected from the group consisting of flow cytometry, immunohistochemical staining, enzyme-linked immunosorbent assay (ELISA), radioimmunoassay (RIA), enzyme immunoassay (EIA), fluorescence immunoassay (FIA), and luminescence immunoassay (LIA). In this context, the label may be an enzyme such as HRP (horse radish peroxidase), a fluorescent such as FITC (fluorescein-thiocarbamyl ethylenediamine), a luminescent such as luminol, isoluminol, and lucigenin, or a radioisotope such as $^{125}I$, $3H$, $^{14}C$, and $^{131}I$, but is not limited thereto. The conjugation with a label can be determined using a means for measuring an enzymatic reaction with a substrate, fluorescence, luminescence, or radiation. For example, the anti-CA-XII antibody may be prepared for use in an ELISA kit or a strip kit.

The antibodies 27B6 and 4B4 according to some embodiments of the present invention can bind together to the same antigen, because their epitopes do not overlap. Accordingly, the two antibodies may be useful in a sandwich ELISA assay for CA-XII antigen. In sandwich ELISA, particularly, the 27B6 antibody may be used as a capture antibody, while the 4B4 antibody may serve as a detector antibody.

In accordance with an embodiment thereof, the present invention addresses a pharmaceutical composition comprising the antibody, the nucleic acid molecule, the vector, or the host of the present invention. The antibody, the nucleic acid molecule, the vector, or the host of the present invention is used for treating or regressing solid cancer. The treatment or regression of solid tumors can be achieved by administering the nucleic acid molecule, the vector, or the host of the present invention at an effective dose to a subject in need thereof.

The term, "solid tumor", as used herein, defines an abnormal mass of tissue that usually does not contain cysts or liquid areas. The solid tumor may be benign (not cancer) or malignant (often referred to as cancer in the art). Examples of solid tumors to which the antibody according to the invention is applicable, include sarcoma, glioma, malignant neoplasm, mesothelioma, lymphoma, kidney cancer, lung cancer, breast cancer, cervical cancer, ovarian cancer, colon cancer, liver cancer, prostate cancer, pancreatic cancer, and head and neck cancer, and preferably breast cancer, lung cancer, colorectal cancer, gastric cancer, prostate cancer or liver cancer. The breast cancer may be a triple-negative breast cancer (TNBC), which can be detected as negative by using three diagnostic makers of HER2, estrogen receptor (ER), and progesterone receptor (PR), and thus is very difficult to be detected. The lung cancer may be small cell lung cancer, non-small cell lung cancer, adenocarcinoma of lung, or squamous cell carcinoma of lung.

The therapeutic effect of solid tumors in accordance with the present invention includes suppressing effects on the migration, invasion, and metastasis of cancer cells (particularly, cancer stem cells) or tissues including cancer cells, and thus on alleviation of the malignancy of cancer as well as their growth inhibition (quantitative reduction) and apoptosis.

As used herein the term "subject" or "patient" refers to a mammal, including a primate such as a human, a monkey, etc., and a rodent such as a mouse, a rat, etc., that is afflicted with, or has the potential to be afflicted with a solid tumor or symptom and thus which is in need of alleviation, prevention, and/or treatment of the solid tumor.

The administration of the antibody or its fragment according to the present invention may be conducted in any acceptable manner. For example, a therapeutic agent including the anti-CA-XII antibody as an active ingredient is administered orally or parenterally, and preferably parenterally, to a subject, e.g., a human or an animal that has tumor cells. The therapeutic agent may include a pharmaceutically acceptable excipient, and the dose of the therapeutic agent may vary depending on the condition of the patient, and may range from, for example, 3 mg to 6,000 mg per day. The therapeutic agent may take such forms as liquids, powders, emulsions, suspensions or injections, but is not limited thereto.

Further, the present invention provides a method for treating acute or chronic myelogenous or lymphocytic leukemia, using at least one selected from among an antibody to an antigen-determining region of CA-XII, a fragment of the antibody (F(ab')$_2$, Fab, Fv, etc.), and a ligand to an antigen-determining region of CA-XII.

An antibody or a fragment thereof may be monoclonal or polyclonal, and may be derived from humans or animals. The anti-CA-MI antibody or its fragment may further comprise the toxin described above. The toxin may be fused, coupled, conjugated or linked to the antibody using a well-known technique.

The pharmaceutical composition of the present invention may be administered as a single active agent or in combination with any other agents that are preferable for the treatment of the disease of interest. In addition, the antibody of the present invention may be used in conjunction with other anticancer therapies, such as chemotherapy, radiotherapy, cytotherapy, etc. Various, well-known anticancer agents may be used in chemotherapy or cytotherapy.

Another embodiment of the present invention provides a method for screening a therapeutic agent or inhibitor of solid tumors, comprising contacting a candidate compound with CA-XII, particularly an antigen-determining region located at a non-catalytic domain of CA-XII, and classifying the candidate compound as a potential therapeutic agent for solid tumors if the candidate compound is determined to bind to the antigen-determining region. A further embodiment of the present invention provides a pharmaceutical composition for treating solid tumors, comprising the screened therapeutic agent for solid tumors as an active ingredient.

The candidate compound may be at least one selected from the group consisting of various synthetic or naturally occurring compounds, polypeptides, oligopeptides, peptides or protein constructs (e.g., antibodies, antigen-binding fragments, peptibodies, nanobodies, etc.), polynucleotides, oligonucleotides, antisense-RNA, shRNA (short hairpin RNA), siRNA (small interference RNA), aptamers, and extracts from natural products.

Binding between a candidate compound and an antigen-determining region can be determining by detecting the formation of a complex, which can be conducted using various methods known in the art. By way of example, typical enzyme reactions, fluorescence, luminescence and/or radiation may be detected to confirm the binding of the candidate compound to the antigen-binding region. In detail, techniques available for the detection of the complex include, but are not limited to, immunochromatography, immunohistochemistry, enzyme-linked immunosorbent assays (ELISA), radioimmunoassays (RIA), enzyme immunoassays (EIA), fluorescence immunoassays (FIA), luminescence immunoassays (LIA), and Western blotting.

Advantageous Effects

Provided are an antibody recognizing and binding to carbonic anhydrase, a nucleic acid molecule encoding the antibody or an antigen-binding fragment of the antibody, a vector carrying the nucleic acid molecule, a host cell including the vector or the nucleic acid molecule, and use of the antibody or an antigen-binding fragment thereof in the alleviation, prevention or diagnosis of diseases related with the carbonic anhydrase such as solid tumors.

BRIEF DESCRIPTION OF DRAWINGS

FIG. 1 shows titers of the solid tumor-specific mouse monoclonal antibody, 27B6 in peripheral blood, as measured according to Example 1.

FIG. 2 shows the antigen specificity and affinity of the 27B6 chimeric antibody, as measured according to Example 2;

FIG. 3 illustrates a procedure of screening titers of the 4B4 monoclonal antibody in peripheral blood, as measured according to Example 3, FIG. 4 shows the antigen specificity and affinity of the 4B4 chimeric antibody, as measured according to Example 4;

FIGS. 5*a*, 5*b* and 5*c* show expression patterns of the mouse chimeric antibody 4B4 on the carbonic anhydrase 12 antigen in various breast cancer cells, as measured according to Example 5.

FIG. 6 shows electrophoretograms of antigens isolated and purified from the lung adenocarcinomic A549 cell line through columns fabricated with chimeric antibody 4B4 and chimeric antibody 27B6.

FIG. 7 shows the identification of carbonic anhydrase 12 as an antigen for the 4B4 and the 27B6 monoclonal antibody, as analyzed by ELISA assay.

FIG. 8 shows the identification of carbonic anhydrase 12 as an antigen for the 4B4 and the 2786 monoclonal antibody, as analyzed by Western blotting assay in Example 6, FIG. 9 shows epitope mapping processes and results of 27B6 and 4B4 monoclonal antibodies.

FIG. 10 shows the complement-dependent cytotoxic effects of chimeric antibody 27B6, as analyzed according to Example 8, FIG. 11 shows antibody-dependent cell-mediated cytotoxic effects of the 27B6 chimeric antibody, as analyzed according to Example 9-1, FIG. 12 shows antibody-dependent cell-mediated cytotoxic effects of the 27B6 chimeric antibody on triple-negative breast cancer cell lines, as analyzed according to Example 9-2, FIG. 13 shows the antibody-dependent cell-mediated cytotoxic effects of the defucosylated 27B6 chimeric antibody in the various solid tumors, as analyzed according to Example 10-1, FIG. 14 shows the antibody-dependent cell-mediated cytotoxic effects of the defucosylated 4B4 and 27B6 chimeric antibodies in the breast cancer cell line, as analyzed by a luciferase assay in Example 10-2.

FIG. 15 shows the expression levels of the CA12 antigen on triple-negative breast cancer cell lines and the binding of 27B6 and 4B4 chimeric antibodies to the cell surface of the cell lines, as analyzed according to Example 11.

FIG. 16 shows the inhibitory activities of 27B6 and 4B4 chimeric antibodies against tumor growth in triple-negative breast cancer animal models.

FIG. 17 shows the inhibitory activity of the 4B4 antibody against triple-negative breast cancer, as analyzed according to Example 11.

FIGS. 18 and 19 show that the binding of the 4B4 antibody alone to tumor cells does not affect the growth of the tumor cells according to Example 12

FIG. 20 shows the effect of a combination of the 27B6 antibody and radiotherapy, as analyzed according to Example 13.

FIG. 21 shows the results of FI ISA Test for the affinity binding to CA-XII of the selected clone (phage displayed scFv) selected according to Example 14.

FIG. 22 shows the sequence of the light chain variable region (VL) and CDR1 and CDR2 sequences of 10 clones (clone numbers #1, 2, 8, 11, 15, 19, 22, 25, 26 and 30) selected according to Example 14 and the sequences of CDR1 and CDR2 Array.

FIG. 23 and FIG. 24 are graphs showing affinity test results of full length IgG of 10 clones (clone numbers #1, 2, 8, 11, 15, 19, 22, 25, 26 and 30) selected according to Example 14.

FIG. 25 shows the binding of the humanized antibody DNP004 according to Example 15 in the CA-XII positive and triple negative breast cancer cell line MDAMB-231.

FIG. 26 is a photograph showing the result of analyzing physical properties of candidate antibody groups using SDS-PAGE according to Example 16.

FIG. 27 shows the evaluation of the binding force of the candidate antibody groups with the CA XII positive cell line according to Example 16.

FIG. 28 and FIG. 29 show results of binding profiles of DNP004 humanized antibody against carbonic anhydrase XII antigen in various breast cancer cells according to Example 17.

FIG. 30 shows the results of antibody-dependent cytotoxic effect of DNP004 humanized antibody in a breast cancer cell line according to Example 18.

FIG. 31 shows the results of the antibody-dependent cytotoxic effect of DNP004 humanized antibody in a lung cancer cell line according to Example 18.

FIG. 32 shows the results of the antibody-dependent cytotoxic effects of DNP004 humanized antibody in liver cancer cell line according to Example 18.

FIG. 33 shows the results of the antibody-dependent cytotoxic effects of DNP004 humanized antibody in stomach cancer cell line according to Example 18.

FIGS. 34 to 35 show the results of the antitumor effect of a DNP004 humanized antibody in a triple negative breast cancer mouse model according to Example 19.

FIG. 36 shows the results of the antitumor effect of DNP004 humanized antibody in an animal model of kidney cancer cell line according to Example 19.

FIG. 37 is the receipt of an original deposit of microorganism (Accession No. KCLRF-BP-00279).

FIG. 38 is the receipt of an original deposit of microorganism (Accession No. KCLRF-BP-00280).

MODE FOR INVENTION

A better understanding of the present invention may be obtained through the following examples which are set forth to illustrate, but are not to be construed as limiting the present invention.

Example 1: Production of Monoclonal Antibody for CA-XII (27B6)

The development of novel antibodies specific for CA12 was achieved in the following experiments. The developed antibodies were observed to be specific for solid tumors, such as adenocarcinoma of the lungs, breast cancer, colorectal cancer, and prostate cancer, as they reacted with antigens expressed specifically in the tumors. They were designated 27B6 and 4B4, respectively.

1-1: Design of Target Site for Construction of 27B6 Monoclonal Antibody

An antibody specific for solid tumor cells was fabricated. For this, mice were immunized directly with solid tumor cells, and monoclonal antibodies were established using a cell fusion technique. Thereafter, an antigen to which the solid tumor cell-specific monoclonal antibody was bound was analyzed and identified.

1-2: Mice Immunization

A549 cells, which are adenocarcinomic human alveolar-basal epithelial cells, were immunized, and a selection was made of an antibody that was positive to the A549 cell line, but L132 during a hybridoma selection process using flow-cytometry. The percentage of positive cells to monoclonal antibody was calculated as the number of cells binding to DNP004 antibody in 5000 cells of the test subject, so as to present as %, − (negative) is referred to the case that the number of positive cells is less than 10%, and + (positive) is referred to the case that the number of positive cells is in the range of 10 to 30%. ++ means that the number of positive cells are in the range of 30 to 70%, and +++ means that the number of positive cells are 70 to 100%.

To the end, Balb/c female mice with 6 weeks old were each IP (intraperitoneal cavity)-injected with the A549 cell line (ATCC CCL-185) at a dose of 1×10$^7$ cells three times at regular intervals of three weeks, followed by removing sera from the veins. A dilution of the serum was added to A549 cells. After being left for 30 min at 4° C. to react, the dilution was mixed with 3 ml of PBS and centrifuged for 3 min at 1500 rpm. Unbound antibodies were washed off. A 200-fold dilution of the secondary antibody goat anti-mouse Ig-FITC (DINONA INC, Korea) was used to detect the bound antibodies. After reaction for 15 min at 4° C., the reaction mixture was washed with 3 ml of PBS in the same manner. The sera were measured for antibody titer to A549 cells by flow cytometry. The sera immunized with A549 cells were observed to be highly positive to A549 cells (results not shown). Briefly, three days before a cell fusion experiment, 50 μg of anti-CD40 agonist mAb was added to boost an immune reaction, and A549 (ATCC CCL-185) was injected at a dose of 1×0$^7$ cells to induce the amplification of an antibody to a surface antigen of A549.

1-3: Preparation of Hybridoma Cell

The spleen was excised from the immunized mice, and a suspension of single splenocytes was obtained and washed twice with RPMI (GIBCO). Viable cells were counted using a 1:1 (v/v) mixture of 0.4% trypan blue (Sigma), which stains only dead cells. The X63 mouse myeloma cell line (ATCC CRL-1580) was employed as a cell fusion partner, and washed and counted in the same manner as the splenocytes.

The myeloma cells were mixed at a ratio of 1:5 with the splenocytes and centrifuged. The pellet thus obtained was slowly added over 1 min with 1 ml of 50% PEG (polyethylene glycol) 1500 preheated to 37° C. After being incubated for about 1 min, the cell mixture was slowly diluted with an RPMI medium and centrifuged. The resulting cell pellet was resuspended in RPMI (20% FBS) containing 1×HAT (hypoxanthine-aminopterin-thymidine), plated at a volume of 150 μl/well into 96-well plates, and grown in a 37° C. $CO_2$ incubator. HAT was fed over a predetermined time after the fusion. When a colony was observed in the wells, 150 μl of an HT medium was added to each well, followed by incubation for 48 hours in a 37° C., 5% $CO_2$ incubator. Then, three-color immunofluorescence staining was performed before flow cytometry. Briefly, the lung adenocarcinoma cell line A549 and the normal lung cell line L132 were immunologically stained with two different dyes and mixed at a ratio of 1:1. This cell mixture was incubated with 100 μl of a supernatant of the hybridoma cell culture at 4° C. for 30 min and centrifuged, together with 3 ml of PBS, at 1500 rpm for 3 min to remove unbound antibodies. The bound antibodies were detected by incubation with a 200-fold dilution of the secondary antibody goat anti-Mouse Ig-APC (DINONA INC, Korea) at 4° C. for 15 min, followed by washing with 3 ml of PBS in the same manner. Thereafter, the hybridoma cells were measured via flow cytometry.

An examination was made to see whether the antibody binds to peripheral blood. For this, PBMC (peripheral blood mononuclear cells from the Korean Red Cross Blood Services) was incubated with 100 μl of a hybridoma supernatant at 4° C. for 30 min, and centrifuged, together with 3 ml of PBS, at 1,500 rpm for 3 min to wash off unbound antibodies. A 200-fold dilution of the secondary antibody goat anti-mouse Ig-FITC (DINONA INC, Korea) was used to detect the bound antibodies. After reaction for 15 min at 4° C., the reaction mixture was washed with 3 ml of PBS in the same manner. The antibody titer was measured using flow cytometry, and the results are shown (FIG. 1). FIG. 1 shows titers of the lung adenocarcinoma-specific 27B6 monoclonal antibody in the peripheral blood, as measured via flow cytometry.

In this manner, the antibody that was positive to the lung cancer cell line A549 and negative to the normal lung cell line L132 and all of granulocytes, lymphocytes and monocytes of the peripheral blood were selected and designated "27B6". Finally, during a limiting dilution procedure, 27B6 hybridoma cells were diluted and selected for single colony growth.

The 27B6 hybridoma cell line was deposited on Feb. 14, 2012, with the Korean Cell Line Bank, located at 28, Yongon-Dong, Chongno-gu, Seoul, Korea, and received Accession No. KCLRF-BP-00280 on Feb. 20, 2012.

1-4: Determination of Isotype for 27B6 Monoclonal Antibody

The 27B6 monoclonal antibody prepared in Example 1-3 was analyzed for isotype, using a mouse immunoglobulin isotyping ELISA kit (BD Biosciences, USA). Briefly, isotyping was performed with anti-murine isotype specific antisera (IgG1, IgG2a, IgG2b, IgG3, IgM, IgA, Kappa, Lambda) while peroxidase-labeled goat anti-mouse IgG served as a secondary antibody. Color development was induced with ortho-phenylenediamine (OPD) and a hydrogen peroxide substrate. Absorbance at 450 nm was read.

As a result, the 27B6 monoclonal antibody was identified as mouse IgG1/kappa light chain (results not shown).

1-5: CDR Sequences of 27B6 Antibody

An antibody cloning procedure is illustrated in FIG. 1. Specifically, the 27B6 antibody gene was cloned using Mouse Ig-Primer Set (Millipore, Cat. #: 69831). PCR was performed using the mouse Ig-primer set from the RNA isolated from the 27B6 hybridoma, inserted into a pGem-T vector (Promega, Cat, #: A3600), and sequenced to confirm the DNA sequence. The mouse antibody gene was identified through the IMGT site. Heavy and light chain sequences including the CDR sequences of the 27B6 Ab are represented by SEQ ID NOs: 12 and 13, respectively, CDR1 to CDR3 of the heavy chain variable region are shown in SEC) ID NOs: 6 to 8, respectively, and CDR1 to CDR3 of the light chain variable region are shown in SEQ ID NOs: 9 to 11, respectively (see the Table 2).

Example 2: Production of 27B6 Chimeric Antibody

When a monoclonal antibody of mouse origin is administered to the human body, the human immune system recognizes the monoclonal antibody as a foreign antigen and thus produces a human anti-mouse antibody (HAMA) to eliminate the mouse antibody from the blood. In addition, the Fc domain of the mouse antibody cannot exert its effective biological functions in the human body. Therefore, not only does the therapeutic effect sharply decrease, but also side effects such as severe allergic reactions and renal dysfunction may be induced. In order to reduce the immunogenicity of the 27B6 antibody upon administration to the human body, a chimeric antibody in which the mouse antibody, except for the variable region, was substituted with the Fc of the human antibody was constructed. The chimeric antibody was observed to be similar in antigen specificity and affinity to the original mouse 27B6 antibody.

To construct a chimeric antibody, the 27B6-HuIgFc DNA prepared in the above-mentioned manner was transfected into the DHFR DG44 cell line derived from CHO cells, followed by a selective culturing procedure in a selective medium to establish a stable cell line producing a 27B6 recombinant antibody. Details are described as follows.

First, three hours before transfection, the DG44 cell line (Invitrogen, Cat No. A1100001) was inoculated at a density of $1 \times 10^6$ cells/ml into 6-well plates and incubated with 1 ml of GIBCO® CD DG44 Medium (Invitrogen, USA) at 37° C. in a 5% $CO_2$ atmosphere for 3 hours. Then, the 27B6-HuIgFc DNA was transfected into the competent DG 44 cells using an Effectene transfection reagent kit (QIAGEN, Hilden, Germany).

On three days post transfection, the supernatant was taken and added to A549 cells which were then incubated at 4° C. for 30 min. Unbound antibodies were removed by centrifugation, together with 3 ml of PBS, at 1500 rpm for 3 min. The bound antibodies were detected by incubation with a 150-fold dilution of the secondary antibody goat anti-Mouse Ig-FITC (DINONA INC, Korea) at 4° C. for 15 min, followed by washing with 3 ml of PBS in the same manner. Thereafter, the antibody titer to A549 cells was measured using flow cytometry. Subsequently, a stable cell line was established. For this, the medium was exchanged with a Power CHO medium (LONZA, Switzerland) supplemented with 30 nM MTX (Sigma, USA) and 200 µg/ml G418 (Invitrogen, USA), after which clone selection was started. Concentrations of MTX and G418 in the selection medium were increased with the repetition of clone selection rounds. Each round was set to be three weeks. The final round of clone selection was performed in a PowerCHO medium supplemented with 1000 nM MTX and 400 µg/ml G418. Thereafter, the final cell line was established as a single colony through limiting dilution.

The 27B6 chimeric antibody established in this manner was found to have antigen specificity and affinity to those of the original mouse 27B6 antibody, as measured by flow cytometry (FIG. 2). FIG. 2 shows the antigen specificity and affinity of the 27B6 chimeric antibody.

Example 3: Production of Monoclonal Antibody for CA XII (4B4)

3-1: 27B6 Pairing Antibody

To develop another antibody which recognizes the same antigen but binds to a different epitope, 27B6 pairing antibody was developed.

Firstly to explore the possibility of development of 27B6 paring antibody, sandwich ELISA using chimeric 2786 and mouse serum was established. In the same manner of Example 1-2, balb/c female mice 6 weeks old were each IP (intraperitoneal cavity)-injected with the A549 cell line ($1 \times 10^7$ cells) at regular intervals of three weeks, followed by taking sera from the veins.

Specifically, chimeric 27B6 purified antibody was added to a microplate at a concentration of 100 ng/mL and coated at 37° C. for 1 hour. Blocking buffer (Sigma) was added to 200 µl/well of 27B6-coated microplate and blocked at 37° C. for 1 hour. A549 cells were lysed at $1 \times 10^7$ cells/ml using 1% NP40 lysis buffer. The prepared A549 lysate was added to the microplate at 50 uL/well, reacted at 37° C. for 1 hour, and then washed three times with PBS. 100 µl/well of A549 immunized mouse serum 1000-fold dilution was added to the microplate and incubated at 37° C. for 1 hour and then washed three times with PBS. Finally, a secondary antibody goat anti-mouse IgG-HRP (Jackson) 2000 dilution was added at 100 µL/well and incubated at 37° C. for 30 minutes, followed by 3 washes with PBS. TMB (3,3',5,5'-tetramethylbenzidine) was added at 50 µL/well, followed by reaction at room temperature for 10 minutes to induce color development, and 2N H2SO4 (Sigma) was added in the same amount. The absorbance was then measured at a wavelength of 450 nm.

As was expected, the positive reaction was observed in sandwich ELISA using chimeric 27B6 and mouse serum (data not shown).

3-2: Production of Monoclonal Antibody

Preparation of hybridoma cells from splenocytes of the immunized mice was carried out in the same manner as in Example 1-3.

As a result, the antibody that was positive to the lung cancer cell line A549 and negative to the normal lung cell line L132 and to all of the granulocytes, lymphocytes and monocytes in peripheral blood, like 27B6, was selected and designated "4B4". Finally, during a limiting dilution procedure, 4B4 hybridoma cells were diluted and selected for single colony growth (FIG. 3). FIG. 3 shows titers of the 4B4 monoclonal antibody in the peripheral blood, as measured by flow cytometry. The 4B4 hybridoma cell line was deposited on Feb. 14, 2012, with the Korean Cell Line Bank, located at 28 Yongon-Dong, Chongno-gu, Seoul, Korea, and received Accession No. KCLRF-BP-00279 on Feb. 20, 2012.

3-3: Analysis of 4B4 Antibody

The amino acid sequences of the antibody were analyzed according to the substantially same method of Example 1-5. Heavy chain sequences and light chain sequences including the CDR sequences of the 4B4 Ab obtained in Example 3-2 are represented by SEQ ID NOs: 20 and 21, respectively, and CDR1 to 3 of heavy chain are shown in SEQ ID NO: 14 to 16, and CDR1 to 3 of light chain are shown in SEQ ID NO: 17 to 19 (see Table 2).

Example 4: Production of 4B4 Chimeric Antibody

In order to reduce the immunogenicity of the 4B4 antibody upon administration to the human body, a chimeric antibody in which the mouse antibody, except for the variable region, was substituted with the Fc of the human antibody was constructed according to Example 2. The chimeric antibody was observed to be similar in antigen specificity and affinity to the original mouse 4B4 antibody.

The production method of 4B4 chimeric antibody was carried out according to the same method of <Example 2>. As a result, the prepared antibody was found to have antigen specificity and affinity similar to those of the original mouse 4B4 antibody, as measured by flow cytometry (FIG. 5). FIG. 5 shows the antigen specificity and affinity of the 4B4 chimeric antibody.

Example 5: Analysis of Antibody Expression in Various Cell Lines 5-1: Antibody Expression in Various Cell Lines 27B6 chimeric antibody obtain in Example 2 and 4B4 chimeric antibody obtain in Example 4 were analyzed for binding to various cell lines obtained from KCLB (Korean Cell Line Bank) and SNU (Seoul National University) using flow cytometry.

Specifically, various cell lines were obtained from KCLB (Korean Cell Line Bank) and SNU (Seoul National University). At 37° C. under a 5% $CO_2$ atmosphere, L-132, SW-900, DU145, LNCap, MCF-7, Huh7, and Hs-578T were cultured in Dulbecco's MEM (GIBCO, Invitrogen) supplemented with 10% heat-inactivated fetal bovine serum (PBS; GIBCO, Invitrogen) and A549, NCI-H460, NCI-H417, DLD-1, HCT116, HT-29, SW-480, SW-620, LS174T, PC-3, SNU1, SNU638, SNU719, MKN1, MKN28, MKN45, MKN74, NCI-N87, SK-BR3, MDA-MB231, and MDA-MB453 were cultured in RPMI 1640 (GIBCO, Invitrogen) supplemented with 10% heat-inactivated FBS. In addition, incubation was carried out at 37° C. under a 5% $CO_2$ atmosphere in Eagles MEM (GIBCO, Invitrogen) supplemented with 10% heat-inactivated fetal bovine serum (PBS; GIBCO, Invitrogen) for Calu-3, Hep3B, SK-HEP-1, C3A, Hep G2, PLC/PRF/5, and BT-20, in IMDM (GIBCO, Invitrogen) supplemented with 20% heat-inactivated fetal bovine serum (FBS; GIBCO, Invitrogen) for KATO III, and in Leibovitz's L-15 medium supplemented with 10% heat-inactivated fetal bovine serum (FBS; GIBCO, Invitrogen) for SW480 and MDA-MB468.

The cultured cancer cell lines were incubated with the 27B6 or the 4B4 monoclonal antibody of the present invention at 4° C. for 30 min, washed with PBS, and treated with FITC-conjugated goat anti-mouse IgG (DINONA INC, Korea) at 4° C. for 15 min. The cell lines were washed again with PBS before analysis by FACScaliber (Becton Dickinson, USA). The results are summarized in Table 5, below. Also, titers of the 27B6 and the 4B4 antibody were measured in various solid tumor cell lines.

The following Table 5 shows the expression pattern of the carbonic anhydrase 12 antigen in various solid cancer cell lines. In Table 16, the percentage of positive cells for 27B6 and 4B4 monoclonal antibodies among the 5000 cells to be tested was analyzed by FACS analysis, and − indicates 10% or less of the number of positive cells, + indicates the range from 10 to 30% of the number of positive cells, ++ refers to 30~70% of the number of positive cells, and +++ refers to 70~100% of the number of positive cells. When the number of positive cells is less than 10%, it is regarded as negative, and when the number of positive cells is 10% or higher, it is regarded as positive.

TABLE 5

| Origin | Cell line | 27B6 | 4B4 |
|---|---|---|---|
| Lung | A549 | +++ | +++ |
|  | NCI-H460 | ++ | ++ |
| Colon | HCT116 | + | − |
|  | HT-29 | + | + |
|  | LS174T | +++ | +++ |
| Prostate | LNCap | + | + |
| Stomach | SNU 719 | + | ++ |
|  | MKN 45 | + | +++ |
| Liver | Huh-7 | − | ++ |
|  | Hep3B | − | + |
|  | PLC/PRF/5 | +++ | +++ |
| Breast | MCF-7 | + | + |
|  | SK-BR3 | +++ | +++ |
|  | MDAMB231 | +++ | +++ |
|  | MDAMB453 | +++ | ++ |
|  | BT20 | + | − |
| PBMC | Lymphocyte | − | − |
|  | Monocyte | − | − |
|  | Granulocyte | − | − |

Cell binding profiling of 4B4 chimeric antibody performed by flow cytometry.
−: less than 10% of number of positive cells
+: 10~30%
++: 30~70%
+++: higher than 70%.

As shown in Table 5, the 27B6 and 4B4 monoclonal antibodies of the present invention showed a positive reaction, although the degree of binding affinity was different in various types of lung cancer, colorectal cancer, stomach cancer, liver cancer and breast cancer cell line. In contrast, peripheral blood lymphocytes, mononuclear cells, and granulocytes showed all negative results. This shows that the 27B6 and 4B4 antibodies of the present invention can be used as therapeutic agents against solid tumors expressing CA XII antigen.

5-2: Expression Pattern in Breast Cancer Cell

27B6 and 4B4 were observed to have positive responses to ER-, PR-, and HER2-positive breast cancer cells. Accordingly, both antibodies can be used as therapeutic agents for various breast cancer subtypes including triple-negative breast cancer.

The binding of the 27B6 and the 4B4 monoclonal antibody to three different phenotype breast cancer cell lines was examined via flow cytometry. Cell culturing was carried out at 37° C. under a 5% $CO_2$ atmosphere for MCF-7 cells (Breast cancer cell, ER positive) in Dulbecco's MEM (GIBCO, Invitrogen) supplemented with 10% heat-inactivated fetal bovine serum (FBS; GIBCO, Invitrogen) and for MDA-MB231 (cell lines derived from malignant breast cancer) and SK-BR-3 cells (human breast cancer cell line that overexpresses the Her2 (Neu/ErbB-2) gene product) in RPMI 1640 (GIBCO, Invitrogen) supplemented with 10% heat-inactivated FBS.

The cultured cancer cell lines were incubated at 4° C. for 30 min with the 27B6 or the 4B4 monoclonal antibody of the present invention, washed with PBS, and treated at 4° C. for 15 min with FITC-conjugated goat anti-mouse IgG (DI-NONA INC, Korea). The cell lines were washed again with PBS before analysis by FACS caliber (Becton Dickinson, USA). The results are summarized in Table 6.

TABLE 6

| Origin | Cell line | Subtype | Immunoprofile | 4B4 Expression |
|---|---|---|---|---|
| Breast | MCF-7 | Luminal | ER+, PR+, HER2− | +++ |
|  | SK-BR3 | HER2 | ER−, PR−, HER2+ | ++ |
|  | MDAMB453 | Basal | ER−, PR−HER2− | +++ |
|  | MDAMB231 | Basal | ER−, PR−HER2− | +++ |
|  | MDAMB468 | Basal | ER−, PR−HER2− | + |
|  | HS578T | Basal | ER−, PR−HER2− | + |
|  | BT20 | Basal | ER−, PR−HER2− | − |

Therefore, the antibodies 27B6 and 4B4 according to the present invention can be used not only for triple negative breast cancer but also for various types of breast cancer, because they show the positive reaction in both ER and PR as well as HER2-positive breast cancer cells.

5-3: WIC (Immunohistochemistry)

Antigens to which 27B6 and 4B4 monoclonal antibodies bind were analyzed for distribution in normal tissues of the human body by immunohistochemistry (NC). Normal thymus and tonsil tissues of the human body were obtained from the Chungbuk National University Hospital and prepared into cryosections in the department of pathology in the Chungbuk National University Hospital.

The prepared cryosections were subjected to immunohistochemical staining with 27B6 and 4B4 monoclonal antibodies of the present invention as follows. Thymus and tonsil cryosections stored at −20° C. or lower were dried at room temperature for 30-60 min, and immersed in 1×PBS for 60 min. Then, the tissues were treated at room temperature for 10 min with 3% $H_2O_2$ to suppress the activity of endogenous peroxidase, washed with flowing water, and blocked at room temperature for 30 min with a goat immunoglobulin-containing serum to exclude non-specific staining with mouse antibodies. Then, the tissues were incubated at room temperature for 60 min with the primary antibody (27B6, 4B4). Each antibody was used at a concentration of 10 μg/ml. Thereafter, the tissues were washed three times with 1×PBS for 5 min, incubated at room temperature for 30 min with an HRP-conjugated goat anti-mouse antibody (Dako, Denmark), and then washed three times with 1×PBST (0.05% Tween20, 1×PBS) for 5 min. The color was developed with diaminobenzidine (DAB), followed by washing for 5 min with flowing water. The tissues were counterstained with hematoxylin and then washed for 7 min with flowing water. After staining, the slides were dehydrated and sealed. The staining results were analyzed by microscopy below.

TABLE 7

| Tissue | | 27B6 | 4B4 |
|---|---|---|---|
| Thymus | Cortex | − | − |
|  | Medulla | − | − |
| Tonsil | Inter follicular T cell | − | − |
|  | B cell | − | − |
|  | Germinal center | − | − |
|  | Basal layer | Basal layer+ | |

As shown in Table 7, the antigens that the 27B6 and the 4B4 monoclonal antibody of the present invention recognize are distributed neither in normal thymus nor in normal tonsil tissues. Particularly, nowhere are the antigens expressed in normal mature or immature T cells or B cells. The 27B6 antibody was weakly stained in the basal layer of the tonsil, which, however, seemed to result from non-specific binding.

Example 6: Analysis of Antigen for Monoclonal Antibody 6-1: Isolation and Purification of 4B4 and 27B6 Monoclonal Antibodies The lung adenocarcinoma cell line A549 that had been used to develop the 4B4 and the 27B6 monoclonal antibody was cultured. Then, 1×10⁸ cells were suspended in 50 ml of a lysis buffer (1% Nonidet P40; NP-40 in 50 mM Tris-HCl, pH 7.4, 50 mM EDTA, and 1 mM phenyl-methyl-sulfonyl-fluoride; PMSF) and lysed for 15 min. After centrifugation, the cell debris was removed, and a cell lysate was obtained as a supernatant. The cell lysates was used to separate antigens that were recognized by 4B4 or 27B6 antibodies.

Five mg of each of purified 4B4 and 27B6 monoclonal antibodies were dialyzed against a binding buffer (0.2 M sodium bicarbonate, 0.5M sodium chloride, pH 8.3) to afford two different antibody solutions. A 5-ml column packed with 2 ml of NHS-activated sepharose 4 Fast Flow resin (GE Healthcare) was washed with 20 ml of 1 mM HCl and then with 20 ml of a binding buffer (20 mM sodium bicarbonate, 0.5 M sodium chloride, pH 8.3) so as to allow the prepared antibodies to bind to the column. The column was blocked at the outlet thereof, loaded with either of the two different antibody solutions, and blocked at the inlet thereof. Incubation was performed at room temperature for 4 hrs. Then, 20 ml of a washing buffer (20 mM Sodium acetate, 0.5M sodium chloride, pH 5.4) was made to flow through the column so as to remove excess antibodies that were not bound to the resin. Again, the column was washed with 50 ml of a blocking buffer (0.1 M ethanolamine, 0.5 M sodium chloride, pH 8.3) to remove remaining reaction groups. The two columns were washed with 20 ml of a stock buffer (20 mM Tris-HCl, 150 mM NaCl, 0.02% sodium azide, pH 8.0), and refrigerated until use.

The prepared columns were applied to FPLC (Acta FPLC) so that the antibodies bound to the resin could recognize antigens and thus could allow for the separation of the antigens. The lung adenocarcinomic A549 cell line lysates was loaded to the column coupled to FPLC and used as an antigenic source that was recognized by 4B4 and 27B6 monoclonal antibodies. Antigen separation was performed in a four-step process: equilibrium; sample loading; washing and second washing; elution. An equilibrium buffer and a wash buffer have the same composition: 0.5% Tween-80, 20 mM Sodium phosphate, 150 mM sodium chloride, pH 7.4. This buffer was used in an amount of 10 ml for equilibrium and in an amount of 20 ml for washing. An elution buffer contained 0.3 M Glycine, 0.1 M sucrose, 0.1 M Mannitol, 1.0 M urea, and 0.5% Tween-80, had a pH of 3.0, and was used in an amount of 20 ml for washing. For the second washing, a mixture in which the elution buffer was mixed at a ratio of 25% with the washing buffer was employed. 5 ml of TCA was added to 20 ml of the eluted solution obtained during the antigen separation and stored for 30 min in a refrigerator. After centrifugation, the pellet was further washed twice with acetone. The finally obtained pellet was suspended in 1×SDS-PAGE sample buffer, subjected to electrophoresis, and stained with Coomassie blue. As described above, antigens that were isolated and purified through the columns respectively fabricated with 4B4 and 27B6 antibodies are shown in FIG. 6. FIG. 6 shows electrophoretograms of antigens isolated and purified from the lung adenocarcinoma A549 cell line through columns fabricated with 4B4 and 27B6 monoclonal antibodies.

6-2: Identification of Antigen for 4B4 and 27B6 Monoclonal Antibodies

The antigens isolated and purified from the resin coupled with the 4B4 and the 27B6 monoclonal antibody were visualised as shown in FIG. 7. The two main protein bands indicated by the arrows at about 58 kDa were analyzed in Seoul Pharma Laboratories. For identification, peptides were prepared via in-gel digestion and analyzed using LC-MS/MS, followed by processing the MS/MS spectra with PLGS (Waters) and MASCOT (Matrix Science). A series of analyses was conducted as follows.

Gel pieces containing proteins were dehydrated using 100% CAN (acetonitrile) and completely dried in a Speed-vac. The proteins in the dried gel pieces were digested for 15 min with trypsin. The tryptic peptides were extracted with 60% CAN and 0.1% TFA. The pooled extracts were dried in a Speed-vac. The samples were dissolved in 5% CAN, 0.2% TFA (Trifluoroacetic acid) 20 µl prior to LC-MS/MS analysis. Peptides were eluted from the LC column nanoACQUITY UPLC BEH C18 (1.7 µm, 300 Å, 2.1 mm×150 mm I.D.), with a gradient of a mobile phase buffer A (0.1% TFA in 100% DW) to a mobile phase buffer B (0.1% TFA in 100% ACN) in a LC-MS/MS analysis. The separated peptides were analyzed online in a positive survey scan mode on a nano-ESI-Q-TOF instrument. Subsequently, the spectral data were processed with PLGS and MASCOT.

As a result of the above-described series of analyzes, the final identification results are obtained as shown in the following table, and they are shown in Table 8 below.

TABLE 8

| Antibody | No. | Description | mW(Da) | pI(pH) |
|---|---|---|---|---|
| 4B4 | 1 | Actin cytoplasmic 1 | 41739 | 5.15 |
| 4B4 | 2 | Carbonic anhydrase 12 | 39426 | 6.79 |
| 4B4 | 3 | Keratin type I cytoskeletal 9 | 62026 | 4.96 |
| 4B4 | 4 | Serum albumin | 68647 | 5.68 |
| 4B4 | 5 | Trypsin | 24393 | 6.91 |
| 4B4 | 6 | Actin 3 | 41813 | 5.01 |
| 4B4 | 7 | Actin 1 | 41648 | 5.24 |
| 27B6 | 1 | Carbonic anhydrase12 | 39426 | 6.79 |
| 27B6 | 2 | Pyruvate kinase isozymes M1/M2 | 58470 | 7.96 |
| 27B6 | 3 | Actin cytoskeletal 1 | 41814 | 5.24 |
| 27B6 | 4 | Retinal dehydrogenase 1 | 42327 | 5.08 |
| 27B6 | 5 | Hemoglobin subunit beta 1 | 15830 | 7.5 |
| 27B6 | 6 | Synaptic vesicle membrane protein VAT-1 homolog | 42122 | 5.88 |
| 27B6 | 7 | Protein disulfide isomerase | 57146 | 5.98 |
| 27B6 | 8 | Serum albumin | 68647 | 5.68 |
| 27B6 | 9 | Trypsin | 24393 | 6.91 |
| 27B6 | 10 | Actin gamma | 41580 | 5.33 |

As expected, carbonic anhydrase 12 of the analysis results was identified in common from the antigens purified by both the 4B4 and the 27B6 monoclonal antibody, and was found to exist on cell surfaces. The other proteins cannot be antigens for the 4B4 and the 27B6 monoclonal antibody, because they are intracellular proteins. Thus, they seemed to be impurities included due to imperfect separation and purification.

Four peptides were separated by 27B6: QFLLTNNGHSVK (SEQ ID NO: 22), WTYFGPDGENSWSK (SEQ ID NO: 23), GQEAFVPGFNIEELLPER (SEQ ID NO: 24), and YKGQEAFVPGFNIEELLPER (SEQ ID NO: 25). Three peptides were separated by 4B4: QFLLTNNGHSVK (SEQ ID NO: 22), EMINNFR (SEQ ID NO: 26), and GVIYKPATK (SEQ ID NO: 27). Of them, the sequence QFLLTNNGHSVK was analyzed in common in both 4B4 and 27B6. FIG. 8 shows the amino acid sequence of carbonic anhydrase 12 precursor isoform 1, with the analyzed peptide sequence expressed in bold. FIG. 8 lists up the proteins identified by LC-MS/MS analysis from purified antigens. Table 9 shows the amino acid sequence of carbonic anhydrase 12 isoform 1 according to Example 6 and antigenic peptide fragment of the antigens recognized by 27B6 and 4B4 antibody, detected by LC-MS/MS. Such results show that the antigenic peptide fragment of the antigens recognized by 27B6 and 4B4 antibody is carbonic anhydrase 12 isoform 1.

TABLE 9

| CA12 isoform 1 | MPRRSLHAAAVLLLVILKEQPSSPAPVNGSKWT YFGPDGENSWSKKYPSCGGLLQSPIDLHSDILQ YDASLTPLEFQGYNLSANKQFLLTNNGHSVKLN LPSDMHIQGLQSRYSATQLHLHWGNPNDPHGSE HTVSGQHFAAELHIVHYNSDLYPDASTASNKSE GLAVLAVLIEMGSFNPSYDKIFSHLQHVKYKGQ EAFVPGFNIEELLPERTAEYYRYRGSLTTPPCN PTVLWTVFRNPVQISQEQLLALETALYCTHMDD PSPREMINNFRQVQKFDERLVYTSFSQVQVCTA AGLSLGIILSLALAGILGICIVVVVSIWLFRRK SIKKGDNKGVIYKPATKMETEAHA |
|---|---|
| Peptide fragment of antibody recognized by 4B4 | QFLLTNNGHSVK  EMINNFR  GVIYKPATK |
| Peptide fragment of antibody recognized by 27B6 | QFLLTNNGHSVK  WTYFGPDGENSWSK  YKGQEAFVPGFNIEELLPER  GQEAFVPGFNIEELLPER |

6-3: Assay of Antigen for 4B4 and 27B6 Monoclonal Antibodies (ELISA)

To evaluate the antigen identification results obtained by LC-MS/MS, the reactivity of the 4B4 and the 27B6 monoclonal antibody to the recombinant protein carbonic anhydrase 12 (R&D Systems) were examined by ELISA and Western blotting assay.

The recombinant protein CA12 was plated at a density of 100 ng/well into Maxisrop ELISA plates and incubated at 37° C. for 1 hr. To each of the antigen-coated wells, 200 µl of a 1× blocking buffer (Sigma) was added, followed by incubation at 37° C. for 1 hr for blocking. 4B4, 27B6, and an anti-CA12 monoclonal antibody (R&D Systems) were plated, together with 100 µl of PBS, into the plates. After incubation for 1 hr at 37° C., the plates were washed with PBS to remove unbound antibodies. Subsequently, a dilution of goat anti-mouse IgG-HRP (Jackson) was added to the wells, reacted for 30 min, and washed with PBS. Color development was accomplished for 10 min with 50 µl of TMB in each well, and stopped with 50 µl of sulfuric acid. Absorbance at 450 nm was read. Although the reactivity of the 27B6 monoclonal antibody to the recombinant carbonic anhydrase 12 was low, reactivity signals of 4B4, 27B6, and anti-CA12 monoclonal antibody (R&D Systems) against the recombinant antigen are shown in FIG. 7. FIG. 7 shows the identification of carbonic anhydrase 12 as an antigen for the 4B4 and the 27B6 monoclonal antibody, as analyzed by ELISA assay.

6-4: Assay of Antigen for 4B4 and 27B6 Monoclonal Antibodies (Western Blotting)

The recognition of carbonic anhydrase 12 as an antigen by the 4B4 and the 27B6 monoclonal antibody, proven in the previous experiment, was confirmed by Western blotting. The recombinant carbonic anhydrase 12 was boiled for 3 min, loaded into an 8% separating sodium dodecyl sulfate-polyacrylamide gel, and run by electrophoresis. The separated proteins were transferred to a nitrocellulose membrane which was then blocked with 5% skim milk (Sigma) and treated with the 4B4, 27B6, or anti-CA12 monoclonal antibody (R&D Systems) (27B6: lanes 1 and 2, 4B4: lanes 3 and 4, anti-CA12 monoclonal antibody: lanes 5 and 6). After three rounds of washing with a wash buffer (0.1% Tween-20 in PBS), the antibody was coupled with peroxidase-conjugated goat anti-mouse IgG (Sigma, Saint Louis, USA). After the nitrocellulose membrane was washed with a wash buffer, bands were visualized using an enhanced chemiluminescence detection system (ECL, Amersham, Sweden). The results are shown in FIG. 8. FIG. 8 shows the identification of carbonic anhydrase 12 as an antigen for the 4B4 and the 27B6 monoclonal antibody, as analyzed by Western blotting assay. The recombinant CA12 was detected at 40 kDa by all of the 4B4, 27B6, and anti-CA12 monoclonal antibodies (R&D Systems).

6-5: Assay of Antigen for 4B4 and 27B6 Monoclonal Antibodies (Sandwich ELISA)

ELISA and WB assays demonstrated that 4B4 and 27B6 monoclonal antibodies recognize carbonic anhydrase 12 as an antigen, but the detection signal of the 27B6 monoclonal antibody was relatively low. To compensate for the relatively low signal, Sandwich ELISA was conducted as follows. The chimeric 4B4 or 27B6 monoclonal antibody was plated at a concentration of 100 ng/well into Maxisrop ELISA plates and incubated at 37° C. for 1 hr. To each of the antigen-coated wells, 200 μl of 1× blocking buffer (Sigma) was added, followed by incubation at 37° C. for 1 hr for blocking. Two-fold serial dilutions of the recombinant carbonic anhydrase 12 staring from 100 ng/ml were added to wells, incubated at 37° C. for 1 hr, and washed with PBS to remove unbound antigens. Subsequently, the 4B4 monoclonal antibody and the 27B6 monoclonal antibody were added at a concentration of 100 ng/well to chimeric 27B6-coated wells and chimeric 4B4-coated wells, respectively. Following 1 hr of incubation at 37° C., the wells were washed with PBS to remove unbound antibodies. In addition, the bound antibodies were incubated with a dilution of goat anti-Mouse IgG-HRP (Jackson) for 30 min and washed with PBS. Color development was accomplished for 10 min with 50 μl of TMB in each well and stopped with 50 μl of sulfuric acid. The absorbance at 450 nm was detected. When chimeric 27B6 and 4B4 were used as a capture antibody and a detector antibody, respectively, high reaction signals were read, as shown in Table 10. Both of the 4B4 and 27B6 monoclonal antibodies were therefore proven to recognize carbonic anhydrase 12 as an antigen.

Table 10 shows the concurrent recognition of carbonic anhydrase 12 by the 27B6 and 4B4 monoclonal antibodies, as measured by sandwich ELISA assay using the 27B6 and 4B4 monoclonal antibodies as capture/detector antibodies.

TABLE 10

| | Capture antibody | |
|---|---|---|
| | Chimeric 27B6 | Chimeric 4B4 |
| | Detector antibody | |
| | 4B4 mAb | 27B6 mAb |
| CA12 100 ng/ml | 1.653 | 0.021 |
| CA12 50 ng/ml | 1.349 | 0.016 |

TABLE 10-continued

| | Capture antibody | |
|---|---|---|
| | Chimeric 27B6 | Chimeric 4B4 |
| | Detector antibody | |
| | 4B4 mAb | 27B6 mAb |
| CA12 25 ng/ml | 0.954 | 0.016 |
| CA12 12.5 ng/ml | 0.634 | 0.011 |
| CA12 6.25 ng/ml | 0.351 | 0.009 |
| CA12 3.13 ng/ml | 0.193 | 0.008 |
| blank | 0.064 | 0.007 |
| blank | 0.055 | 0.008 |

Example 7: Epitope Mapping

To analyze an epitope, as shown in FIG. 13, recombinant antigen, with or without the epitope, were constructed, and analyzed for immune reactions of mouse monoclonal antibodies of 27B6 and 4B4 in Example 1 and 3.

7-1: Construction and Expression of CA12 Mutant Recombinant Gene

The recombinant vector pSec-Tag-CA 12 full-hFc was digested with BamHI and HindIII to prepare CA12 mutant recombinant genes. A recombinant gene in which a full base sequence of CA12 antigen was fused to hFc was inserted into pSec-Tag which was then allowed to express a recombinant fusion protein containing the full length of CA12 plus hFc. As seen in FIG. 13, deletion mutant-hFc constructs having various lengths within a range from the N terminus to amino acid 300 were prepared.

Respective pSec-Tag vectors carrying the CA12 full-hFc and five different deletion mutant-hFc constructs were introduced into CHO cells with the aid of ViaFect (Promega).

Briefly, one day before transfection, CHO cells were plated and incubated. After the medium was exchanged with a fresh one, a complex of the vector and ViaFect was applied to the CHO cells and incubated for 48 hours. Two days after transfection, the culture supernatant was collected and analyzed for the expression of the gene by detecting human Fc (hFc) through sandwich ELISA.

7-2: Assay of Epitope of Monoclonal Antibody

In order to examine a CA12 epitope recognized by the monoclonal antibodies of the present invention, 50 ng of an anti-human Ig antibody (Jackson Laboratory) was added to each well and incubated at 37° C. for 1 hr. The antibody fixed to the well, which would serve as a capture antibody, was blocked via incubation with 200 μl of a 1× blocking buffer (Sigma) at 37° C. for 1 hr in each well. Each of the respective cultures containing the CA12 full-hFc and the five different deletion mutant-hFc constructs was added at a concentration of 100 μl/well to the plates. Following 1 hr of incubation at 37° C., the wells were washed with PBS to remove unbound antibodies. Subsequently, a dilution of anti-mouse Ig, Fc specific-HRP (Jackson Laboratory) was added to the wells, reacted for 30 min, and washed with PBS. Color development was accomplished for 10 min with 50 μl of TMB in each well, and stopped with 50 μl of sulfuric acid. The absorbance at 450 nm was read. The presence of CA12 mutant-hFc proteins in the culture supernatants was examined using Capture & Detect Sandwich ELISA, with an anti-human Ig antibody serving as a control. The results are given in FIG. 9.

As can be seen in FIG. 9, the epitopes were located in a site from a.a. 25 to a.a. 57, which is a non-catalytic domain. Hence, the antibodies of the present invention do not bind to the catalytic domain of CA-X11, so they do not inhibit the enzymatic activity of CA-XII.

In detail, the epitope specific for the 27B6 antibody was found to have the amino acid sequence APVNGSK<u>WTYFGPD</u> of SEQ ID NO: 2 (the span from 25$^{th}$ amino acid. to 38$^{th}$ amino acid on SEQ ID NO: 5), as analyzed by the deletion method. A three-dimensional crystal structure of CA12 confined the epitope into 7 consecutive amino acids WTYFGPD of SEQ ID NO: 1 (corresponding to 32 to 38 of SEQ ID NO: 5) on the amino acid sequence of SEQ ID NO: 2. Further, the epitope specific for the 4B4 antibody was found to have the amino acid sequence <u>GENSWSKKYPSCGG</u>LLQSP of SEQ ID NO: 4

(the span from 39th to 57th amino acids in SEQ ID NO: 5) while a three-dimensional crystal structure of CA12 confined the epitope into 14 consecutive amino acid sequence GENSWSKKYPSCGG of SEQ ID NO: 3 (corresponding to 39th to 52th amino acids of SEQ ID NO: 5) on the amino acid sequence of SEQ ID NO: 4.

Example 8: Therapeutic Effect of Chimeric Antibody on Solid Tumor (CDC)

8-1: CDC Effect in Lung Adenocarcinomic Cell Line

The lung adenocarcinomic cell line A549 cells were plated at a density of 5×10$^3$ cells/well into 96-well plates and cultured for 20-24 hours in a 37° C., CO$_2$ incubator. After removal of the culture medium from each well, an RPMI medium, free of fetal bovine serum, was mixed with 10% human serum and the chimeric 27B6 antibody was added at a final concentration of 10 μl/ml to a mixture. This solution was plated at a concentration of 100 μl/well into the plates.

The 4B4 chimeric antibody was also treated in the same manner. Following 3 hours of incubation in a 37° C. CO$_2$ incubator, Ez-CyTox agent (DOGEN, KOREA) was added in an amount of 10 μl to each well. Incubation for 3.5 hours in a 37° C., CO$_2$ incubator was followed by measuring absorbance at 450 nm on a plate reader. The results are given in FIG. 10. FIG. 10 shows the complement-dependent cytotoxic effects of the 27B6 antibody.

As can be seen in FIG. 10, the 27B6 and 4B4 chimeric antibodies obtained in Example 2 and 4 exhibit complement-dependent cytotoxicity.

8-2: CDC Effect in Triple-Negative Breast Cancer

According to the same method of <Example 8-1>, the therapeutic effect was evaluated, except that MDAMB-231 of triple-negative breast cancer cell line was used as a target cell instead of A549 cell lines, and absorbance at 450 nm was measured and shown in Table 11. Table 11 shows the results of confirming that the 4B4 chimeric antibody according to Example 8 exhibits complement dependent cytotoxicity in triple negative breast cancer.

TABLE 11

| Sample | Cytotoxicity (%) |
|---|---|
| No treat | 0.0 |
| 5% HS | (12.7) |
| 5% NHS + 4B4 1 ng/ml | 76.5 |
| 5% NHS + 4B4 10 ng/ml | 86.3 |
| 5% NHS + 4B4 100 ng/ml | 83.4 |
| 5% NHS + 4B4 1000 ng/ml | 75.7 |
| 5% NHS + 4B4 10000 ng/ml | 83.7 |

TABLE 11-continued

| Sample | Cytotoxicity (%) |
|---|---|
| 4B4 + 5% NHS + CVF 50 ug | 83.9 |
| 4B4 + 5% NHS + CVF 100 ug | 80.7 |

As shown in Table 11, the 27B6 monoclonal antibody of the present invention exhibited complement-dependent cytotoxicity against lung adenocarcinomic tumors.

Example 9: Therapeutic Effect of Chimeric Antibody in Solid Tumor (ADCC)

9-1: Assay for Antibody-Dependent Cell-Mediated Cytotoxicity (ADCC-LDH Assay)

In order to prepare effector cells, Ficoll was added to a human blood sample (blood:Ficoll=1:2), followed by centrifugation at 2000 rpm for 20 min to obtain PBMCs (Peripheral Blood Mononuclear Cells). The PBMCs were stored at 37° C. in a 5% FBS-supplemented RPMI medium. The antibody-dependent cell-mediated cytotoxicity assay was conducted in conjunction with an LDH assay or a Luciferase assay.

As targets, various solid tumor cell lines—HT29 (colorectal cancer), A549 (lung adenocarcinoma), NCI-H460 (lung adenocarcinoma), and MCF7 (breast cancer)—were each plated at a density of 1×10$^4$ cells/well into 96-well plates and cultured for 18-20 hours in a 37° C., CO$_2$ incubator. After removal of the culture medium from each well, the 27B6 chimeric antibody was added at a concentration of 0 μg/mL, 0.1 μg/mL, or 3 μg/mL to a culture medium supplemented with 5% FBS, and then plated at a concentration of 100 μl/well into the plates, followed by incubation for 30 min in a 37° C. CO$_2$ incubator. Thereafter, the effector cells prepared above were plated at a density of 5×10$^5$ cells/well (50 times as many as the target cells), and cultured for 24 hours in a 37° C. CO$_2$ incubator. For a positive control, a lysis buffer was added before incubation at 37° C. for 24 hours. Following 24 hours of incubation, the cell culture was centrifuged at 2500 rpm for 5 min. The supernatant thus obtained was measured for LDH (lactate dehydrogenase) activity to calculate the cell lysis (Promega assay kit). As shown in FIG. 11, the 27B6 monoclonal antibody of the present invention exhibited antibody-dependent cell-mediated cytotoxicity in various solid tumors (FIG. 11). FIG. 11 shows the antibody-dependent cell-mediated cytotoxic effects of the 27B6 antibody.

9-2: Antibody-Dependent Cell-Mediated Cytotoxicity Assay in Triple-Negative Breast Cancer (ADCC-LDH Assay)

Effector cells were prepared in the same manner as in Example 9-1, and tested for antibody-dependent cell-mediated cytotoxicity.

In addition, the 27B6 antibody was found to exhibit high antibody-dependent cell-mediated cytotoxicity in triple-negative breast cancer cell lines (MDAMB-231, MDAMB-468, MDAMB-453, BT-20) for which no therapeutic agents had yet been developed (FIG. 12). FIG. 12 shows the antibody-dependent cell-mediated cytotoxic effects of the 27B6 antibody on triple-negative breast cancer cell lines.

Example 10: Therapeutic Effect of Defucosylated Antibody in Solid Tumor (ADCC)

10-1: Assay for ADCC of Defucosylated Chimeric 27B6 Antibody—Colon, Lung, Breast Cancer In order to induce the defucosylation of antibody proteins, the 27B6 antibody cell lines of Example 2 and the 4B4 chimeric antibody cell lines of Example 4 were incubated with 100 ng/ml kifunensine which induces the defucosylation of antibody, and the defucosylated antibodies were separated and compared to corresponding fucosylated antibodies. Assay for ADCC of Kifunensine treated, ADCC-Enhanced, Chimeric 27B6 Antibody showed the ADCC effect of defucosylated antibody in Colon cancer, Lung cancer and Breast cancer.

As can be seen in FIG. 13, the antibodies defucosylated by kifunensine were increased in antibody-dependent cell-mediated cytotoxicity against various solid tumor cell lines. FIG. 13 shows the antibody-dependent cell-mediated cytotoxicity of the defucosylated 27B6 chimeric antibody.

10-2: Assay for ADCC of Defucosylated Chimeric 27B6 Antibody—Triple-Negative Breast Cancer By using a luciferase ADCC assay, antibody-dependent cell-mediated cytotoxicity against the triple-negative breast cancer cell line MDAMB231 and the HER2 receptor-positive breast cancer cell line SK-BR3 was analyzed. The antibodies after being defucosylated by treatment with kifunensine exerted higher antibody-dependent cell-mediated cytotoxicity on MDAMB231 and SK-BR-3 than corresponding fucosylated antibodies (FIG. 14).

FIG. 14 shows the antibody-dependent cell-mediated cytotoxicity of defucosylated 4B4 and 27B6 chimeric antibodies, as measured by a luciferase assay.

Specifically, as target cells, the breast cancer cell lines MDAMB231 and SK-BR3 were each plated at a density of $1.25 \times 10^4$ cells/well into 96-well plates and cultured for 20-24 hours in a 37° C. $CO_2$ incubator. After removal of the culture medium from each well, 25 μl of an RPMI medium containing 4% low IgG FBS was added to each well in which the cells were plated. 27B6 and 4B4 antibodies were 3-fold diluted in serial from 10 μg/ml to 1.2 ng/ml in an RPMI medium containing 4% low IgG FBS. The serial antibody dilutions were each added in an amount of 25 μl/well, and the plates were covered with respective lids and left on a clean bench. ADCC reporter cells (ADCC Reporter Bioassay, Promega) were harvested from the cell culture and suspended at a concentration of $3 \times 10^6$ cells/ml in an RPMI medium containing 4% low IgG FBS. To each well was added 25 μl of the suspension of ADCC reporter cells, followed by 24 hours of incubation in a 37° C. $CO_2$ incubator. Before the plates were withdrawn, a frozen luciferase substrate was thawed in a water bath. The plates were removed from the clean bench and left at room temperature for 15 min. The luciferase substrate was added at a concentration of 75 μl/well to the plates and reacted for 30 min in a dark condition, followed by measuring luminescence with a luminometer. The result of antibody-dependent cytotoxicity test of defucosylated 27B6 and 4B4 chimeric antibody using Luciferase assay is shown in FIG. 14.

As seen in FIG. 14, 27B6 and 4B4 antibodies, after being defucosylated by treatment with kifunensine, exerted greater antibody-dependent cell-mediated cytotoxicity on MDAMB231 and SK-BR-3 than did corresponding fucosylated antibodies.

Example 11: Therapeutic Effect of 27B6 and 4B4 Antibodies in Mouse Models 11-1: Cell Line Establishment Animal models with human breast cancer were established using the triple-negative breast cancer cell lines MDA-MB-231 and MDA-MB-453. First, MDA-MB-231 or MDA-MB-453 was subcutaneously injected at a dose of $1.5 \times 10^8$ cells (in RPMI: Matrigel mixture) into the right flank of mice. The injected mice were randomly classified into test and control groups.

FIG. 15 further shows the binding of 27B6 chimeric antibody in Example 2 and 4B4 chimeric antibody in Example 4 to the surface of MDA-MB231 cells utilized in the animal experiment, and FIG. 16 shows the results of the animal experiment using the antibodies, demonstrating that the antibodies suppress the growth and size of MDA-MB231-induced tumor.

As test materials, the 27B6 fucosylated chimeric antibody, 27B6 defucosylated chimeric antibody, 4B4 fucosylated chimeric antibody, and 4B4 defucosylated chimeric antibody were inoculated into breast cancer cells. Three days later, the cells were intraperitoneally injected at a dose of 12 mg/kg to each mouse. Injection was conducted twice a week for three weeks. Tumor sizes were measured just before injection. The inhibitory activity of the anti-CA12 antibodies against breast cancer was expressed as the tumor volume calculated according to the following formula: $(a \times b^2)/2$ (a is the short diameter and b is the long diameter). The volume calculation equation is the same as the volume calculation formula of Example 20-1.

$$\text{Volume calculation equation (volume} = (a \times b)/2, \text{ where } a \text{ is the short diameter and } b \text{ is the long diameter)} \qquad \text{[Equation]}$$

11-2: Inhibitory Activity of Anti CA12 Antibodies Against Triple-Negative Breast Cancer Targeting a CA12 epitope specifically expressed on triple-negative breast cancer, anti-CA12 chimeric antibody 4B4 was assayed for inhibitory activity against triple-negative breast cancer (FIG. 17).

Breast tumors were decreased in volume by 4B4, and the defucosylated antibody was superior in inhibitory activity against tumor growth to the corresponding fucosylated antibody. The inhibitory activity of the 4B4 fucosylated antibody against the growth of breast cancer tumors was found in both MDA-MB-231 and MDA-MB-453.

Particularly, complete remission was observed in the MDA-MB-453 model as the tumor did not grow further after day 21 (FIG. 17). FIG. 17 shows the inhibitory activity of the 4B4 antibodies against triple-negative breast cancer.

Example 12: Effect of Antibody on Cell Survival

The effect of the chimeric 4B4 antibody of Example 4 on cell viability was confirmed. When the antibodies were applied to CA12-positive cancer cells, the effects of the antibodies on cell growth and survival were examined. To this end, cells were plated at a density of $3 \times 10^4$ cells/well into 96-well flat bottom plates one day before application (10% RPMI). After 24 hours, the RPMI was removed, and fresh 5% RPMI containing the antibody was added in an amount of 100 μl to each well.

After 24 hours, a CytoTox 96® Non-Radioactive Cytotoxicity Assay kit (Promega, Cat. #G1780) was plated at a concentration of 50 μl/well and incubated for 30 min at room temperature. Cell viability was measured using a spectrophotometer. Twenty four hours after the antibody was applied to MDA-MB231 cells, the cell viability was measured.

The results of the measurements are shown in FIG. 18. The administration of the antibodies neither promoted nor degraded cell viability. The antibodies did not inhibit CA12 enzymatic activity, and had no influences on tumor cell growth. Therefore, the antibodies according to the present invention were found to exhibit anti-tumor activity via ADCC and CDC through the immune system.

Cell viability was measured 24 hours, 48 hours and 72 hours after the administration of the antibody to A549. No significant changes in cell viability were observed compared to the cells to which no antibodies were administered. FIGS. 19 and 20 show that the binding of the 4B4 antibody alone to tumor cells does not affect the growth of the tumor cells.

The 4B4 antibody, as an anti-CA12 antibody, had no influence on cell growth only when the antibody was bound to cells. This seems to be attributable to the fact that the 4B4 antibody does not affect the enzymatic activity of CA12 because it binds to an N-terminal non-enzymatic region of the CA12 antigen.

Example 13: Evaluation of Therapeutic Effect by Combination of Antibody Therapy and Radiotherapy An examination was made to see whether or not a combination of the antibody of the present invention and radiotherapy could bring about an increased anticancer effect.

Briefly, the 27B6 chimeric antibody of Example 2 was used in combination with 5 μg/ml cisplatin, 2 Gy radiation, or 4 Gy radiation, and A549 cells were analyzed for CA12 expression via flow cytometry. As a result, both cisplatin and radiation were found to increase the expression of CA12 on cell surfaces, with the maximum expression level induced by 4 Gy radiation. This indicates that a combination of the anti-CA12 antibody of the present invention with radiotherapy is able to affect the growth of tumor cells (upper diagram in FIG. 20).

To assay the effect of the combined therapy on the growth of tumor cells, as shown in the lower diagram of FIG. 20, the viability of the cancer cell line A549 was measured via an MIT assay after it was treated with a combination of the 27B6 antibody and radiotherapy. In FIG. 20, the lower graph shows the effects of a combination of the 27B6 antibody and radiotherapy on cell viability. As can be seen in FIG. 20, a combination of 27B6 and radiotherapy induced cell death at higher rates, compared to the antibody alone or a combination of an isotype control antibody and radiotherapy.

Example 14: Humanization of Anti-CA-XII Chimeric Antibody 14-1: Construction of Humanized Variable Domains (DNP004 scFv Form Selection)

The 4B4 chimeric antibody in the full IgG form obtained in Example 4 was transformed into the scFv form for antibody screening by using the phage display technology possessed by the D.H. lap. For this, the variable region of chimeric 4B4 antibody was changed to E. coli codon and the scFv gene was constructed by linking VL and VH with PCR. The order of VL and VH sequence and linker length were combined to construct various constructs and ligated to phagemid vector. The ligated plasmid vector was analyzed by binding assay with antigen CA XII, and VH-long linker-VL form of DNP004 scFv was selected and used as a mutagenesis template.

14-2: Sub-Library Construction and Screening 11 random mutation sub-libraries or position specific mutation sub-libraries were prepared for all or part of the variable region through the know-how of D.H. Lab. The types of sub-libraries produced are as follows:

(1) Random mutation sub-library: 1 kind of VL, 1 kind of VH, 2 kinds of VH&VL, and (2) Position specific mutation sub-library: three kinds of LCDR, three kinds of HCDR, and 1 kind of VH&VL.

Bio-panning of CA XII was performed on the eleven (11) sub-libraries. From the first screening, 552 clones to have high signal in the VL region were selected. Secondary screening was performed to select 78 clones to have higher than the signal of the mother clone. A total of 32 clones with different polynucleotide sequences were selected after confirming the polynucleotide sequence.

Figure 22:
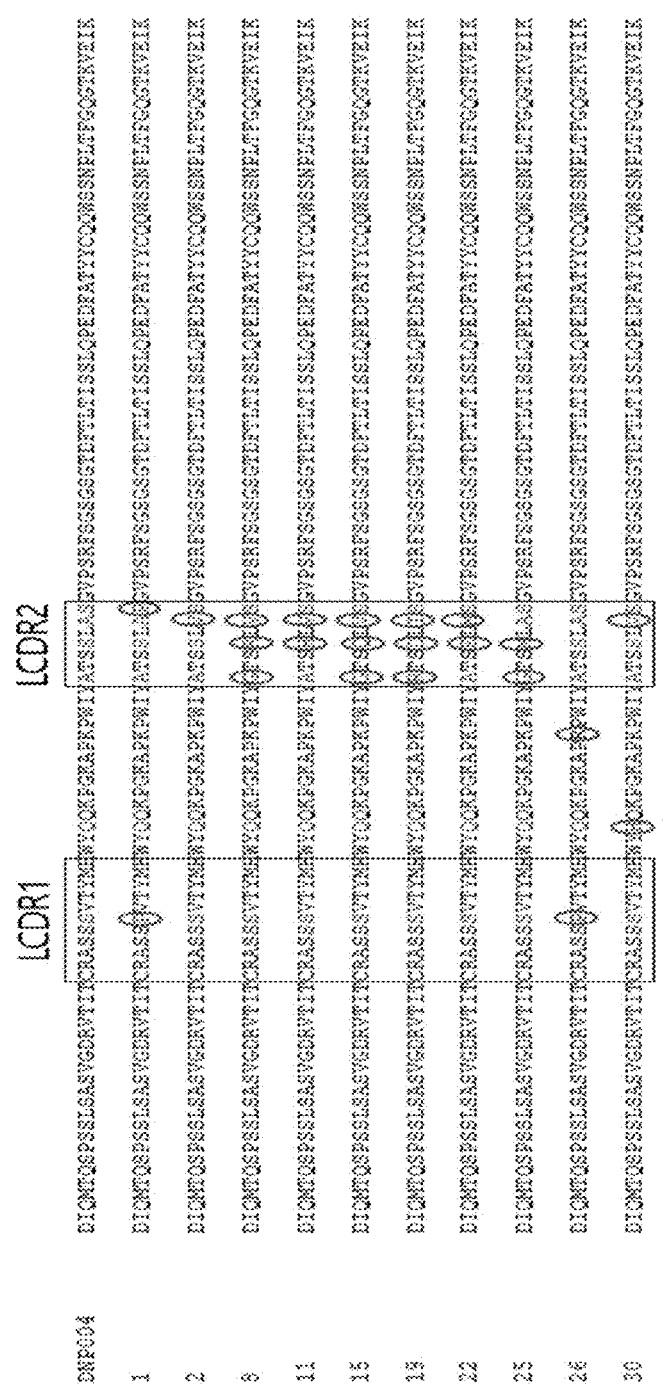

The selected 32 clones were reaffirmed their binding affinity to CA XII by ELISA, and 10 clones (clone ID 1, 2, 4, 5, 8, 15, 24, 25, 26, 28) with an ELISA signal greater than 1.5 times of the 4B4 chimeric antibody were selected. As a result of sequence analysis of their CDRs, it was confirmed that there were mutations in the LCDR1 and LCDR2 regions (FIG. 22).

Then, the LCDR1 and LCDR2 portions are judged as hot-spot, and the 10 clones (clone ID: 1, 2, 4, 5, 8, 15, 24, 25, 26, 28) and additional 4 clones having mutations in LCDR2 portion (clone ID: 11, 22, 19, 30) were selected and then conversed to be full IgG (LK sun, P Curtis, Chimeric antibody with human constant regions and mouse variable regions directed against carcinoma-associated antigen 17-1A, Proc Natl Acad Sci US A. 1987 January; 84 (1): 214-8] (FIGS. 21 and 22). However, clone IDs: 4, 5, 24, and 28 among 14 clones were excluded from further material testing because of low expression. The mutation sites of the ten selected clones are summarized in Table 12 below.

TABLE 12

| Clone ID | Sub-library | | Mutation position |
| | random | selected | |
| --- | --- | --- | --- |
| #1 | ○ | | VL-CDR1, VL-CDR2 |
| #2 | ○ | | VL-CDR2 |
| #4 | ○ | | VL-FR1 |
| #5 | | ○ | VL-CDR1, VL-CDR2 |
| #8 | | ○ | VL-CDR2 |
| #15 | | ○ | VL-CDR2 |
| #24 | | ○ | VL-CDR2 |
| #25 | ○ | | VL-CDR2 |
| #26 | ○ | | VL-CDR1, VL-FR1 |
| #28 | | ○ | VL-FR1 |

14-3: Transfection of Humanized Library and Culture and Measurement of IgG

CHO cells were inoculated into 96-well plates and transfected with mini-preparative DNA of humanized clones. The detailed experimental method is as follows.

First, before 12 hours of transfection, CHO cell line was inoculated into a 6-well plate at a concentration of 1×10⁵ cells/ml, and 3 ml of DMEM containing 5% fetal calf serum was added and cultured at 37° C. in 5% $CO_2$ for 12 hours. Ten kinds of Full IgG DNA were transformed into prepared CHO cells using a ViaFect reagent kit (Promega, USA). Cell culture supernatants were collected 48 hours after transfection and the reactivity of each humanized clone and control IgG antibody were confirmed by ELISA.

100 ng of recombinant protein CA XII per well was added to the Maxisrop ELISA plate and reacted at 37° C. for one hour to coat the antigen. Then, 1× blocking solution (Sigma) was added to 200 μl per well and blocked for reaction at 37° C. for one hour. 4B4, 27B6, anti-CA XII monoclonal antibody (R&D Systems) and PBS 100 ul were added to the prepared plate, incubated at 37° C. for 1 hour and washed with PBS to remove the unbound antibodies. Then, the reaction was added with diluted Goat anti-Human IgG-HRP (Jackson), incubated for 30 minutes, washed with PBS, reacted with TMB solution at an amount of 50 ul per well for 10 minutes, and the reaction was quenched with addition of 50 ul of sulfuric acid. The absorbance of product was measured at 450 nm.

14-4: Antigen Affinity Test for Candidate Humanized Antibody Using ELISA

The parallel test on the binding of humanized clones to antigen CA-XII was carried out by using the protocols and antigens provided in the D.H Lab. Activity (affinity) was calculated for each clone and compared to the activity of the positive control (chimeric clone 4B4) on the same plate. The antigen binding affinity of 10 variants (clone ID 1, 2, 4, 5, 8, 15, 24, 25, 26, 28) was not significantly higher than that of the mother clone (4B4 chimeric). The expected affinity of the mother clone analyzed by ELISA was about KD $10^{-10}$ M, which is quite high. Thus, it is considered that the binding force of 10 candidate antibodies is not low even if the antigen binding affinities of the candidate clones do not reach the mother clone (FIGS. 23 and 24).

Example 15: CDR Sequence/Antibody Sequence of Humanized Antibody 15-1: Selection of Gene Sequence of Anti-DNP004 Humanized Antibody The DNP004 humanized antibody gene was prepared by using a light chain variable region gene and heavy chain variable region gene of mouse monoclonal antibody 4B4 (hybridoma deposited as an accession number: KCLRF-BP-00279) specifically binding to CA-XII as a template to prepare a humanized antibody, 10 random mutation sub-libraries or position specific mutation sub-libraries were prepared for all or part of the variable region through the in silico know-how of D.H. Lab 552 clones were screened by phage display technique using the constructed library, and 78 clones showing higher signal than mother clone were screened. 32 different clones were screened according to the nucleotide sequence analysis. As a result of analysis for 32 clones for the binding affinity to CA XII, 10 clones were selected, when ELISA signal was more than 1.5 times as high as that of mother clone, and the mutation sites were largely in LCDR1 and LCDR2 regions. Therefore, LCDR1 and 2 were selected as hot-spot, and 4 kinds (Clone ID: 11, 22, 19, 30) with mutation in LCDR2 region were selected to perform full IgG1 conversion. Among the prepared 14 IgGs, clone IDs 4, 5, 24, and 28 were excluded for low expression, and remnant 10 clones were expressed and purified, and finally ELISA was performed to select the final 10 species.

Finally, humanized antibody #8 candidate that was mostly similar to mouse monoclonal antibody 4B4 were selected. The humanized antibody genes for each candidate antibody were identified by sequencing. The heavy chain variable region sequences and light chain variable region sequences of the analyzed DNP004 antibody are as follows (Tables 13 and 14). As shown in Table 13 below, the CDR sequences of the heavy chain variable region may be the same or partly different, but the CDR sequences of the light chain variable region may be different. The amino acids expressed in bold in SEQ ID NOs: 15, 16, 28, and 32 to 42 below are modified.

TABLE 13

| Clone ID no.. | CDR1 | SEQ ID NO | CDR2 | SEQ ID NO | CDR3 | SEQ ID NO |
|---|---|---|---|---|---|---|
| $V_{H-chimeric}$ | GYSYTDYN | 14 | IDPANGDT | 15 | ARPIYYGAY WYFDV | 16 |
| $V_{H-humanized}$ | GYSYTDYN | 14 | IDPANGDT | 15 | SRPIYYGAY WYFDV | 28 |
| $V_{L-chimeric}$ | KSLLHSNG NTY, | 17 | RMS | 18 | MQHLEYPFT | 19 |
| $V_{L-humanized}$ General formula | ASS$\underline{X_1}$VTY | 29 | $X_2$TS$X_3$L$X_4X_5$ | 30 | QQWSSNPLT | 31 |
| #1-$V_L$ | ASSPVTY | 32 | ATSSLAP | 34 | QQWSSNPLT | 31 |
| #2-$V_L$ | ASSSVTY | 33 | ATSSLVS | 35 | QQWSSNPLT | 31 |
| #8-$V_L$ | ASSSVTY | 33 | GTSRLVS | 36 | QQWSSNPLT | 31 |
| #11-$V_L$ | ASSSVTY | 33 | ATSHLVS | 37 | QQWSSNPLT | 31 |
| #15-$V_L$ | ASSSVTY | 33 | GTSQLVS | 38 | QQWSSNPLT | 31 |
| #19-$V_L$ | ASSSVTY | 33 | RTSDLIS | 39 | QQWSSNPLT | 31 |
| #22-$V_L$ | ASSSVTY | 33 | ATSELMS | 40 | QQWSSNPLT | 31 |
| #25-$V_L$ | ASSSVTY | 33 | GTSMLAS | 41 | QQWSSNPLT | 31 |
| #26-$V_L$ | ASSPVTY | 32 | ATSSLAS | 42 | QQWSSNPLT | 31 |
| #30-$V_L$ | ASSSVTY | 33 | ATSSLVS | 35 | QQWSSNPLT | 31 |

TABLE 14

| | | |
|---|---|---|
| Frame work #1 of $V_{H-humanized}$ | EVQLVESGGGLVQPGG SLRLSCAAS | 43 |
| Frame work #2 of $V_{H-humanized}$ | IYWVRQAPGKGLEWVG Y | 44 |
| Frame work #3 Of $V_{H-humanized}$ | TYNQKFKGRATISVDK SKNTAYLQMNSLRAED TAVYYC | 45 |
| Frame work #4 of $V_{H-humanized}$ | WGQGTLVTVSS | 46 |
| Frame work #1 of $V_{L-humanized}$ | DIQMTQSPSSLSASVG DRVTITCR | 47 |
| Frame work #3 of $V_{L-humanized}$ | GVPSRFSGSGSGTDFT LTISSLQPEDFATYYC | 51 |
| Frame work #4 of $V_{L-humanized}$ | FGQGTKVEIK | 52 |
| Frame work #2 of $V_{L-humanized}$ | General formula | MHWY$X_6$QKPGKAP$\underline{X_7}$PWIY (X6 = Q or H; H7 = R or K) | 48 |
| | #26-$V_L$ | MHWYQQKPGKAPRPWIY | 49 |
| | #30-$V_L$ | MHWYHQKPGKAPKPWIY | 50 |

In Table 15 below, the heavy chain variable region sequence and light chain variable region sequence of the selected clones are shown, all the heavy chain variable regions are identical (SEQ ID NO: 53), but the light chain variable regions are different (SEQ ID NOS: 54 to 63). The underlined part of sequence corresponds to the CDR sequence.

TABLE 15

| Clone ID no. | Amino acid sequence | SEQ ID NO |
|---|---|---|
| $V_H$ | EVQLVESGGGLVQPGGSLRLSCAASGY SYTDYNIYWVRQAPGKGLEWVGYIDPA NGDTTYNQKFKGRATISVDKSKNTAYL QMNSLRAEDTAVYYCSRPIYYGAYWYF DVWGQGTLVTVSS | 53 |
| #1-$V_L$ | DIQMTQSPSSLSASVGDRVTITCRASS PVTYMHWYQQKPGKAPKPWIYATSSLA PGVPSRFSGSGSGTDFTLTISSLQPED FATYYCQQWSSNPLTFGQGTKVEIK | 54 |
| #2-$V_L$ | DIQMTQSPSSLSASVGDRVTITCRASS SVTYMHWYQQKPGKAPKPWIYATSSLV SGVPSRFSGSGSGTDFTLTISSLQPED FATYYCQQWSSNPLTFGQGTKVEIK | 55 |
| #8-$V_L$ | DIQMTQSPSSLSASVGDRVTITCRASS SVTYMHWYQQKPGKAPKPWIYGTSRLV SGVPSRFSGSGSGTDFTLTISSLQPED FATYYCQQWSSNPLTFGQGTKVEIK | 56 |
| #11-$V_L$ | DIQMTQSPSSLSASVGDRVTITCRASS SVTYMHWYQQKPGKAPKPWIYATSHLV SGVPSRFSGSGSGTDFTLTISSLQPED FATYYCQQWSSNPLTFGQGTKVEIK | 57 |
| #15-$V_L$ | DIQMTQSPSSLSASVGDRVTITCRASS SVTYMHWYQQKPGKAPKPWIYGTSQLV SGVPSRFSGSGSGTDFTLTISSLQPED FATYYCQQWSSNPLTFGQGTKVEIK | 58 |
| #19-$V_L$ | DIQMTQSPSSLSASVGDRVTITCRASS SVTYMHWYQQKPGKAPKPWIYRTSDLI SGVPSRFSGSGSGTDFTLTISSLQPED FATYYCQQWSSNPLTFGQGTKVEIK | 59 |
| #22-$V_L$ | DIQMTQSPSSLSASVGDRVTITCRASS SVTYMHWYQQKPGKAPKPWIYATSELM SGVPSRFSGSGSGTDFTLTISSLQPED FATYYCQQWSSNPLTFGQGTKVEIK | 60 |
| #25-$V_L$ | DIQMTQSPSSLSASVGDRVTITCRASS SVTYMHWYQQKPGKAPKPWIYGTSMLA SGVPSRFSGSGSGTDFTLTISSLQPED FATYYCQQWSSNPLTFGQGTKVEIK | 61 |
| #26-$V_L$ | DIQMTQSPSSLSASVGDRVTITCRASS PVTYMHWYQQKPGKAPRPWIYATSSLA SGVPSRFSGSGSGTDFTLTISSLQPED FATYYCQQWSSNPLTFGQGTKVEIK | 62 |
| #30-$V_L$ | DIQMTQSPSSLSASVGDRVTITCRASS SVTYMHWYHQKPGKAPKPWIYATSSLV SGVPSRFSGSGSGTDFTLTISSLQPED FATYYCQQWSSNPLTFGQGTKVEIK | 63 |

15-2: Preparation of Humanized Antibody

Based on the amino acid sequence of the prepared anti-CA-XII humanized antibody DNP004, a humanized antibody was prepared For the expression of anti-CA-XII humanized antibodies, a plasmid for expression of heavy chain and a plasmid for light chain expression were respectively prepared. PcDNA3.4 (Invitrogen) vector was used as the heavy chain expression plasmid, and pOptiVEC (Invitrogen) vector was used as the light chain expression plasmid.

In order to express the variable region coding cDNA and the constant region coding cDNA of each antibody as a continuous amino acid sequence without inserting additional amino acid, the coding sequence of the cloned variable region and the known human IgG1 constant region (heavy chain) and the kappa constant region (light chain) coding sequences were synthesized (Bioneer). The synthesized heavy chain genes and light chain genes were digested with restriction enzymes Xho I and Sal I, and the heavy chain gene fragment was ligated to the pcDNA3.4 vector and the light chain gene fragment was ligated to the pOptiVec vector to construct a complete antibody expression plasmid (pcDNA3.4-4B4 heavy chain expression plasmid and pOptiVEC-4B4 light chain expression plasmid).

The prepared pcDNA3.4-4B4 heavy chain expression plasmid and the pOptiVEC-4B4 light chain expression plasmid were transfected into CHO cell-derived DG44 cells (Invitrogen) to perform transformation.

Three days prior to transfection, DG44 cells in suspension were adapted to MEMa medium containing 5% FBS to convert them into adherent cells and to improve transfection efficiency. Transfection was performed on a 6-well plate using the ViaFect transfection regent (Promega, Cat. #: E4981). On the day before the transfection, DG44 cells adapted to the adhered state were prepared by sub-culturing at a concentration of $1 \times 10^5$ cells/well. The amount of DNA used for transfection was determined by using 3 μg of the pOptiVEC-4B4 light chain expression plasmid and 1 μg of the pcDNA3.4-4B4 heavy chain expression plasmid at 3:1 mixing ratio. Transfection was carried out for 48 hours. Flow cytometry was used to analyze the transfected cell population.

FIG. 25 shows the binding of the humanized antibody DNP004 in the CA-XII positive triple negative breast cancer cell line MDAMB-231.

Example 16: Evaluation of Physical Properties of Antibody Candidate Group

SDS-PAGE analysis, Size exclusion chromatography, Melting temperature, ANS reactivity, etc. were evaluated and compared in order to compare the expression and physical properties of humanized antibody variants.

16-1: Antibody Candidate Group—Analysis of Expression Level

In order to confirm the expression level and the occurrence of precipitation by protein A purification, transient transfection was induced by introducing a combination vector of 8 mutants into HEK293F.

300 mL of each culture was injected into protein A (GE Helthcare, Cat. No. 11-003493) and purified using elution buffer (20 mM citric buffer, pH 3.0). The obtained antibody was dialyzed with phosphate buffered saline and quantified before and after dialysis to confirm the loss. The expression levels were very different in the range of 1.0~10.0 μg/mL, and high expression rates were observed in variant number of 25 and 26 (Table 16).

TABLE 16

| Clone Number | The expression amount before dialysis (mg) [expression amount per unit volume] | The expression amount after dialysis (mg) |
|---|---|---|
| Humanized antibody variant #1 | 0.6 [2.0 μg/mL] | 0.6 |
| Humanized antibody variant #2 | 2.5 [8.33 μg/mL] | 2.5 |
| Humanized antibody variant #8 | 1.5 [5.0 μg/mL] | 1.2 |
| Humanized antibody variant #11 | 1.5 [5.0 μg/mL] | 1.3 |
| Humanized antibody variant #15 | 0.3 [1.0 μg/mL] | 0.3 |
| Humanized antibody variant #19 | 1.2 [4.0 μg/mL] | 1.0 |
| Humanized antibody variant #22 | 0.5 [1.67 μg/mL] | 0.5 |
| Humanized antibody variant #25 | 2.7 [9.0 μg/mL] | 2.7 |
| Humanized antibody variant #26 | 3.0 [10.0 μg/mL] | 3.0 |
| Humanized antibody variant #30 | 1.5 [5.0 μg/mL] | 1.5 |

16-2: SDS-PAGE Analysis of Antibody Candidates

SDS-PAGE analysis was performed to evaluate the completeness of heavy/light chain binding of the humanized antibody variants, unity of the heavy chain and light chain.

In the non-reducing assay, 5 µg of the antibody was reduced, 10 µg of the antibody was mixed in 2× Laemmli sample buffer (Bioread, Cat. No. 161-0737), boiled at 100° C. for 5 minutes and ini-PROTEAN TGX gel Bio-Rad, Cat. No. 456-1083). Electrophoresis was carried out at 150 V for 1 hour and stained with SimplyBlue Safestain (Invitrogen, Cat. No: LC6060) for 2 hours and desalted with distilled water. Among the eight humanized antibody variants, light chain staining was unclear for the clone #15 variants, but none of the other 7 variants were found to be abnormal (FIG. 26).

FIG. 26 is a photograph showing the result of analyzing the physical properties of the candidate antibody group using SDS-PAGE. Among 15 variants of the humanized antibody variants, light chain staining was unclear for the clone #15 variants, but none in the other 7 variants (FIG. 26).

16-3: SE-HPLC Analysis of Antibody Candidates

Size exclusion-chromatography analysis was performed for purity evaluation.

Each antibody was diluted with phosphate-buffered saline to prepare 1.0 mg/mL and injected 20 µL into TSKgel G3000SWXL (TOSOH) equilibrated with equilibrium buffer (0.1 M sodium phosphate, 0.1 M sodium chloride pH 7.0). The equilibrium buffer was flowed at a flow rate of 0.5 mL/min for 40 minutes, and the eluted protein was detected at a wavelength of 280 nm. The detected peaks were integrated by automatic analysis to calculate the area for each peak, and the area ratio of the main peak was described as a percentage.

The major peak area ratio of most variants was 95% or more than of purity, but variants #11 and #26 were 94.3% and 94.1%, respectively, which are somewhat lower (Table 17).

TABLE 17

| Clone number | Retention time(min) | Main peak Area ratio (%) |
| --- | --- | --- |
| The chimeric antibody (4B4) | 15.99 | 98.3402 |
| Humanized antibody variant # 1 | 16.366 | 95.325 |
| Humanized antibody variant # 2 | 16.326 | 95.0894 |
| Humanized antibody variant # 8 | 16.332 | 95.1814 |
| Humanized antibody variant # 11 | 16.409 | 94.3005 |
| Humanized antibody variant # 15 | 16.307 | 96.8589 |
| Humanized antibody variant # 19 | 16.263 | 97.4621 |
| Humanized antibody variant # 22 | 16.158 | 96.7872 |
| Humanized antibody variant # 25 | 16.329 | 95.3279 |
| Humanized antibody variant # 26 | 16.361 | 94.1417 |
| Humanized antibody variant # 30 | 16.326 | 95.735 |

16-4: Antibody Candidate Group—Melting Temperature (Tm) Analysis

For comparative evaluation of the robustness, the Melting temperature of humanized antibody variants was measured.

Protein thermal shift dye and buffer (Invitrogen, Cat. No. 4462263) were added to 0.44 µg of antibody variant according to the manufacturer's manual to prepare 20 µL of the mixed solution, which was injected into Real time PCR equipped with Protein Thermal Shift™ Software v1.0. Fluorescence values detected by binding between the protein thermal shift dye and the antibody were detected while increasing the temperature continuously from 25° C. to 95° C. at a rate of 0.05° C./sec. After completion of the test, the Boltzmann fitting was implemented with ViiA™ 7 Software and the melting temperature (Tm) for each antibody was calculated. For mutant 8, Tm was the most robust antibody at 71.41° C. In order to confirm the correlation between Tm and purity, each mutant was allowed to stand at 62° C. for 3 hours at high temperature and then subjected to size exclusion chromatography analysis to calculate the area ratio of the main peak.

The variant 8 showed the highest peak-to-peak ratio at the high temperature of 62° C. and was the most robust variant with the same Tm analysis (Table 18).

TABLE 18

| Clone number | Melting temperature (° C.) | Main peak Area ratio (%) |
| --- | --- | --- |
| Humanized antibody variant # 2 | 69.96 | 89.534 |
| Humanized antibody variant # 8 | 71.41 | 94.684 |
| Humanized antibody variant # 19 | 66.93 | 83.662 |
| Humanized antibody variant # 22 | 68.59 | NA |
| Humanized antibody variant # 30 | 70.01 | 88.852 |

16-5: Evaluation of the Binding Strength of CA XII Positive Cell Line

MDAMB231 breast cancer cell line expressing CA XII antigen was cultured in RPMI 1640 (GIBCO, Invitrogen) supplemented with 10% heat inactivated FBS, desorbed with trypsine-EDTA (Invitrogen), washed with phosphate buffered saline, and poured to tube at an amount of $2 \times 10^6$ cells/tube.

Humanized antibody variants were added to each tube to a concentration of 1.0 µg/mL and reacted for 30 min at refrigeration. FITC-labeled secondary antibody Goat anti-Mouse IgG (HL)-FITC (DINONA INC, Korea) was added and the cells were reacted for 20 minutes in the refrigerator. The cells were centrifuged once more with phosphate-buffered saline, the cells were suspended in phosphate-buffered saline containing 1% formaldehyde, and the fluorescence was analyzed with a flow cytometer (Stratedigm, S1000EXi).

The binding strength of the mutants based on the Mean Fluorescence Intensity (MFI) of the 4B4 chimeric antibody bound to the MDAMB231 cell line is shown in FIG. 28 as a percentage. All variants showed a relative binding strength of 90% or more, and variants 8, 11, 15, and 26 showed 99% of relative binding strength, which there is no little difference from the chimeric antibody (FIG. 27).

Example 17 Analysis of Humanized Antibody Expression in Various Cell Lines 17-1: Antibody Expression in Various Cell Lines The binding of humanized antibody (DNP004) in various cancer cell lines obtained from KCLB (Korean Cell Line Bank) and SNU (Seoul National University) was confirmed by flow cytometry. LNCap, MCF-7, Huh7 and Hs-578T were cultured in Dulbecco's MEM (GIBCO, Invitrogen) supplemented with 10% heat-inactivated fetal bovine serum (FBS; GIBCO, Invitrogen) and A549, NCI-H460, DLD-1, HT-29, LS174T, PC-3, SNU638, SNU719, MKN45, NCI-H87, SK-BR3, MDA-MB231, MDA-MB453 were cultured in RPMI 1640 (GIBCO, Invitrogen) medium supplemented with 10% heat-inactivated FBS at 37° C. in a 5% CO2 incubator. In addition, Hep3B.1-7 and PLC/PRF/5 were cultured in Eagle's MEM (GIBCO, Invitrogen) medium supplemented with 10% heat inactivated fetal bovine serum (FBS; GIBCO, Invitrogen) and KATO III was were cultured in IMDM (GIBCO, Invitrogen) medium supplemented with 20% heat inactivated fetal bovine serum (GIBCO, Invitrogen) at 37° C. in a 5% CO2 incubator.

After incubation with DNP004 at 4° C. for 30 minutes, the cancer cells were washed with PBS, and FITC-conjugated goat anti-Huma IgG (DINONA INC, Korea) was added to the cultured cancer cells. Min. After washing with PBS, the cells were analyzed with FACS caliber (Becton Dickinson, USA) and the results are shown below (Table 19). Table 19 below shows the expression patterns of the carbonic anhydrase 12 antigen in various solid cancer cell lines. In Table 19, the percentage of DNP004-positive cells was analyzed by FACS analysis. The number of cells that bind to DNP004 antibody among the 5000 cells to be tested was calculated as %; − refers to less than 10% of the number of positive cells, + refers to 10 to 30% of the number of positive cells, ++ refers to 30 to 70% of the number of positive cells, and +++ refers to 70 to 100% of the number of positive cell.

TABLE 19

| Origin | Cell line | 4B4 chimeric | DNP004 |
|---|---|---|---|
| Lung | A549 TA | +++ | +++ |
|  | NCl-H460 | ++ | ++ |
| Colon | DLD-1 | − | + |
|  | HT-29 | + | +++ |
|  | LS174T | +++ | +++ |
| Stomach | SNU 638 | − | + |
|  | SNU719 | ++ | ++ |
|  | KATO III | − | +++ |
|  | MKN 45 | +++ | +++ |
| Liver | Huh-7 | ++ | +++ |
|  | Hep3B.1-7 | + | + |
|  | PLC/PRF/5 | +++ | +++ |
| Prostate | LNCap | + | − |
| Kidney | 786-O | +++ | +++ |
| Breast | MCF-7 | + | ++ |
|  | SK-BR3 | +++ | ++ |
|  | MDAMB231 | +++ | +++ |
|  | MDAMB453 | ++ | +++ |
|  | Hs-578T | − | ++ |
| PBMC | Lymphocyte | − | − |
|  | Monocyte | − | − |
|  | Granulocyte | − | − |

As shown in Table 19, even though the cells having the same origin have different tissue sources used in the cell line construction, the degree of positive reaction may vary depending on the type of the cells. However, the humanized antibody DNP004 of the present invention showed the positive reaction to a variety of types of adenocarcinoma of the lung, colon cancer, stomach cancer, liver cancer, and breast cancer cell line, even though the degree of positive reaction is somewhat different, but showed negative reaction in prostate cancer. On the other hand, peripheral blood lymphocytes, mononuclear cells and granulocytes were found to be negative. These results indicate that the humanized antibody DNP004 of the present invention can be used as a therapeutic agent for indications of solid tumors exhibiting a positive reaction.

17-2: Expression Patterns in Various Types of Breast Cancer Cells

DNP004 antibody is positive in both ER and PR as well as in HER2 positive breast cancer cells. Thus, the antibody of present invention can be used for the triple negative breast cancer, as well as various types of breast cancer treatment. The binding of DNP004 humanized antibodies in three different phenotypic breast cancer cell lines was confirmed by flow cytometry and the differences in the degree of binding with chimeric 4B4 were compared.

Specifically, MDAMB-231 and MDAMB453, MCF-7 and SK-BR-3 cell lines were cultured in the same manner as in Example 5-2. DNP004 humanized antibody was added to each cultured cancer cell lines. The cells were incubated at 4° C. for 30 minutes, washed with PBS, and incubated at 4° C. for 15 minutes with FITC-conjugated goat anti-Human IgG (DINONA INC, Korea). The cells were washed again with PBS and analyzed with FACS caliber (Becton Dickinson, USA), and the results are shown in FIGS. 28 and 29.

FIGS. 28 and 29 show the results of binding tests of DNP004 humanized antibodies against the carbonic anhydrase 12 antigen in various types of breast cancer cells. Therefore, the DNP004 humanized antibody according to the present invention can be used not only for triple negative breast cancer but also for various types of breast cancers, since it is positive in both ER and PR as well as HER2-positive breast cancer cells.

Example 18: Therapeutic Effect (ADCC) of Humanized Antibodies Against Various Solid Tumors Antibody-dependent cytotoxicity (ADCC) was evaluated by Luciferase assay in various solid tumors. MDAMB-231 and MDAMB-453, SK-BR3, lung cancer cell line A549, liver cancer cell line Huh7 and HEP3B, and gastric cancer cell lines KATO III, SNU719 and MKN-45 were inoculated at $1.25 \times 10^4$ cells/well, and incubated at 37° C. in a CO2 incubator for 20-24 hours. After removing the culture medium from each well, 25 µl of RPMI containing 4% low IgG FBS were added to the plated wells. DNP004 humanized antibody of Example 15 was diluted with RPMI containing 4% low IgG FBS, at 3-fold to range from a maximum concentration of 10 µg/ml to 1.2 ng/ml. Each prepared antibody sample was added to the corresponding wells at the respective concentrations, and the lid of the plate was closed and kept in a clean bench. The cultured ADCC reporter cell (ADCC Reporter Bi 5 assay, Promega) was harvested and suspended in RPMI containing 4% of low IgG FBS at $3 \times 10^6$ cells/ml. 25 µl of ADCC reporter cell suspension was added to each well and cultured in at 37° C. in $CO_2$ incubator for 24 hours.

The luciferase substrate, which has been frozen in advance, was prepared by melting it in a hot water bath. The plate was left for 15 minutes at room temperature. After adding 75 µl of luciferase substrate to each well, the reaction was occurred for 30 minutes in a dark room and the luminous intensity was measured using a luminometer.

FIG. 30 shows the result of antibody-dependent cytotoxic effect of DNP004 humanized antibody in breast cancer cell line, FIG. 31 shows the result of antibody-dependent cytotoxic effect of DNP004 humanized antibody in lung cancer cell line A549, FIG. 32 shows DNP004 humanized antibody-dependent cytotoxic effect in Huh7 and HEP3B, and FIG. 33 shows the results of confirming antibody-dependent cytotoxic effect of DNP004 humanized antibody in gastric cancer cell lines KATO III, SNU719 and MKN-45.

Thus, the DNP004 humanized antibody of the present invention was proven to have a cell apoptotic mechanism by antibody-dependent cytotoxic effect in various types of solid cancer cells expressing antigen of DNP004 (CA XII, Carbonic anhydrase XII).

Example 19 Evaluation of Therapeutic Effect of Humanized Antibody Using Mouse Experimental Model 19-1: Breast Cancer Animal Model/Antibody-Administered Group with Single Concentration Human breast cancer animal models were established with the MDA-MB-453 cell line of a triple negative breast cancer cell line. First, 1.5×10⁷ cells of MDA-MB-453 were subcutaneously inoculated into the right flank of the mouse, tumor formation and growth were observed, and the tumor size was calculated by the following equation.

(Volume=$(a \times b)/2$, $a$ is a short diameter, and $b$ is a long diameter)

When the tumor size reached 100 mm³±20, mice were randomly divided into a control group (5 rats) and a treatment group (5 rats), and a DNP004 humanized antibody was administered to mouse tail vein at a dose of 10 mg/kg. Then, the tumors were measured twice a week at intervals of 3-4 days during the experiment period, and tumor growth curves were taken from the start of antibody administration to the end of the experiment, and the average values of the results are shown in FIG. 34a. Thus, the group treated with humanized antibody showed the inhibitory effect on the most of tumor growth (FIG. 34).

19-2: Breast Cancer Animal Model/Antibody-Administered Group with Multiple Concentrations Experiments were conducted to administer DNP004 humanized antibody at various concentrations using the same breast cancer animal model as in Example 19-1.

Specifically, the mice were divided into four groups (4 mg/kg, 8 mg/kg, 16 mg/kg and 32 mg/kg) in which 5 mice were allocated to each group. The antibody-treated group with 16 mg/kg dose showed partial tumor suppression and did not show any tumor suppression effect in a dose-depending manner, but the result of the complete remission, in which tumor growth was completely inhibited, had a tendency to increase, as the concentrations were increases (FIG. 35, Table 20).

TABLE 20

MDAMB453(Triple negative breast cancer) Xenograft model

| Dose groups of administered DNP004 | mouse# | Mass size(mm³) |
|---|---|---|
| 1 (Control) | 191 | 333 |
|  | 211 | 429 |
|  | 190 | 91 |
|  | 197 | 211 |
|  | 198 | 143 |

TABLE 20-continued

MDAMB453(Triple negative breast cancer) Xenograft model

| Dose groups of administered DNP004 | mouse# | Mass size(mm³) |
|---|---|---|
| 2 (4 mg/kg of DNP004) | 236 | 161 |
|  | 210 | 155 |
|  | 227 | 53 |
|  | 192 | 0 (complete remission) |
|  | 215 | 0 |
| 3 (8 mg/kg of DNP004) | 201 | 213 |
|  | 214 | 182 |
|  | 189 | 0 (complete remission) |
|  | 196 | 0 (complete remission) |
|  | 228 | 0 (complete remission) |
| 4 (16 mg/kg DNP004) | 224 | 333 |
|  | 217 | 486 |
|  | 195 | 0 (complete remission) |
|  | 206 | 135 |
|  | 205 | 0 (complete remission) |
| 5 (32 mg/kg of DNP004) | 222 | 0 (complete remission) |
|  | 234 | 175 |
|  | 209 | 0 (complete remission) |
|  | 200 | 0 (complete remission) |
|  | 188 | 0 (complete remission) |

19-3: Kidney Cancer Animal Model/Antibody-Administered Group with Single Concentration 786-O cells which are renal cell cancer cell line highly expressing the target antigen (CA-XII) of the humanized antibody (DNP004), were used to confirm mouse animal models and antitumor effects (FIG. 36).

Specifically, nude mice were subcutaneously injected with a 786-O cell line of 1.5×10⁷ cells. However, tumor formation was very late in this experimental set, unlike in the breast cancer cell line, and tumor formation was confirmed after about 70 days. DNP004 humanized antibody was administered in a mouse tail vein at a dose of 32 mg/kg to the treatment groups in which the tumor formation was confirmed. The tumors were measured twice a week at 3-4 day intervals during the experiment. The tumor growth curves were obtained from the beginning of the antibody administration to the end of the experiment, and the average tumor growth curve of 8 mice in DNP004 humanized antibody-administered group, compared to 3 mice of control group was obtained and shown in FIG. 36.

Therefore, the anti-cancer effect of DNP004 humanized antibody was confirmed in not only breast cancer but also kidney cancer.

What is claimed is:

1. An antibody or antigen-binding fragment thereof binding to carbonic anhydrase 12 (CA XII), comprising a VH-CDR1 having the amino acid sequence of SEQ ID NO: 14, a VH-CDR2 having the amino acid sequence of SEQ ID NO: 15, a VH-CDR3 having the amino acid sequence of SEQ ID NO: 28, a VL-CDR1 having the amino acid sequence of SEQ ID NO: 32 or 33, a VL-CDR2 having the amino acid sequence selected from the group consisting of SEQ ID NO: 34 to 42, and a VL-CDR3 having the amino acid sequence of SEQ ID NO: 31.

2. The antibody or antigen-binding fragment according to claim 1, wherein the antibody further comprises VH-framework sequence comprising the amino acid sequences of SEQ ID NOs: 43 to 46.

3. The antibody or antigen-binding fragment according to claim 1, wherein the antibody further comprises VL-framework sequence comprising the amino acid sequences of SEQ ID NOs: 47, 48, 51 and 52.

4. The antibody or antigen-binding fragment according to claim 3, wherein the antibody further comprises VL-framework sequences comprising the amino acid sequence of SEQ ID NO: 48 which comprises the amino acid sequence of SEQ ID NO: 49 or 50.

5. The antibody or antigen-binding fragment according to claim 1, wherein the antibody comprises VH-region amino acid sequence comprising the amino acid sequence of SEQ ID NO: 53, and VL-region amino acid sequence comprising the amino acid sequence selected from the group consisting of the amino acid sequences of SEQ ID NOs: 54 to 63.

6. The antibody or antigen-binding fragment according to claim 1, wherein the antibody has an agonist activity to CA XII.

7. The antibody or antigen-binding fragment according to claim 1, wherein the antigen-binding fragment is scFv, (scFv)2, Fab, Fab' or F(ab')2 of the anti-CA-XII antibody.

8. The antibody or antigen-binding fragment according to claim 1, wherein the antibody or the antigen-binding fragment is coupled to labeling agent, toxin, or anti-tumor agent.

9. The antibody or antigen-binding fragment according to claim 8, wherein the labeling agent is selected from the group consisting of a radioisotope, a hapten, a fluorescent material, a chromogen, and a dye.

10. The antibody or antigen-binding fragment according to claim 8, wherein the toxin is a radioisotope, a small molecule, a peptide or a protein.

11. The antibody or antigen-binding fragment according to claim 8, wherein the antibody or antigen-binding fragment is coupled with a toxin to form a fusion protein.

12. The antibody or antigen-binding fragment according to claim 8, wherein the fucoses bound to the antibody or antigen-binding fragment are partly or completely removed.

13. A nucleic acid molecule encoding the antibody or antigen-binding fragment according to claim 1.

14. A vector introduced by a nucleic acid molecule encoding the antibody or antigen-binding fragment according to claim 1.

15. A host expressing the antibody or antigen-binding fragment according to claim 1.

16. A pharmaceutical composition for prevention, alleviation or treatment of solid cancer, comprising the antibody or antigen-binding fragment according to claim 1.

17. The pharmaceutical composition according to claim 16, further comprising an anti-cancer chemical drug or other anti-cancer antibody.

18. A composition for detecting a solid cancer, comprising the antibody or antigen-binding fragment according to claim 1, wherein a sample is determined as the solid cancer if the sample shows a positive reaction to the antibody or antigen-binding fragment.

19. The composition for detecting a solid cancer according to claim 18, wherein the antibody or the antigen-binding fragment is coupled to a labeling agent.

* * * * *